United States Patent
Ha et al.

(10) Patent No.: US 11,097,084 B2
(45) Date of Patent: Aug. 24, 2021

(54) BALLOON CATHETER ASSEMBLY

(71) Applicant: Acclarent, Inc., Irvine, CA (US)

(72) Inventors: Hung V. Ha, San Jose, CA (US); Arthur M. Lin, Fremont, CA (US); Thomas R. Jenkins, Alameda, CA (US); Randy J. Kesten, Mountain View, CA (US); Scott O. Chamness, Menlo Park, CA (US); Ketan P. Muni, San Jose, CA (US)

(73) Assignee: Acclarent, Inc., Irvine, CA (US)

( * ) Notice: Subject to any disclaimer, the term of this patent is extended or adjusted under 35 U.S.C. 154(b) by 394 days.

(21) Appl. No.: 16/266,562

(22) Filed: Feb. 4, 2019

(65) Prior Publication Data

US 2019/0240467 A1 Aug. 8, 2019

Related U.S. Application Data

(62) Division of application No. 14/490,962, filed on Sep. 19, 2014, now Pat. No. 10,238,845.

(51) Int. Cl.
*A61M 29/02* (2006.01)
*A61M 25/10* (2013.01)
(Continued)

(52) U.S. Cl.
CPC ........ *A61M 29/02* (2013.01); *A61M 25/0113* (2013.01); *A61M 25/09041* (2013.01);
(Continued)

(58) Field of Classification Search
CPC ........ A61M 2025/09116; A61M 25/10; A61M 2025/09008; A61M 29/02;
(Continued)

(56) References Cited

U.S. PATENT DOCUMENTS 1,735,519 A * 11/1929 Vance .................... A61M 29/02
606/196
4,571,239 A * 2/1986 Heyman ................ A61M 25/10
604/544
(Continued)

FOREIGN PATENT DOCUMENTS

CN 103120825 A 5/2013
CN 103157170 A 6/2013
(Continued)

OTHER PUBLICATIONS

International Search Report and Written Opinion dated Feb. 12, 2016 for Application No. PCT/US2015/050396, 17 pgs.
(Continued)

*Primary Examiner* — Wade Miles
(74) *Attorney, Agent, or Firm* — Frost Brown Todd LLC

(57) ABSTRACT

A dilation catheter comprises a handle, a guidewire, a dilation catheter, a guidewire movement mechanism, and dilation catheter movement actuator. The guidewire movement mechanism is configured to translate to thereby cause translation of the guidewire relative to the handle. The dilation catheter movement mechanism is configured to translate to thereby cause translation of the dilation catheter relative to the handle. The guidewire movement mechanism also includes a rotation mechanism configured to impart rotation upon the guidewire. The rotation mechanism may include features configured to limit the amount that the guidewire may rotate. The rotation mechanism may also include features configured to convert linear movement of an actuator into rotational movement of the guidewire. The dilation catheter may include features configured to provide for side entry of the guidewire into the dilation catheter.

20 Claims, 92 Drawing Sheets

(51) Int. Cl.
  *A61M 25/01* (2006.01)
  *A61M 25/09* (2006.01)
(52) U.S. Cl.
  CPC . *A61M 25/104* (2013.01); *A61M 2025/09116* (2013.01); *A61M 2025/09125* (2013.01); *A61M 2029/025* (2013.01); *A61M 2210/0618* (2013.01); *A61M 2210/0662* (2013.01); *A61M 2210/0675* (2013.01); *A61M 2210/0681* (2013.01)
(58) Field of Classification Search
  CPC .. A61M 2029/025; A61B 17/24; A61B 1/233; A61F 2002/95; A61F 2/2433; A61F 2/958; A61F 2/9517
  See application file for complete search history.

(56) References Cited

U.S. PATENT DOCUMENTS

| | | | | |
|---|---|---|---|---|
| 4,976,691 | A * | 12/1990 | Sahota | A61M 25/0068 600/585 |
| 5,044,369 | A * | 9/1991 | Sahota | A61M 25/0068 600/435 |
| 5,152,749 | A * | 10/1992 | Giesy | A61B 17/3415 604/164.01 |
| 5,165,420 | A * | 11/1992 | Strickland | A61M 1/0058 600/581 |
| 5,300,085 | A * | 4/1994 | Yock | A61B 18/245 604/103.04 |
| 5,458,615 | A * | 10/1995 | Klemm | A61F 2/958 606/198 |
| 5,558,101 | A * | 9/1996 | Brooks | A61M 25/0662 600/585 |
| 5,749,920 | A * | 5/1998 | Quiachon | A61F 2/958 623/1.23 |
| 5,820,592 | A | 10/1998 | Hammerslag | |
| 5,826,576 | A | 10/1998 | West | |
| 5,882,333 | A | 3/1999 | Schaer et al. | |
| 5,919,161 | A | 7/1999 | Hill, III et al. | |
| 5,935,098 | A * | 8/1999 | Blaisdell | A61M 25/04 604/515 |
| 5,987,344 | A | 11/1999 | West | |
| 6,190,360 | B1 * | 2/2001 | Lancea | A61F 2/95 604/164.09 |
| 6,217,585 | B1 * | 4/2001 | Houser | A61F 2/958 606/108 |
| 6,238,430 | B1 * | 5/2001 | Klumb | A61F 2/88 623/1.11 |
| 6,511,471 | B2 | 1/2003 | Rosenman et al. | |
| 6,533,772 | B1 | 3/2003 | Sherts et al. | |
| 6,849,062 | B2 | 2/2005 | Kantor | |
| 7,048,711 | B2 | 5/2006 | Rosenmann et al. | |
| 7,056,314 | B1 | 6/2006 | Florio et al. | |
| 7,117,039 | B2 | 10/2006 | Manning et al. | |
| 7,630,676 | B2 | 12/2009 | Pirwitz | |
| 7,654,997 | B2 * | 2/2010 | Makower | A61B 17/24 604/509 |
| 7,803,150 | B2 * | 9/2010 | Chang | A61B 17/24 604/514 |
| 8,080,000 | B2 * | 12/2011 | Makower | A61M 29/02 604/510 |
| 8,090,433 | B2 * | 1/2012 | Makower | A61M 29/02 600/510 |
| 8,414,473 | B2 * | 4/2013 | Jenkins | A61B 1/126 600/104 |
| 8,961,398 | B2 * | 2/2015 | Makower | A61B 90/50 600/114 |
| 9,050,438 | B2 | 6/2015 | Rollins et al. | |
| 9,155,492 | B2 | 10/2015 | Jenkins et al. | |
| 9,826,999 | B2 * | 11/2017 | Jenkins | A61M 25/09 |
| 10,238,845 | B2 | 3/2019 | Ha et al. | |
| 2002/0004666 | A1 * | 1/2002 | Schwager | A61M 25/0068 606/191 |
| 2002/0115982 | A1 * | 8/2002 | Barbut | A61B 6/481 604/509 |
| 2002/0161389 | A1 * | 10/2002 | Boyle | A61M 25/09 606/200 |
| 2002/0177841 | A1 | 11/2002 | Moloney et al. | |
| 2002/0188341 | A1 * | 12/2002 | Elliott | A61F 2/95 623/1.1 |
| 2003/0051733 | A1 * | 3/2003 | Kotmel | A61B 5/085 128/207.14 |
| 2003/0055377 | A1 * | 3/2003 | Sirhan | A61M 25/104 604/103.04 |
| 2003/0074045 | A1 * | 4/2003 | Buzzard | A61F 2/95 623/1.11 |
| 2003/0114912 | A1 * | 6/2003 | Sequin | A61F 2/915 623/1.11 |
| 2003/0167060 | A1 * | 9/2003 | Buzzard | A61F 2/95 606/108 |
| 2004/0015150 | A1 * | 1/2004 | Zadno-Azizi | B29C 55/04 604/523 |
| 2004/0097988 | A1 * | 5/2004 | Gittings | A61F 2/915 606/153 |
| 2004/0122503 | A1 * | 6/2004 | Campbell | A61F 2/95 623/1.12 |
| 2004/0143283 | A1 | 7/2004 | McGill et al. | |
| 2004/0249434 | A1 * | 12/2004 | Andreas | A61F 2/915 623/1.11 |
| 2005/0004591 | A1 | 1/2005 | Bender et al. | |
| 2005/0038457 | A1 | 2/2005 | Vargas et al. | |
| 2005/0080476 | A1 * | 4/2005 | Gunderson | A61F 2/966 623/1.11 |
| 2005/0107738 | A1 * | 5/2005 | Slater | A61M 25/10 604/96.01 |
| 2005/0149159 | A1 * | 7/2005 | Andreas | A61M 25/0136 623/1.11 |
| 2005/0171568 | A1 | 8/2005 | Duffy | |
| 2005/0197623 | A1 | 9/2005 | Leeflang et al. | |
| 2006/0025721 | A1 | 2/2006 | Duffy et al. | |
| 2006/0229587 | A1 | 10/2006 | Beyar et al. | |
| 2008/0015544 | A1 * | 1/2008 | Keith | A61B 17/24 604/516 |
| 2008/0064920 | A1 | 3/2008 | Bakos et al. | |
| 2008/0183128 | A1 | 7/2008 | Morriss et al. | |
| 2008/0221550 | A1 | 9/2008 | Lee | |
| 2008/0275483 | A1 * | 11/2008 | Makower | A61B 17/0218 606/192 |
| 2009/0105639 | A1 | 4/2009 | Weitzner et al. | |
| 2010/0030031 | A1 | 2/2010 | Goldfarb et al. | |
| 2011/0004057 | A1 | 1/2011 | Goldfarb et al. | |
| 2012/0071856 | A1 * | 3/2012 | Goldfarb | A61M 29/00 604/514 |
| 2013/0102888 | A1 * | 4/2013 | Slim | C30B 7/10 600/424 |
| 2013/0274600 | A1 | 10/2013 | Jenkins et al. | |
| 2014/0074065 | A1 | 3/2014 | Muni et al. | |
| 2014/0276389 | A1 | 9/2014 | Walker | |
| 2015/0231371 | A1 | 8/2015 | Rollins et al. | |
| 2016/0121086 | A1 | 5/2016 | Castro et al. | |
| 2019/0240467 | A1 * | 8/2019 | Ha | A61M 25/104 |

FOREIGN PATENT DOCUMENTS

| | | |
|---|---|---|
| JP | 10-34376 A | 2/1989 |
| JP | 6-017751 U | 3/1994 |
| JP | 2000-126303 A | 5/2000 |
| JP | 2004-049583 A | 2/2004 |
| JP | 2005-323702 A | 11/2005 |
| JP | 2008-080119 A | 4/2008 |
| JP | 2014-200287 A | 10/2014 |
| WO | WO 2000/067834 A1 | 11/2000 |
| WO | WO 2001/068178 A1 | 9/2001 |
| WO | WO 2008/049088 A2 | 4/2008 |

(56) References Cited

OTHER PUBLICATIONS

Chinese Office Action, The First Office Action, and First Search, dated Aug. 5, 2019 for Application No. CN 201580063082.7, 15 pgs.
Chinese Office Action, The Second Office Action, dated Mar. 19, 2020 for Application No. CN 201580063082.7, 7 pgs.
Japanese Search Report by Registered Search Organization dated Mar. 13, 2020 for Application No. JP 2017-515109, 28 pgs.
European Communication dated Mar. 8, 2018 for Application No. 15781174.6, 5 pages.
Japanese Notice of Reasons for Refusal dated Mar. 18, 2019 for Application No. 2017-515109, 6 pages.

* cited by examiner

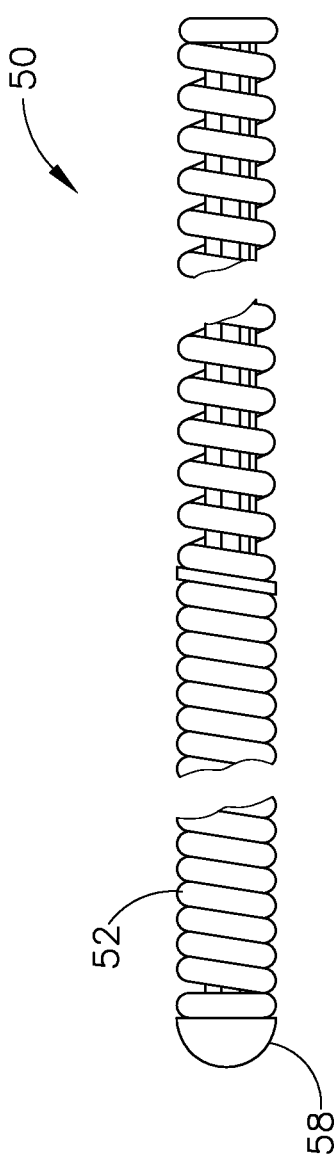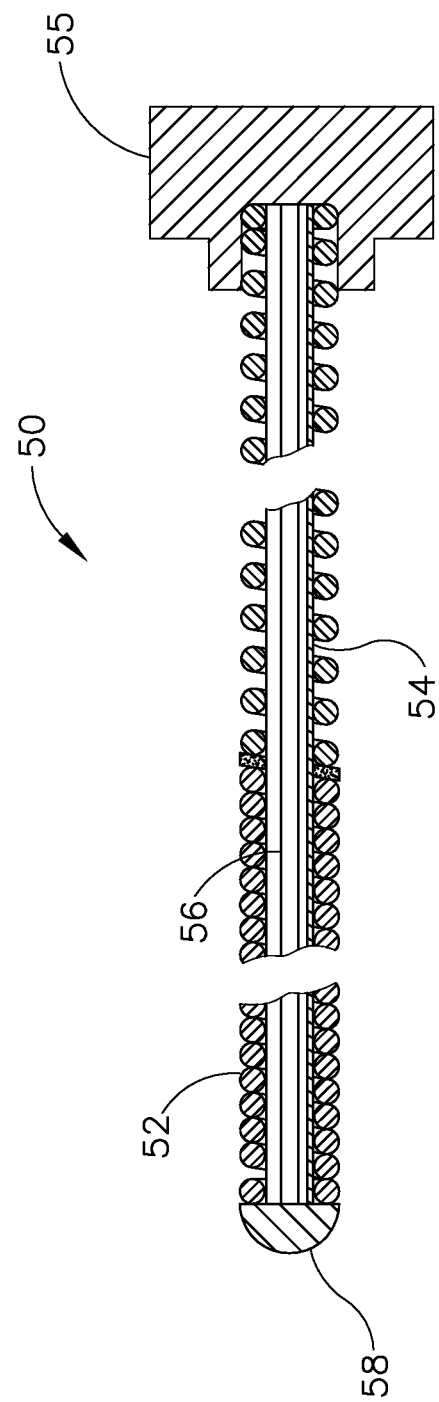
Fig.2
Fig.3

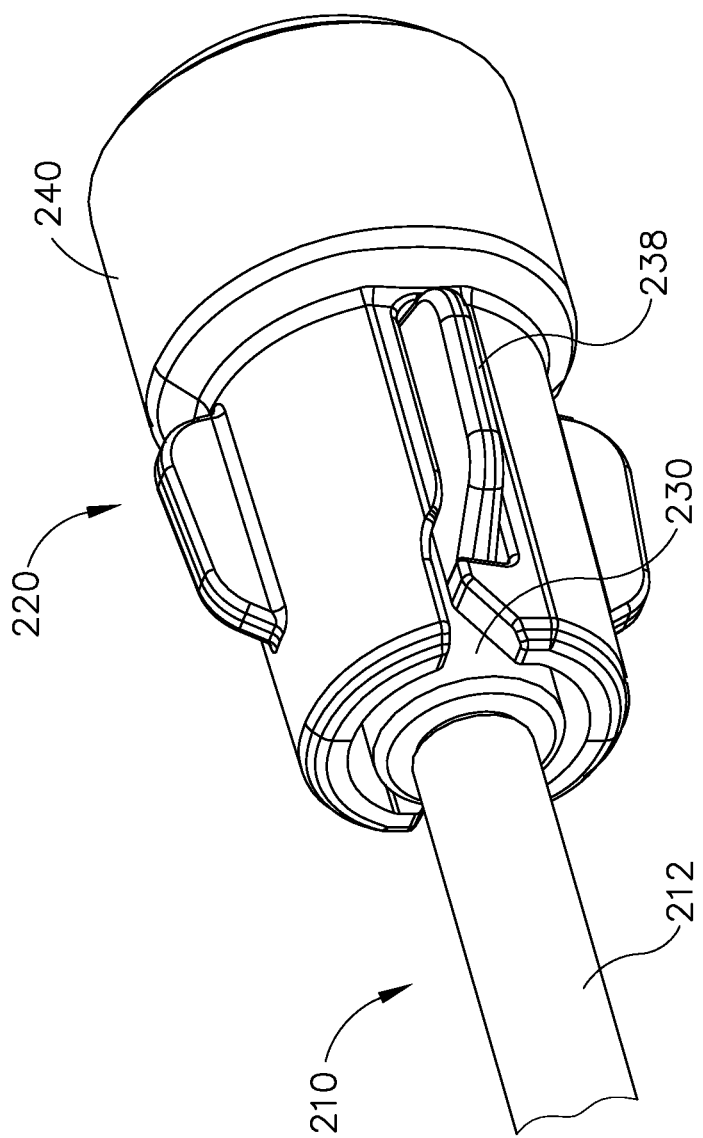

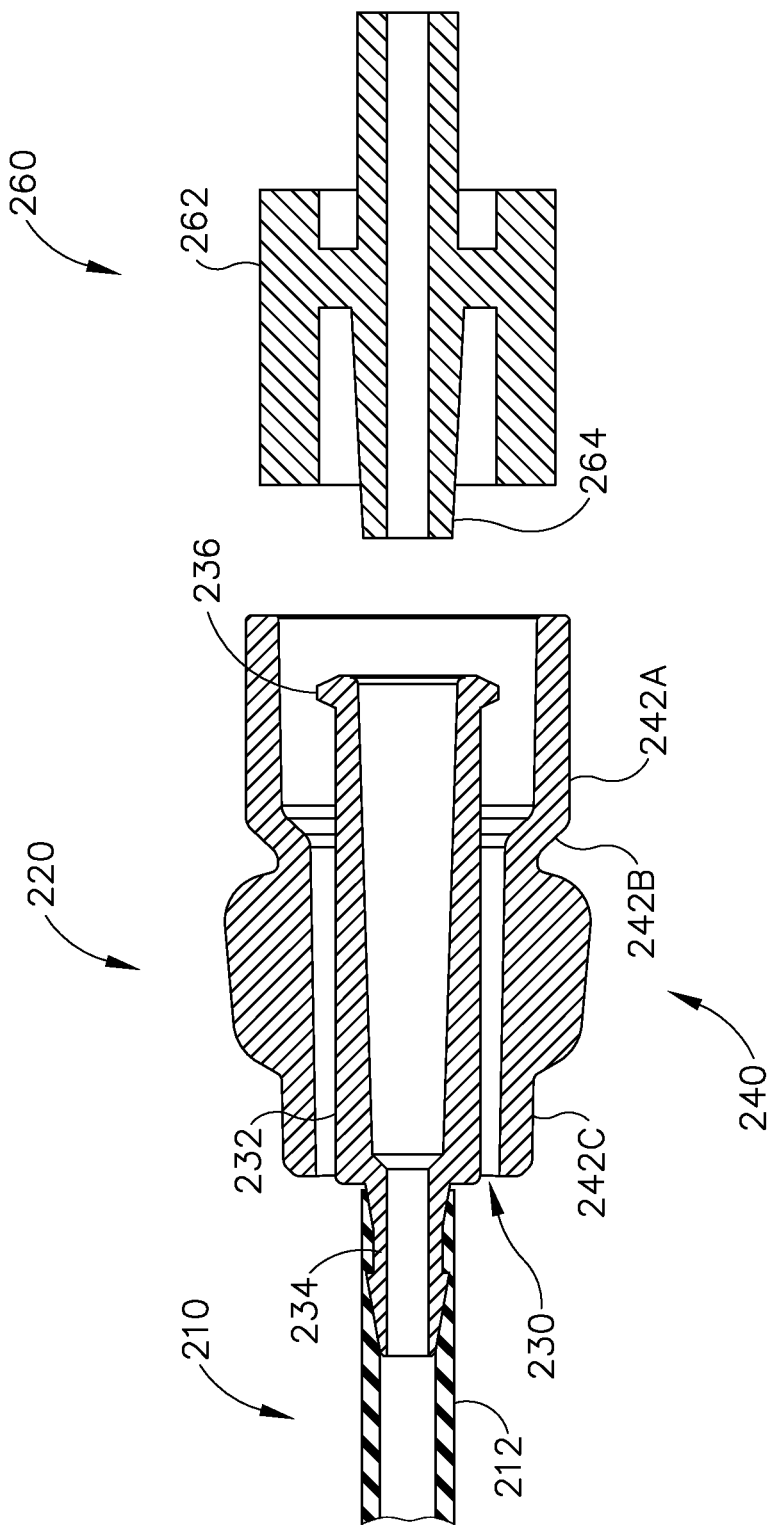

BALLOON CATHETER ASSEMBLY

This application is a division of U.S. application Ser. No. 14/490,962, filed Sep. 19, 2014, entitled "Balloon Catheter Assembly," issued as U.S. Pat. No. 10,238,845 on Mar. 26, 2019.

BACKGROUND

In some instances, it may be desirable to dilate an anatomical passageway in a patient. This may include dilation of ostia of paranasal sinuses (e.g., to treat sinusitis), dilation of the larynx, dilation of the Eustachian tube, dilation of other passageways within the ear, nose, or throat, etc. One method of dilating anatomical passageways includes using a guidewire and catheter to position an inflatable balloon within the anatomical passageway, then inflating the balloon with a fluid (e.g., saline) to dilate the anatomical passageway. For instance, the expandable balloon may be positioned within an ostium at a paranasal sinus and then be inflated, to thereby dilate the ostium by remodeling the bone adjacent to the ostium, without requiring incision of the mucosa or removal of any bone. The dilated ostium may then allow for improved drainage from and ventilation of the affected paranasal sinus. A system that may be used to perform such procedures may be provided in accordance with the teachings of U.S. Pub. No. 2011/0004057, entitled "Systems and Methods for Transnasal Dilation of Passageways in the Ear, Nose or Throat," published Jan. 6, 2011, now abandoned, the disclosure of which is incorporated by reference herein. An example of such a system is the Relieva® Spin Balloon Sinuplasty™ System by Acclarent, Inc. of Menlo Park, Calif.

A variable direction view endoscope may be used with such a system to provide visualization within the anatomical passageway (e.g., the ear, nose, throat, paranasal sinuses, etc.) to position the balloon at desired locations. A variable direction view endoscope may enable viewing along a variety of transverse viewing angles without having to flex the shaft of the endoscope within the anatomical passageway. Such an endoscope that may be provided in accordance with the teachings of U.S. Pub. No. 2010/0030031, entitled "Swing Prism Endoscope," published Feb. 4, 2010 now abandoned, the disclosure of which is incorporated by reference herein. An example of such an endoscope is the Acclarent Cyclops™ Multi-Angle Endoscope by Acclarent, Inc. of Menlo Park, Calif.

While a variable direction view endoscope may be used to provide visualization within the anatomical passageway, it may also be desirable to provide additional visual confirmation of the proper positioning of the balloon before inflating the balloon. This may be done using an illuminating guidewire. Such a guidewire may be positioned within the target area and then illuminated, with light projecting from the distal end of the guidewire. This light may illuminate the adjacent tissue (e.g., hypodermis, subdermis, etc.) and thus be visible to the naked eye from outside the patient through transcutaneous illumination. For instance, when the distal end is positioned in the maxillary sinus, the light may be visible through the patient's cheek. Using such external visualization to confirm the position of the guidewire, the balloon may then be advanced distally along the guidewire into position at the dilation site. Such an illuminating guidewire may be provided in accordance with the teachings of U.S. Pub. No. 2012/0078118, entitled "Sinus Illumination Lightwire Device," published Mar. 29, 2012, now U.S. Pat. No. 9,155,492, issued on Oct. 13, 2015, the disclosure of which is incorporated by reference herein. An example of such an illuminating guidewire is the Relieva Luma Sentry™ Sinus Illumination System by Acclarent, Inc. of Menlo Park, Calif.

It may be desirable to provide easily controlled inflation/deflation of a balloon in dilation procedures, including procedures that will be performed only by a single operator. While several systems and methods have been made and used to inflate an inflatable member such as a dilation balloon, it is believed that no one prior to the inventors has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

FIG. 2 depicts a side elevational view of an exemplary illuminating guidewire suitable for use with the dilation catheter system of FIG. 1;

FIG. 3 depicts a side cross-sectional view of the illuminating guidewire of FIG. 2;

FIG. 10 depicts a perspective view of a coupler assembly of the irrigation catheter assembly of FIG. 9;

FIG. 15A depicts a cross-sectional side elevational view of the proximal end of the irrigation catheter assembly of FIG. 9 and the inflation coupler of FIG. 13, with the inflation coupler separated from the coupler assembly of the irrigation catheter assembly;

Figure 1:
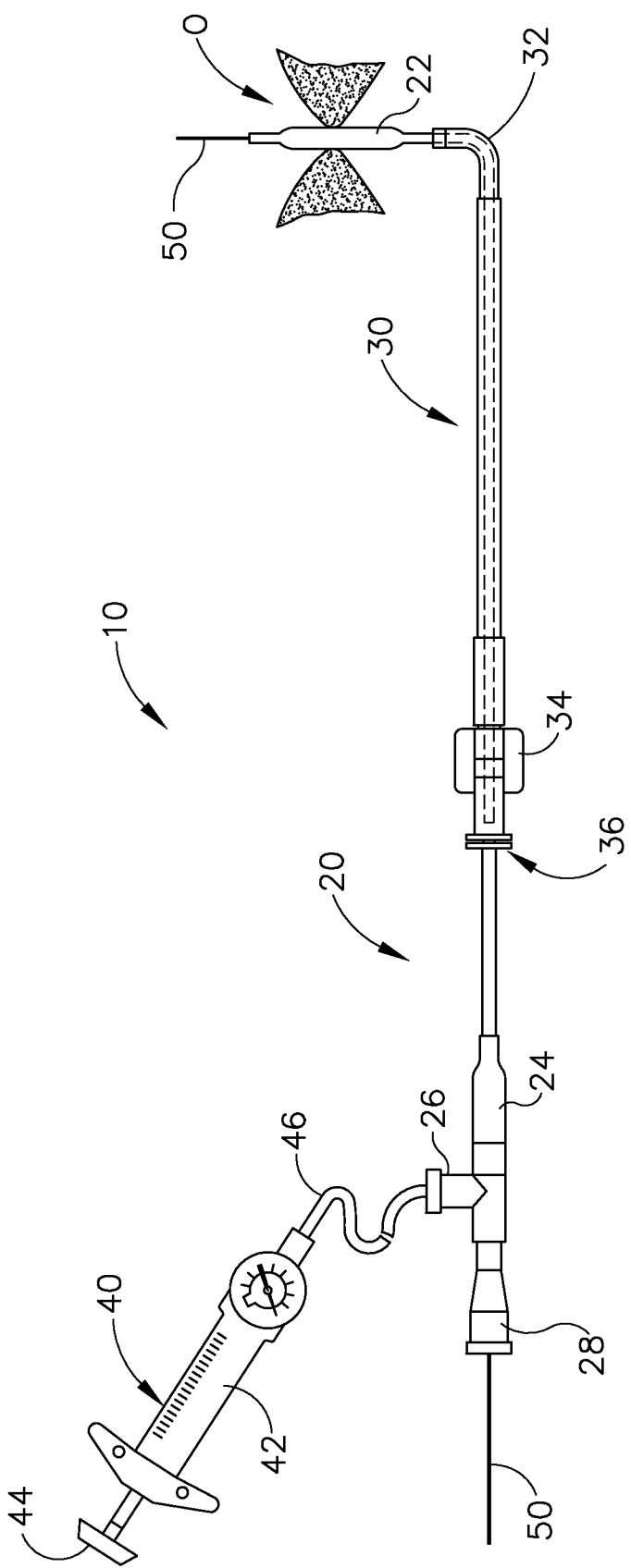
FIG. 1 depicts a side elevational view of an exemplary dilation catheter system.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

It will be appreciated that the terms "proximal" and "distal" are used herein with reference to a clinician gripping a handpiece assembly. Thus, an end effector is distal with respect to the more proximal handpiece assembly. It will be further appreciated that, for convenience and clarity, spatial terms such as "top" and "bottom" also are used herein with respect to the clinician gripping the handpiece assembly. However, surgical instruments are used in many orientations and positions, and these terms are not intended to be limiting and absolute.

It is further understood that any one or more of the teachings, expressions, versions, examples, etc. described herein may be combined with any one or more of the other teachings, expressions, versions, examples, etc. that are described herein. The following-described teachings, expressions, versions, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. Overview of Exemplary Dilation Catheter System

FIG. 1 shows an exemplary dilation catheter system (10) that may be used to dilate the ostium of a paranasal sinus; or to dilate some other anatomical passageway (e.g., within the ear, nose, or throat, etc.). Dilation catheter system (10) of this example comprises a dilation catheter (20), a guide catheter (30), an inflator (40), and a guidewire (50). By way of example only, dilation catheter system (10) may be configured in accordance with at least some of the teachings of U.S. Patent Pub. No. 2011/0004057, now abandoned, the disclosure of which is incorporated by reference herein. In some versions, at least part of dilation catheter system (10) is configured similar to the Relieva® Spin Balloon Sinuplasty™ System by Acclarent, Inc. of Menlo Park, Calif.

The distal end of dilation catheter (20) includes an inflatable dilator (22). The proximal end of dilation catheter (20) includes a grip (24), which has a lateral port (26) and an open proximal end (28). Dilation catheter (20) includes a first lumen (not shown) that provides fluid communication between lateral port (26) and the interior of dilator (22). Dilator (22) may include any appropriate material, including a polyether block amide such as Pebax®. Dilator catheter (20) also includes a second lumen (not shown) that extends from open proximal end (28) to an open distal end that is distal to dilator (22). This second lumen is configured to slidably receive guidewire (50). The first and second lumens of dilator catheter (20) are fluidly isolated from each other. Thus, dilator (22) may be selectively inflated and deflated by communicating fluid along the first lumen via lateral port (26) while guidewire (50) is positioned within the second lumen. In some versions, dilator catheter (20) is configured similar to the Relieva Ultirra™ Sinus Balloon Catheter by Acclarent, Inc. of Menlo Park, Calif. In some other versions, dilator catheter (20) is configured similar to the Relieva Solo Pro™ Sinus Balloon Catheter by Acclarent, Inc. of Menlo Park, Calif. Other suitable forms that dilator catheter (20) may take will be apparent to those of ordinary skill in the art in view of the teachings herein.

Guide catheter (30) of the present example includes a bent distal end (32) and a grip (34) at its proximal end. Grip (34) has an open proximal end (36). Guide catheter (30) defines a lumen that is configured to slidably receive catheter (20), such that guide catheter (30) may guide dilator (22) out through bent distal end (32). In some versions, guide catheter (30) is configured similar to the Relieva Flex™ Sinus Guide Catheter by Acclarent, Inc. of Menlo Park, Calif. Other suitable forms that guide catheter (30) may take will be apparent to those of ordinary skill in the art in view of the teachings herein.

Inflator (40) of the present example comprises a barrel (42) that is configured to hold fluid and a plunger (44) that is configured to reciprocate relative to barrel (42) to selectively discharge fluid from (or draw fluid into) barrel (42). Barrel (42) is fluidly coupled with lateral port (26) via a flexible tube (46). Thus, inflator (40) is operable to add fluid to dilator (22) or withdraw fluid from dilator (22) by translating plunger (44) relative to barrel (42). In the present example, the fluid communicated by inflator (40) comprises saline, though it should be understood that any other suitable fluid may be used. There are various ways in which inflator (40) may be filled with fluid (e.g., saline, etc.). By way of example only, before flexible tube (46) is coupled with lateral port (26), the distal end of flexible tube (46) may be placed in a reservoir containing the fluid. Plunger (44) may then be retracted from a distal position to a proximal position to draw the fluid into barrel (42). Inflator (40) may then be held in an upright position, with the distal end of barrel (42) pointing upwardly, and plunger (44) may then be advanced to an intermediate or slightly distal position to purge any air from barrel (42). The distal end of flexible tube (46) may then be coupled with lateral port (26).

As best seen in FIGS. 2-3, guidewire (50) of the present example comprises a coil (52) positioned about a guidewire (54). An illumination fiber (56) extends along the interior of guidewire (54) and terminates in an atraumatic lens (58). A connector (55) at the proximal end of guidewire (50) enables optical coupling between illumination fiber (56) and a light source (not shown). Illumination fiber (56) may comprise one or more optical fibers. Lens (58) is configured to project light when illumination fiber (56) is illuminated by the light source, such that illumination fiber (56) transmits light from the light source to the lens (58). In some versions, the distal end of guidewire (50) is more flexible than the proximal end of guidewire (50). Guidewire (50) has a length enabling the distal end of guidewire (50) to be positioned distal to dilator (22) while the proximal end of guidewire (50) is positioned proximal to grip (24). Guidewire (50) may include indicia along at least part of its length (e.g., the proximal portion) to provide the operator with visual feedback indicating the depth of insertion of guidewire (50) relative to dilation catheter (20). By way of example only, guidewire (50) may be configured in accordance with at least some of the teachings of U.S. Pub. No. 2012/0078118, now U.S. Pat. No. 9,155,492, the disclosure of which is incorporated by reference herein. In some versions, guidewire (50) is configured similar to the Relieva Luma Sentry™ Sinus Illumination System by Acclarent, Inc. of Menlo Park, Calif. Other suitable forms that guidewire (50) may take will be apparent to those of ordinary skill in the art in view of the teachings herein.

In an exemplary dilation procedure, guide catheter (30) may first be positioned near the targeted anatomical passageway, such as a sinus ostium (O). Dilator (22) and the distal end of guidewire (50) may be positioned within or proximal to bent distal end (32) of guide catheter (30) at this stage. Guide catheter (30) is initially inserted into the nose of the patient and is advanced to a position that is within or near the ostium (O) to be dilated. This positioning of guide catheter (30) may be performed under visualization provided by an endoscope. After guide catheter (30) has been positioned, the operator may advance guidewire (50) distally through guide catheter (30) such that a distal portion of the guidewire (50) passes through the sinus ostium (O) and into the sinus cavity. The operator may illuminate illumination fiber (56) and lens (58), which may provide transcutaneous illumination through the patient's face to enable the operator to visually confirm positioning of the distal end of guidewire (50) with relative ease.

With guide catheter (30) and guidewire (50) suitably positioned, dilation catheter (20) is advanced along guidewire (50) and through bent distal end (32) of guide catheter (30), with dilator (22) in a non-dilated state until dilator (22) is positioned within the sinus ostium (O) (or some other targeted anatomical passageway). After dilator (22) has been positioned within the ostium (O), dilator (22) may be inflated, thereby dilating the ostium. To inflate dilator (22), plunger (44) may be actuated to push saline from barrel (42) of inflator (40) through dilation catheter (20) into dilator (22). The transfer of fluid expands dilator (22) to an expanded state to open or dilate the ostium (O), such as by remodeling the bone, etc., forming ostium (O). By way of example only, dilator (22) may be inflated to a pressure of about 10 to about 12 atmospheres. Dilator (22) may be held at this volume for a few seconds to sufficiently open the ostium (O) (or other targeted anatomical passageway). Dilator (22) may then be returned to a non-expanded state by reversing plunger (44) of inflator (40) to bring the saline back to inflator (40). Dilator (22) may be repeatedly inflated and deflated in different ostia and/or other targeted anatomical passageways. Thereafter, dilation catheter (20), guidewire (50), and guide catheter (30) may be removed from the patient.

In some instances, it may be desirable to irrigate the paranasal sinus and/or the nasal cavity after dilation catheter (20) has been used to dilate an ostium (O). Such irrigation may be performed to flush out purulence, etc. that may be present after the dilation procedure. By way of example only, such irrigation may be carried out in accordance with at least some of the teachings of U.S. Pub. No. 2008/0183128, entitled "Methods, Devices and Systems for Treatment and/or Diagnosis of Disorders of the Ear, Nose and Throat," published Jul. 31, 2008, now abandoned, the disclosure of which is incorporated by reference herein. An example of an irrigation catheter that may be fed through guide catheter (30) to reach the irrigation site after removal of dilation catheter (20) is the Relieva Vortex® Sinus Irrigation Catheter by Acclarent, Inc. of Menlo Park, Calif. Another example of an irrigation catheter that may be fed through guide catheter (30) to reach the irrigation site after removal of dilation catheter (20) is the Relieva Ultirra® Sinus Irrigation Catheter by Acclarent, Inc. of Menlo Park, Calif. Of course, irrigation may be provided in the absence of a dilation procedure; and a dilation procedure may be completed without also including irrigation.

II. Overview of Exemplary Dilation Catheter Instrument

Figure 4:
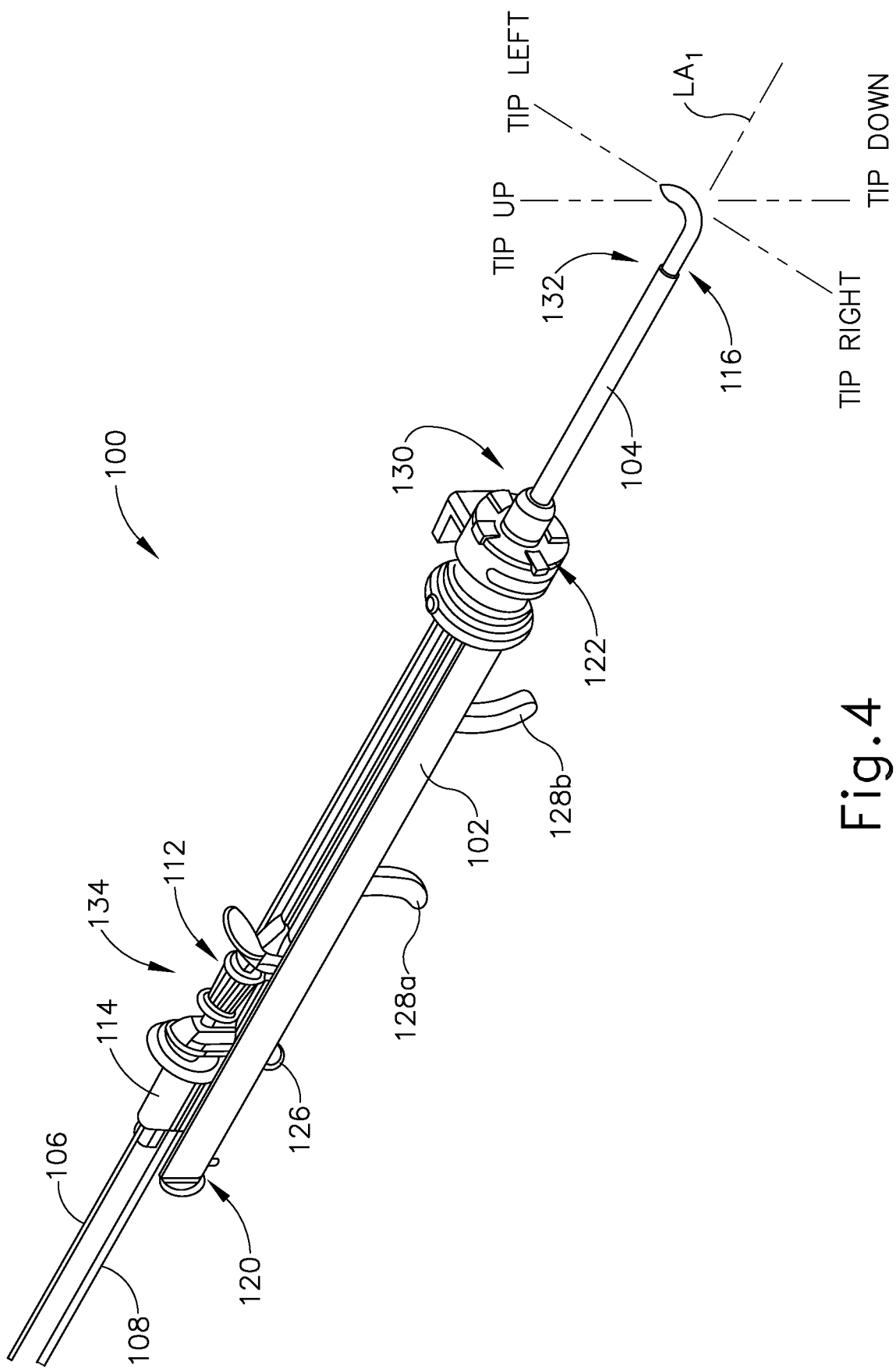
FIG. 4 depicts a perspective view of an instrument suitable for incorporation into the dilation catheter system of FIG. 1.
Figure 5:
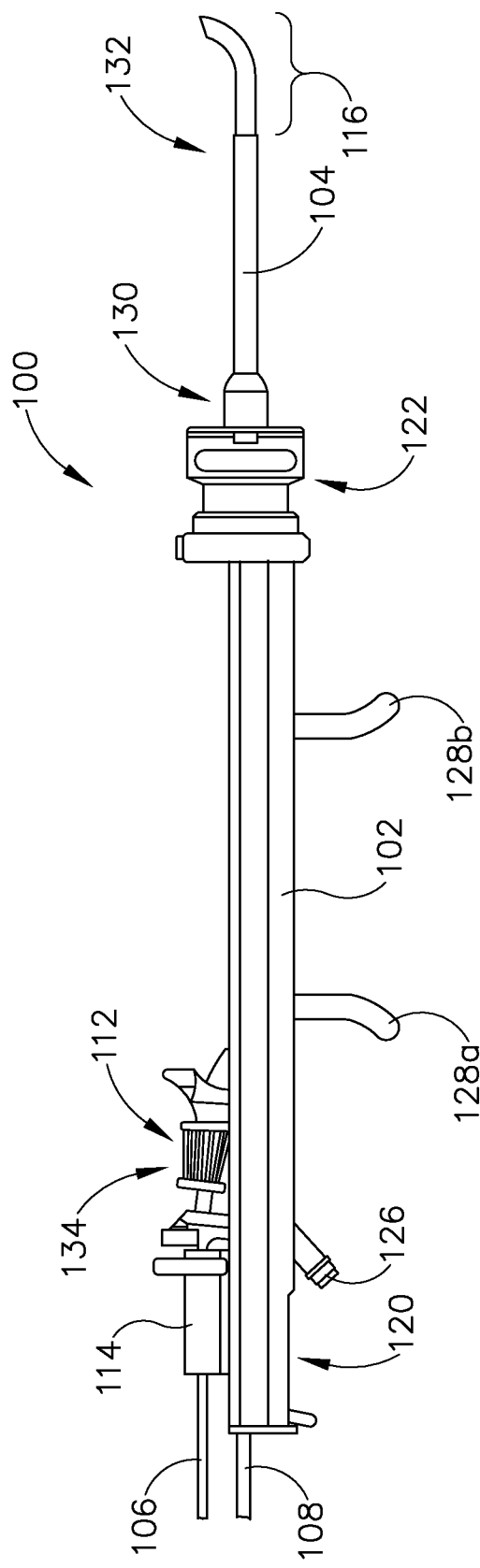
FIG. 5 depicts a side elevational view of the instrument of FIG. 4.
Figure 6:
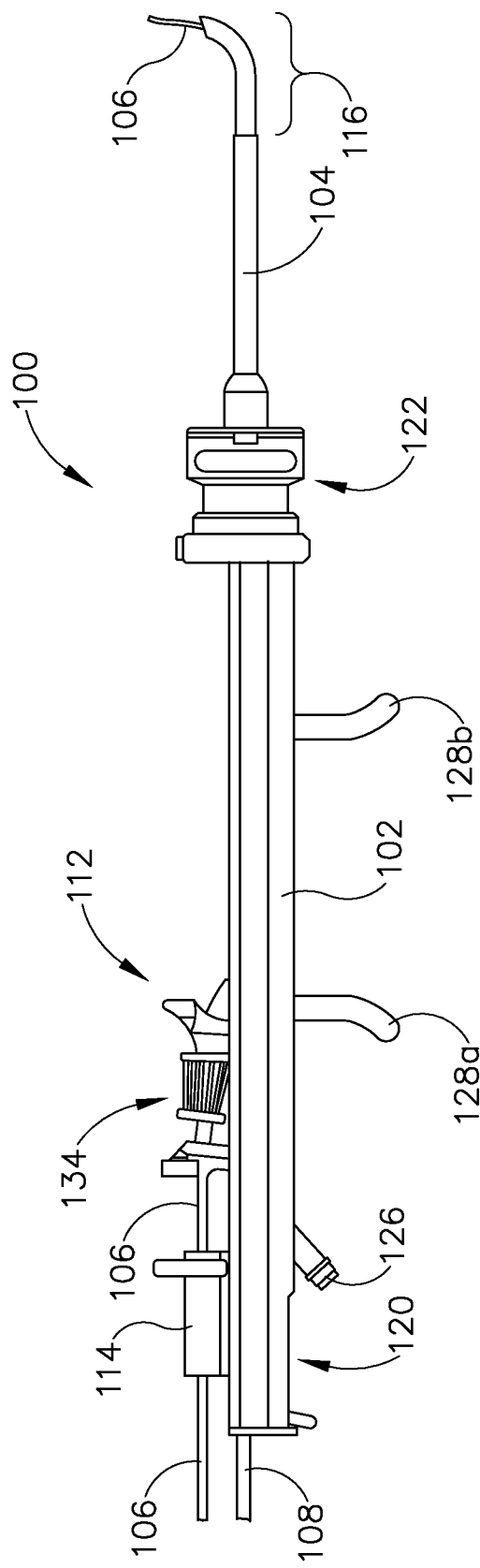
FIG. 6 depicts a side elevational view of the instrument of FIG. 4 with a guidewire of the instrument advanced distally.

FIGS. 4-6 show an instrument (100) that may be used to treat a paranasal sinus drainage passageway (e.g., a frontal recess, a frontal sinus ostium, a maxillary sinus ostium, a sphenoid sinus ostium, etc.). For instance, instrument (100) may be used to dilate a paranasal sinus drainage passageway. The various features of instrument (100) may be readily incorporated into dilation catheter system (10) discussed above. Instrument (100) of this example comprises a handle (102), a guide catheter (104), a guidewire (106), a dilation catheter (108), a guidewire movement mechanism (112), a dilation catheter movement actuator (114), a detachable guide tip (116) (shown with a curved (angled) tip in a "tip up" orientation), and a guidewire support (118) (see FIGS. 7-8). FIG. 4 includes a series of markers depicting alternative orientations of guide tip (116). In particular, a "tip up," a "tip left," a "tip down," and a "tip right" orientation of guide tip (116) are shown in FIG. 4.

As shown in FIGS. 4-6, handle (102) of the present example includes a proximal end (120) and a distal end (122); and defines a longitudinal axis (LA1) along the length of handle (102). Handle (102) further includes a fluid port (126) and finger anchoring pegs (128a) and (128b). In the present example, fluid port (126) is configured to couple with a source of suction to provide suction via guide catheter (104). In addition or in the alternative, fluid port (126) may be coupled with a fluid source to provide irrigation. Other suitable ways in which fluid port (126) may be made and used will be apparent to those of ordinary skill in the art in view of the teachings herein. Handle (102) is sized and shaped such that instrument (100) can be manipulated and operated by a user (such as a physician) in a convenient and efficient single-handed manner if so desired, with finger anchoring pegs (128a) and (128b) promoting gripping of handle (102) with a single hand. Handle (102) can be formed of any suitable material including, for example, polycarbonate and ABS (acetonitrile butadiene styrene) and can be manufactured using any suitable technique including, for example, injection molding of two clamshell handle halves. Various suitable materials and methods that may be used to manufacture handle (102) will be apparent to those of ordinary skill in the art in view of the teachings herein.

In the present example, guide catheter (104) serves as a substitute for guide catheter (30) described above and shown in FIG. 1. Guide catheter (104) of this example is attached to distal end (122) of handle (102) and defines an inner lumen (i.e., inner passage). Guide catheter (104) extends along longitudinal axis (LA1) and has a proximal end (130) and a distal end (132). Guide catheter (104) can be formed of any suitable materials including, for example, stainless steel, polymeric materials, and combinations thereof. By way of example only, the lumen of guide catheter (104) may have a diameter between about 0.070 and 0.150 inches. Alternatively, any other suitable dimensions may be used.

Detachable guide tip (116) is configured for removable attachment to, and detachment from, distal end (132) of guide catheter (104). However, detachable tips can be attached and detached from instrument (100) at any suitable location. For example, guide tip (116) can be attached anywhere along guide catheter (104) or at the distal end of handle (102). Guide tip (116) can be formed of any suitable material including, for example, stainless steel, polymeric materials and combinations thereof. It should also be understood that guide catheter (104) may have an integral tip that is pre-bent, malleable, or otherwise formed such that a separate, detachable guide tip (116) may be omitted from instrument (100). In other words, detachable guide tip (116) is merely optional.

Figure 7:
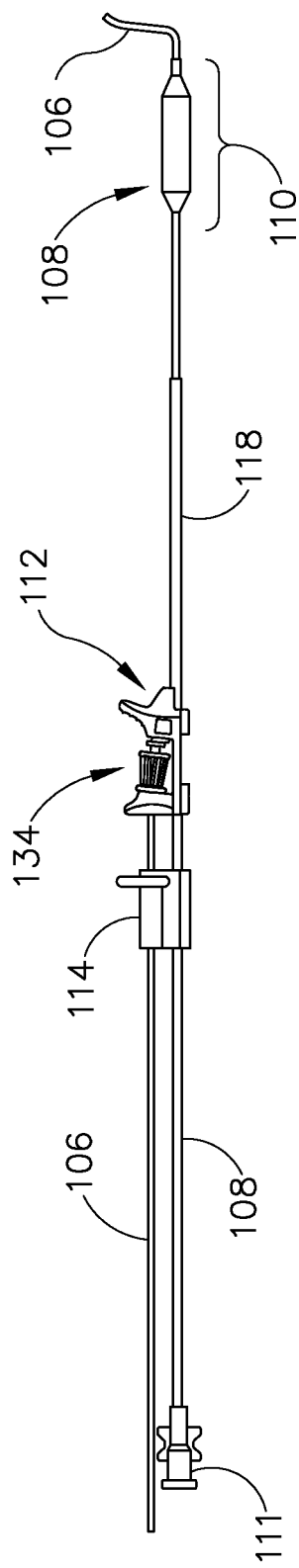
FIG. 7 depicts a side elevational view of the guidewire, a dilation catheter, a dilation catheter movement mechanism, a guidewire movement mechanism, and a guidewire support of the instrument of FIG. 4, with a working balloon segment of the dilation catheter shown in an inflated state.
Figure 8:
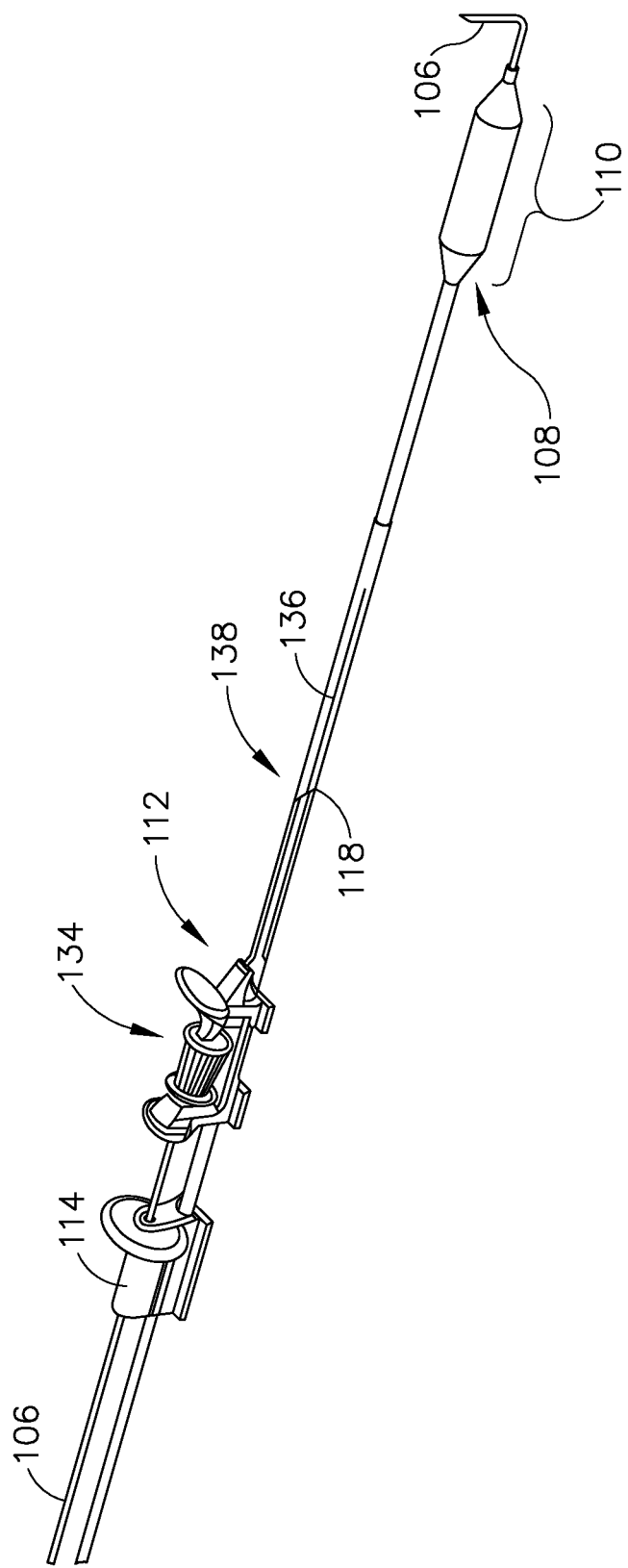
FIG. 8 depicts a perspective view of the guidewire, dilation catheter, dilation catheter movement mechanism, guidewire movement mechanism, and guidewire support of FIG. 7.

Dilation catheter (108) serves as a substitute for dilator catheter (20) described above. As best seen in FIGS. 7-8, dilation catheter (108) of the present example comprises an inflatable balloon (110) and an inflation port (111). Dilation catheter (108) further defines a first inner lumen and a second inner lumen. The first inner lumen of dilation catheter (108) distally terminates in balloon (110) and provides a path for fluid communication between inflation port (111) and balloon (110). Inflation port (111) may thus be coupled with a fluid source (e.g., inflator (40), etc.) to provide selective inflation of balloon (110) in accordance with the teachings herein. The second inner lumen of dilation catheter (108) extends all the way to the open distal end of dilation catheter (108) and provides a passageway to slidably receive guidewire (106) as described below. Dilation catheter (108) is slidably disposed at least partially in handle (102) and in the lumen of guide catheter (104). Dilation catheter (108) may be configured and operable in accordance with any suitable dilation catheters known to one skilled in the art.

During operation of instrument (100), dilation catheter (108) may be translated between a proximal position and a distal position. In particular, dilation catheter (108) may be longitudinally advanced and retracted relative to handle (102) and through the lumen of guide catheter (104). When dilation catheter (108) is in the proximal position, balloon (110) may be positioned within the lumen of guide catheter (104), proximal to the distal end (132) of guide catheter (104). When dilation catheter (108) is in the distal position, balloon (110) may be positioned distal to the distal end (132) of guide catheter (104). In versions where guide tip (116) is included, balloon (110) may also be positioned distal to the distal end of guide tip (116) when dilation catheter (108) is in the distal position.

Dilation catheter movement actuator (114) is operatively disposed on handle (102) and is operable to provide the above-described longitudinal advancement and retraction of dilation catheter (108) between the proximal and distal positions. In particular, dilation catheter movement actuator (114) provides such movement by longitudinally sliding along handle (102). Although dilation catheter movement actuator (114) of the present example is described as sliding along the length of handle (102), movement of dilation catheter (108) can be accomplished by any other suitable operation. In some variations, dilation catheter movement actuator (114) is rotatable relative to handle (102) to provide longitudinal advancement and retraction of dilation catheter (108). Various suitable ways in which dilation catheter (108) may be longitudinally advanced and retracted relative to handle (102) and through the lumen of guide catheter (104) will be apparent to those of ordinary skill in the art in view of the teachings herein.

In the present example, guidewire (106) serves as a substitute for guidewire (50) described above. Guidewire (106) of this example is slidably disposed in dilation catheter movement actuator (114), at least partially in handle (102), in guidewire support (118), and in the second inner lumen of dilation catheter (108). Guidewire (106) may be configured and operable in accordance with any suitable guidewire known to one skilled in the art including, for example, an illuminating guidewire that is configured to provide a user with confirmation of sinus access via transillumination (e.g., guidewire (50) described above, etc.). Guidewire support (118) of instrument (100) is operatively disposed within handle (102) and provides additional column strength to guidewire (106), such that guidewire support (118) prevents guidewire (106) from buckling within handle (102) during advancement of guidewire (106) relative to handle (102). As shown in FIG. 8, guidewire support (118) includes a slit-shaped opening (136) into which guidewire (106) is fed by guidewire movement mechanism (112). In some versions, guidewire support (118) comprises a hypotube. In addition or in the alternative, guidewire support (118) may be provided by dilation catheter (108).

Guidewire movement mechanism (112) is operatively disposed on handle (102) and is operable to longitudinally advance and retract guidewire (106) relative to handle (102), through guidewire support (118), and through the lumen of guide catheter (104) by longitudinal sliding of guidewire movement mechanism (112) along the length of handle (102). FIG. 5 shows guidewire movement mechanism (112) and guidewire (106) in a proximal position, where the distal end of guidewire (106) is positioned proximal to the distal end of detachable guide tip (116). In some versions, the distal end of guidewire (106) is also positioned proximal to distal end (132) of guide catheter (104) when guidewire (106) is in a proximal position as shown in FIG. 5. FIG. 6 shows guidewire movement mechanism (112) and guidewire (106) in a distal position, where the distal end of guidewire (106) is positioned distal to the distal end of detachable guide tip (116). It should be understood that guidewire movement mechanism (112) may be used to advance the distal end of guidewire (106) through an opening of a paranasal sinus (or some other passageway); and then dilation catheter movement actuator (114) may be used to advance dilation catheter (108) along guidewire (106) to position balloon (110) in the opening of the paranasal sinus as described above. Balloon (110) may then be inflated to dilate the opening of the paranasal sinus.

In the present example, guidewire movement mechanism (112) further includes an integrated guidewire locking and rotation knob (134) that is operable to rotate guidewire (106) about the longitudinal axis of guidewire (106). Knob (134) is secured to guidewire (106) such that knob (134) and guidewire (106) rotate unitarily with each other about the longitudinal axis of guidewire (106). Knob (134) is also configured for securely locking and unlocking guidewire (106) to guidewire movement mechanism (112). Although guidewire movement mechanism (112) of the present example is described as sliding along the length of handle (102), movement of guidewire (106) can be accomplished by any other suitable operation. In some variations, guidewire movement mechanism (112) is rotatable relative to handle (102) to provide longitudinal advancement and retraction of guidewire (106). Various suitable ways in which guidewire (106) may be longitudinally advanced and retracted relative to handle (102) and through the second lumen of dilation catheter (108) will be apparent to those of ordinary skill in the art in view of the teachings herein.

In addition to or as an alternative to being constructed and operable in accordance with the above teachings, instrument (100) may be constructed and operable in accordance with at least some of the teachings of U.S. Pub. No. 2012/0071856, entitled "Medical Device and Method for Treatment of a Sinus Opening," published Mar. 22, 2012, now U.S. Pat. No. 9,554,817, issued Jan. 31, 2017, the disclosure of which is incorporated by reference herein. By way of example only, instrument (100) may include a "clicker" and/or other feature that provides audible and/or tactile feedback as knob (134) is rotated to rotate guidewire (106), as described in U.S. Pub. No. 2012/0071856, now U.S. Pat. No. 9,554,817. Of course, various other teachings of U.S. Pub. No. 2012/0071856, now U.S. Pat. No. 9,554,817, may also be readily incorporated into instrument (100). In addition or in the alternative, instrument (100) may be modified in accordance with the various teachings below.

III. Exemplary Irrigation Catheter Assembly

As noted above, it may be desirable in some instances to irrigate the paranasal sinus and/or the nasal cavity before and/or after dilation catheter (20, 108) has been used to dilate an opening of a paranasal sinus (or other passageway). An irrigation procedure may entail removal of dilation catheter (20, 108) from the lumen of guide catheter (30, 104), followed by insertion of an irrigation catheter through the lumen of guide catheter (30, 104) such that a working distal end of the irrigation catheter protrudes distally from the distal end of guide catheter (30, 104) (and any detachable guide tip (116), if applicable). Alternatively, an irrigation catheter may be advanced distally through the lumen of dilation catheter (20, 108), such that a working distal end of the irrigation catheter protrudes distally from the distal end of dilation catheter (20, 108). As yet another merely illustrative alternative, dilation catheter (20, 108) may include an integral irrigating distal tip and a separate irrigation lumen that is isolated from the inflation lumen, such that dilation catheter (20, 108) is used to provide irrigation. In some such versions, the second lumen (which receives guidewire (50, 106) also provides a path for irrigation fluid. As still another merely illustrative variation, the lumen of a guide catheter (30, 104) may provide a gap about the outer diameter of a dilation catheter (20, 108), permitting irrigation fluid to be communicated out through the open distal end (132) of guide catheter (30, 104). Other suitable ways in which irrigation may be provided will be apparent to those of ordinary skill in the art in view of the teachings herein.

Regardless of how irrigation is provided, the proximal end of the conduit that is used to provide irrigation may include an irrigation port that is operable to detachably couple with a source of irrigation fluid. Likewise, the proximal end of the conduit that is used to provide inflation of balloon (22, 110) may include an inflation port (e.g., port (26, 111), etc.) that is operable to detachably couple with a source of inflation fluid. It may be desirable to provide an irrigation port configuration that prevents an inflation fluid source from being inadvertently coupled with the irrigation port; yet permits an irrigation fluid source to couple with the irrigation port. One merely illustrative example of such a configuration is described in greater detail below.

Figure 9:
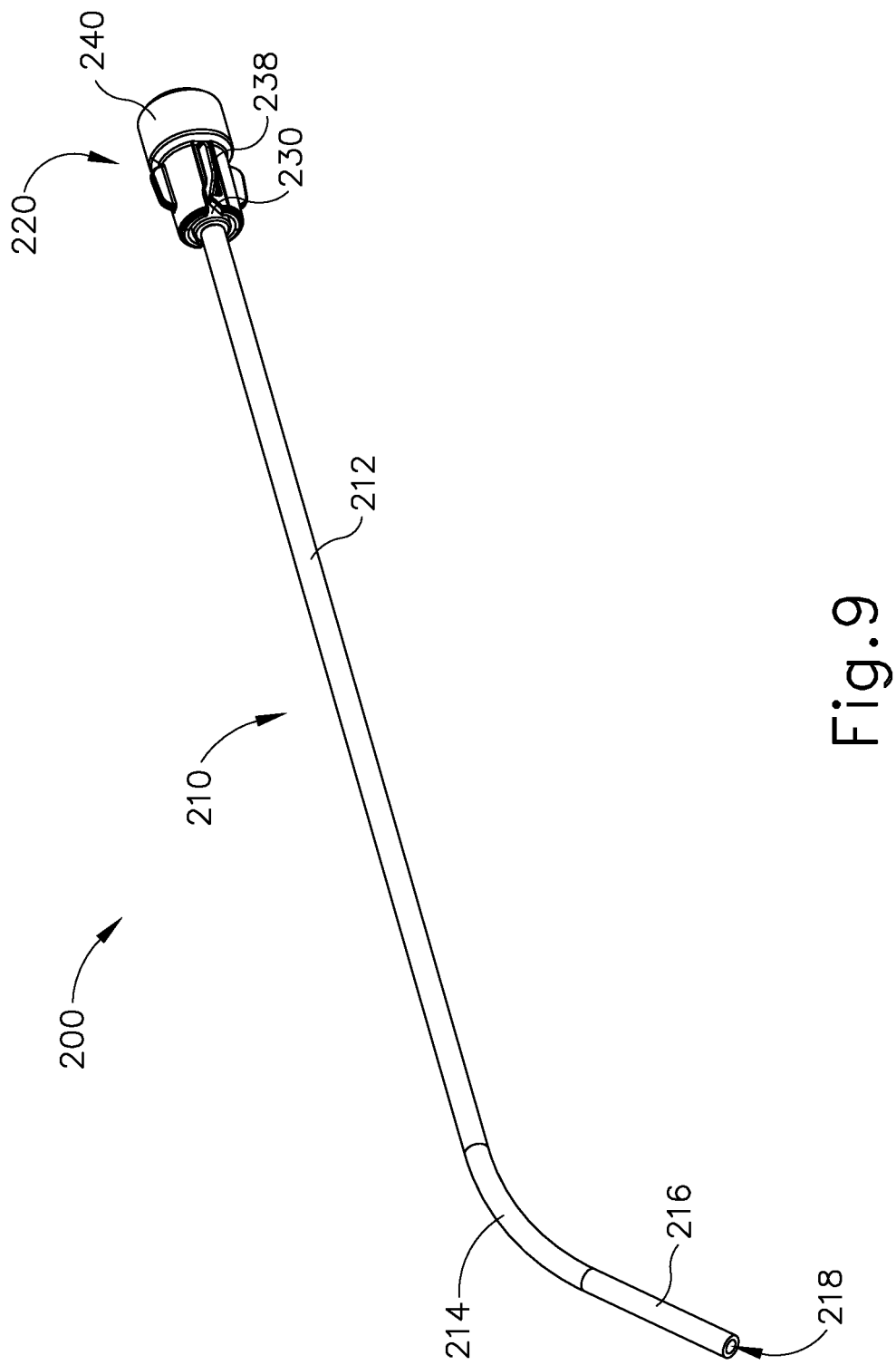
FIG. 9 depicts a perspective view of an exemplary irrigation catheter assembly suitable for use with the instrument of FIG. 4.

FIGS. 9-11 and 14A-15B show an exemplary irrigation catheter assembly (200) that may be used with instrument (100) or otherwise incorporated into dilation catheter system (10). By way of example only, a catheter (210) of irrigation catheter assembly (200) may be inserted through guide catheter (30, 104) in place of dilation catheter (20, 108). Irrigation catheter assembly (200) of this example includes a coupler assembly (220) at the proximal end of catheter (210). As shown in FIG. 9, irrigation catheter (210) of this example comprises a substantially straight proximal portion (212), a bend (214), a substantially straight distal portion (216), and a distal opening (218); with bend (214) positioned between portions (212, 216). It should be understood, however, that catheter (210) may have any other suitable configuration, including but not limited to a straight configuration. Moreover, catheter (210) may be flexible such that catheter (210) follows any curvature in the lumen of guide catheter (30, 104). Catheter (210) may also be constructed and operable in accordance with at least some of the teachings of U.S. Pub. No. 2008/0183128, entitled "Methods, Devices and Systems for Treatment and/or Diagnosis of Disorders of the Ear, Nose and Throat," published Jul. 31, 2008, now abandoned, the disclosure of which is incorporated by reference herein.

Figure 10A:
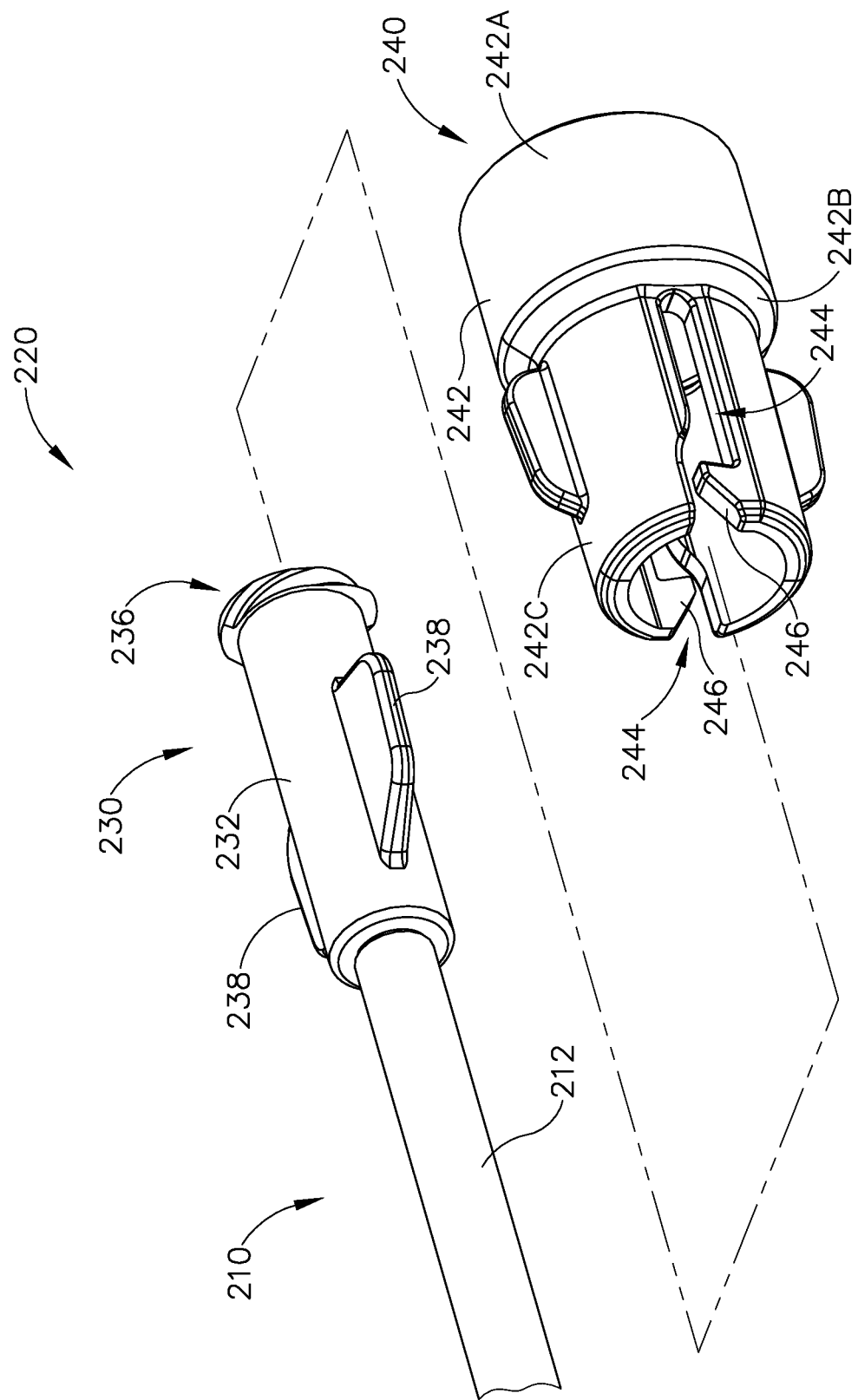
FIG. 10A depicts a partially exploded perspective view of the coupler assembly of FIG. 10.
Figure 11:
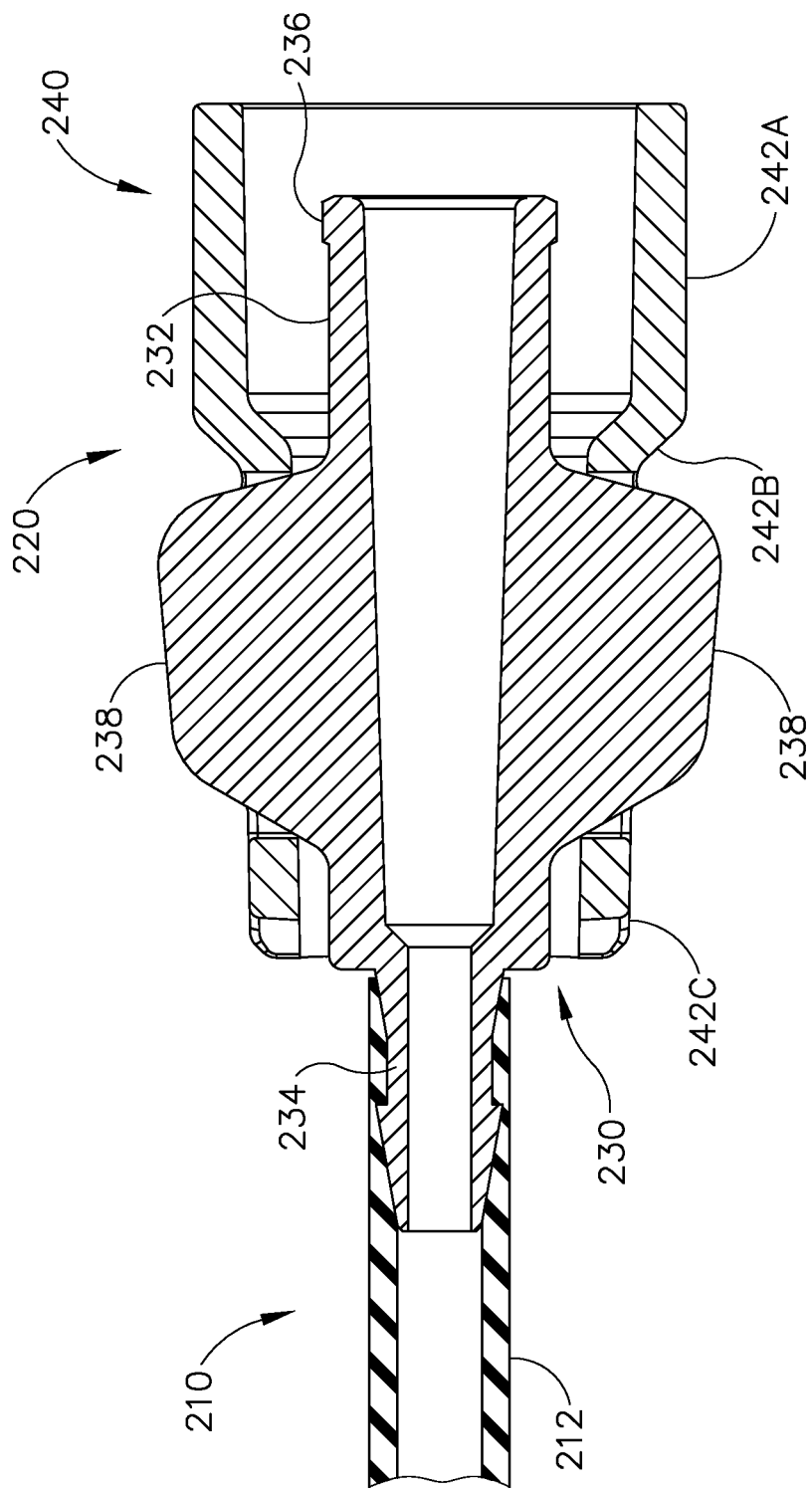
FIG. 11 depicts a cross-sectional side view of the coupler portion of the irrigation catheter assembly of FIG. 9.

Catheter (210) defines an inner lumen that provides a fluid pathway between coupler assembly (220) and distal opening (218). As best seen in FIGS. 10-11, coupler assembly (220) comprises a coupler (230) and a guard (240). Coupler (230) comprises a tubular body (232). Coupler (230) further comprises a hollow barb (234) extending distally from a distal end of body (232), a pair of fins (238) extending laterally from an exterior surface of body (232), and a thread (236) extending from the exterior surface of body (232) at a proximal end of body (232). Coupler (230) is thus configured like a conventional male luer fitting. A proximal end of irrigation catheter (210) is fitted onto barb (234) to thereby couple irrigation catheter (210) with coupler (230) and to thereby provide a fluid seal between coupler (230) and irrigation catheter (210).

Guard (240) comprises a body (242) having a rigid proximal cylindrical portion (242A), a distal cylindrical portion (242C), and a frusto-conical intermediate portion (242B). Proximal cylindrical portion (242A) defines a hollow cylindrical interior. Distal cylindrical portion (242C) also defines a hollow cylindrical interior. The hollow cylindrical interior of proximal cylindrical portion (242A) is larger than the hollow cylindrical interior of distal cylindrical portion (2342C). Frusto-conical intermediate portion (242B) defines a hollow frusto-conical interior that provides a transition between the hollow cylindrical interior of proximal cylindrical portion (242A) and the hollow cylindrical interior of distal cylindrical portion (242C).

Guard (240) is configured to receive coupler (230). In particular, distal cylindrical portion (242C) comprises a pair of slots (244) configured to receive fins (238) of coupler (230) in a snap-fit manner to thereby secure guard (240) to coupler (230). Slots (244) each comprise a ramp (246) that is formed in a distal portion of slots (244) and configured to engage fins (238) as coupler (230) is inserted proximally within guard (240). This engagement causes each half of distal cylindrical portion (242C) to flex outwardly to thereby open slots (244) such that fins (238) may be received within a proximal portion of slots (244). Once received within the proximal portions of slots (244), fins (238) no longer engage ramps (246) such that distal cylindrical portion (242C) returns to its initial shape to thereby cause slots (244) to snap closed; thereby coupling coupler (230) with guard (240).

Figure 12:
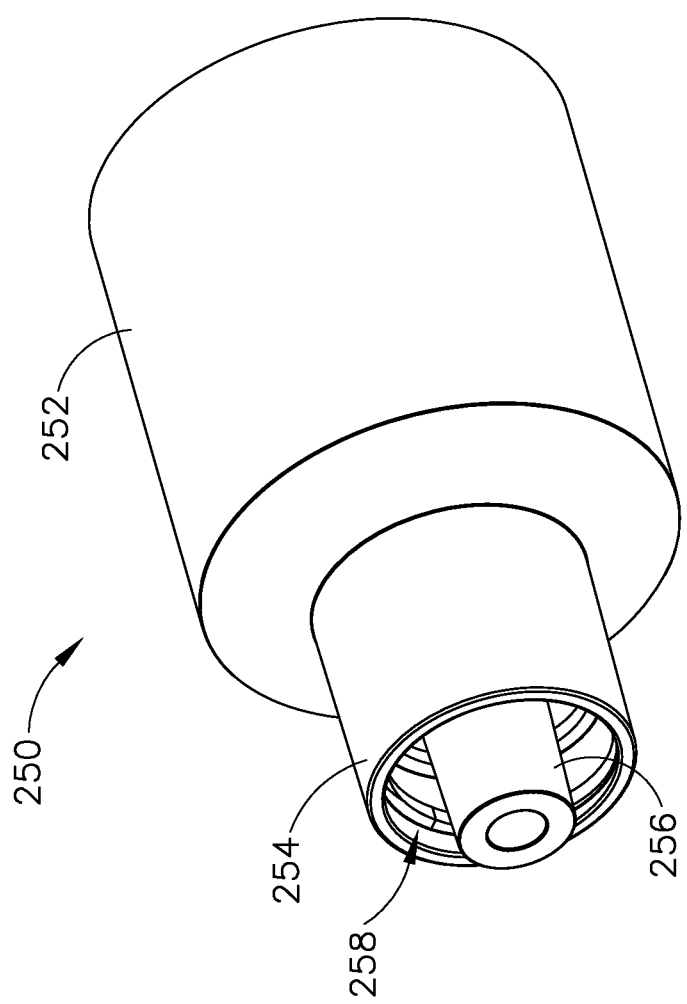
FIG. 12 depicts a perspective view of an irrigation syringe coupler.
Figure 14A:
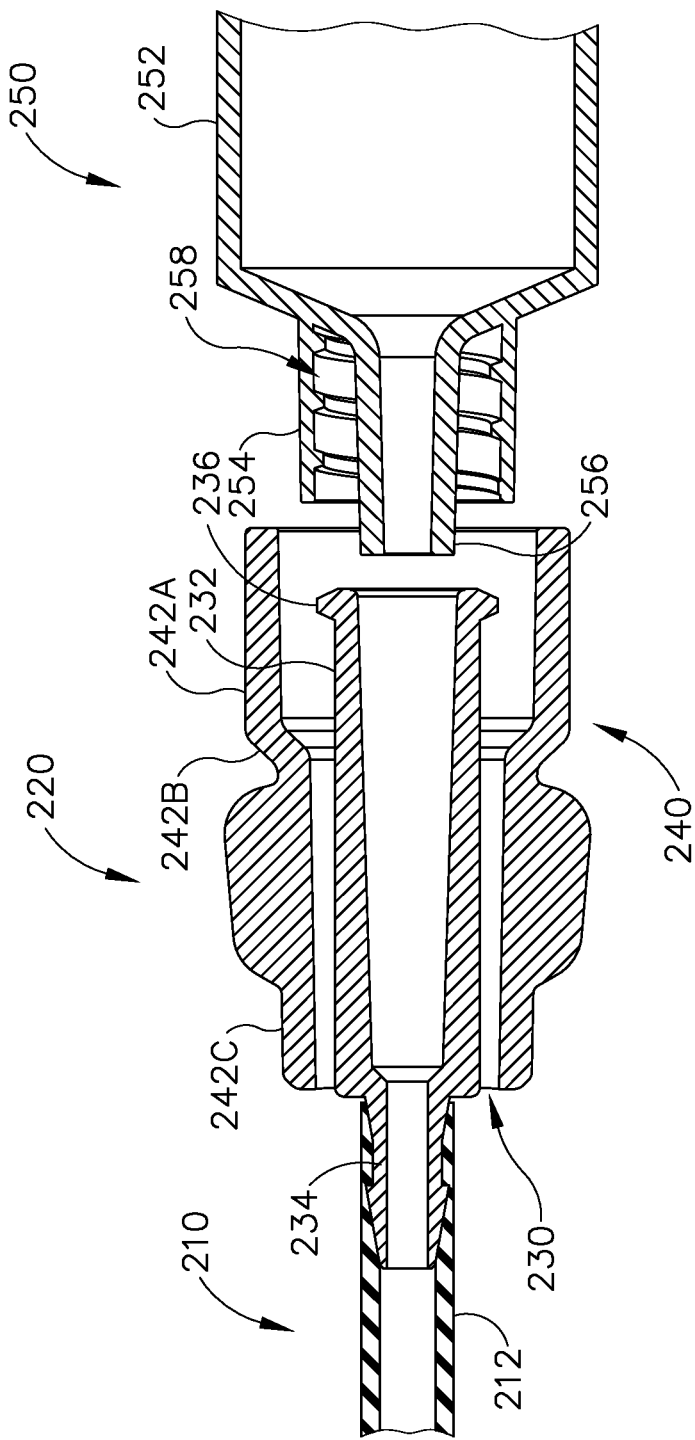
FIG. 14A depicts a cross-sectional side elevational view of the proximal end of the irrigation catheter assembly of FIG. 9 and the irrigation syringe coupler of FIG. 12, with the irrigation syringe coupler separated from the coupler assembly of the irrigation catheter assembly.
Figure 14B:
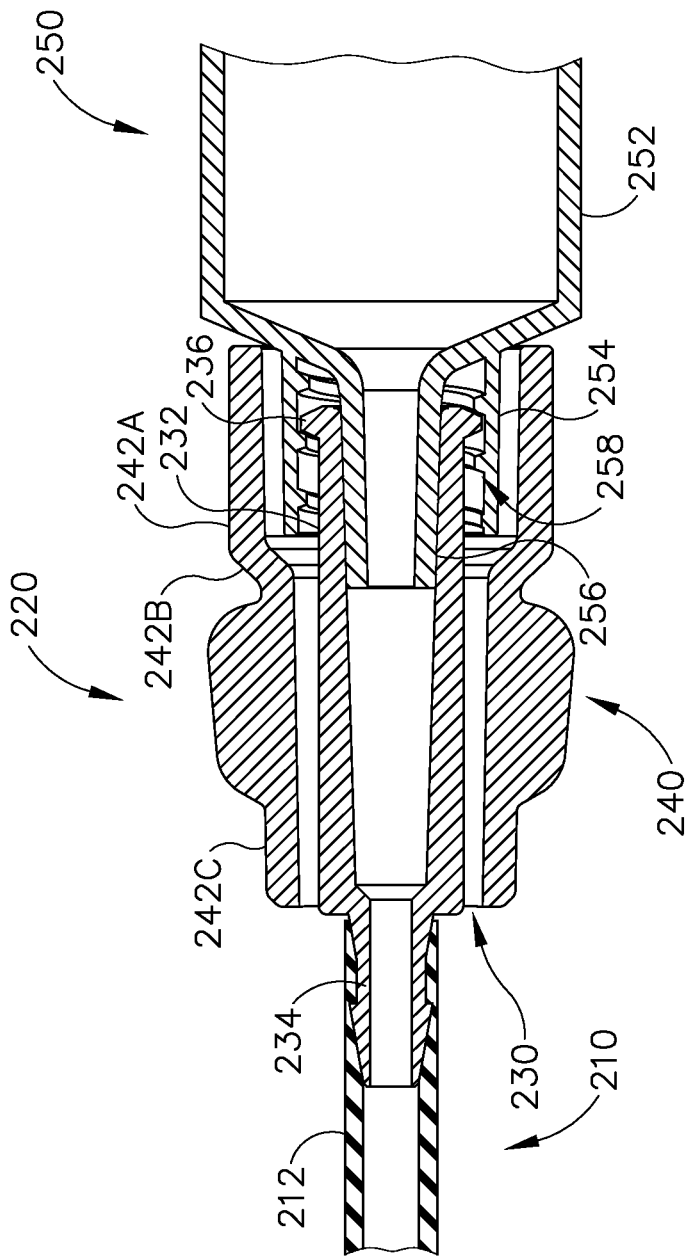
FIG. 14B depicts a cross-sectional side elevational view of the proximal end of the irrigation catheter assembly of FIG. 9 and the irrigation syringe coupler of FIG. 12, with the irrigation syringe coupler coupled to the coupler assembly of the irrigation catheter assembly.

FIGS. 12 and 14A-14B show an exemplary irrigation luer fitting (250). In some versions, irrigation luer fitting (250) comprises a conventional female luer syringe fitting or is integrated into the tip of an irrigation syringe. Irrigation luer fitting (250) is configured to couple with coupler assembly (220) to thereby provide irrigation fluid to irrigation catheter (210). Irrigation luer fitting (250) comprises a cylindrical body (252) having a hollow cylindrical member (254) extending distally from a distal end of body (252), with a tube (256) extending therethrough. Cylindrical member (254) comprises a threading (258) extending inwardly from an interior surface of cylindrical member (254). As shown in FIGS. 14A and 14B, coupler assembly (220) is configured to receive and couple with irrigation luer fitting (250). Upon insertion of irrigation luer fitting (250) within a proximal end of coupler assembly (220) between guard (240) and coupler (230), cylindrical member (254) is configured to thread about tubular body (232) of coupler (230) thereby coupling irrigation luer fitting (250) with coupler assembly (220) and irrigation catheter assembly (200). Cylindrical member (254) is thus sized for receipt within the hollow interior of proximal cylindrical portion (242A). Furthermore, tube (256) is configured to be received within tubular body (232) and engage an interior surface of tubular body (232) of coupler (230) to thereby provide a fluid seal therebetween.

Figure 13:
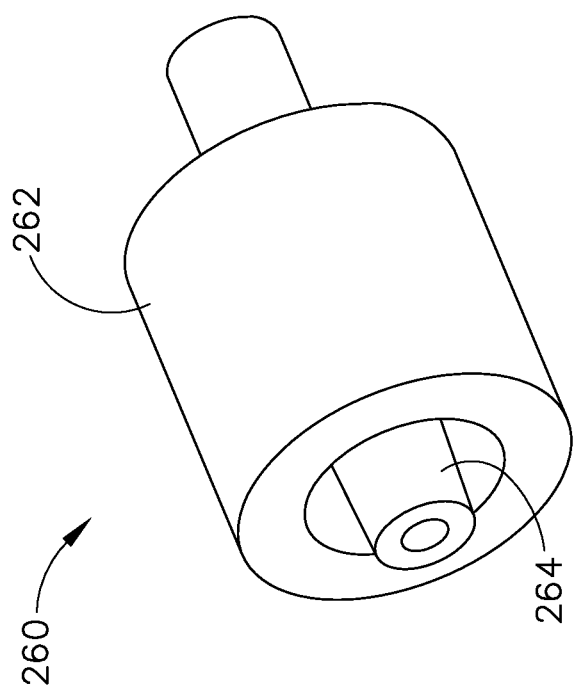
FIG. 13 depicts a perspective view of an inflation coupler.
Figure 15B:
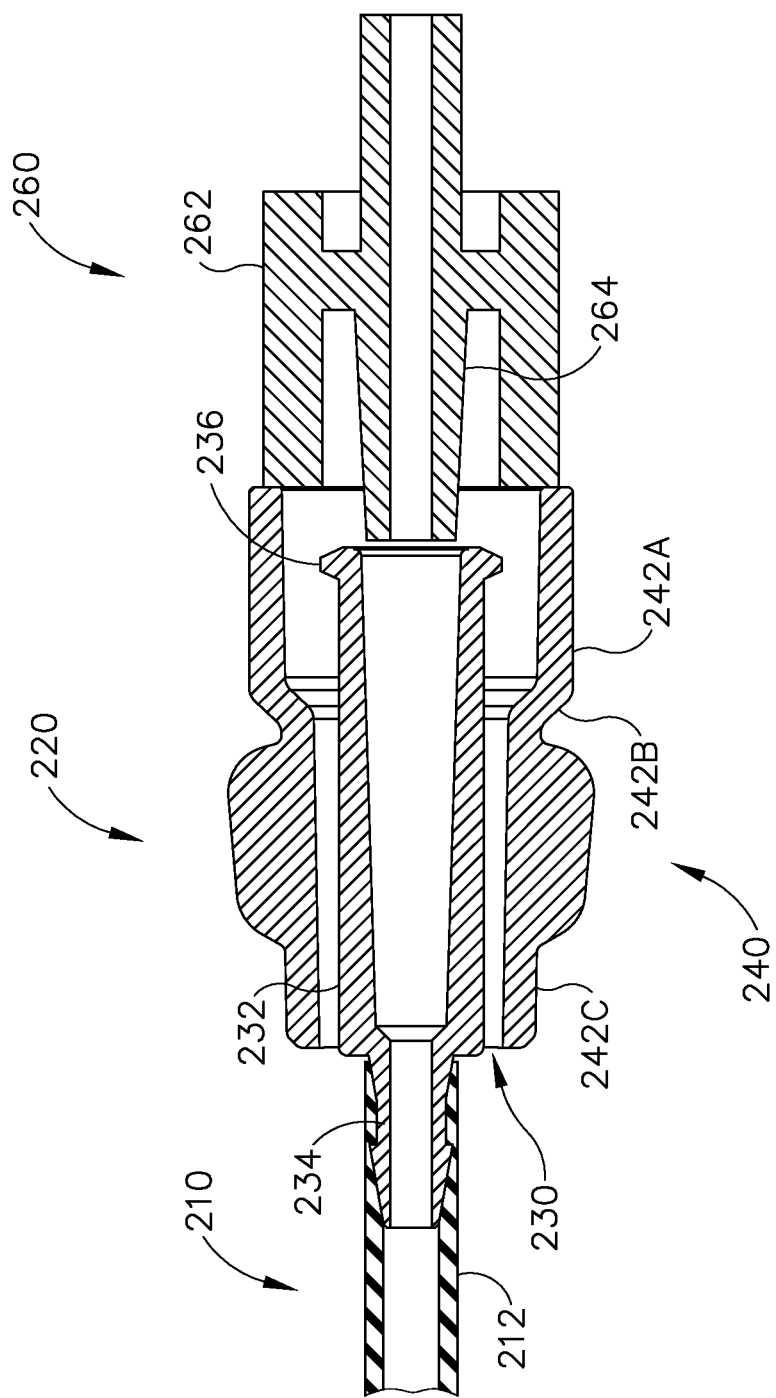
FIG. 15B depicts a cross-sectional side elevational view of the proximal end of the irrigation catheter assembly of FIG. 9 and the inflation coupler of FIG. 13, with the inflation coupler moved toward but unable to couple with the coupler assembly of the irrigation catheter assembly.
Figure 16:
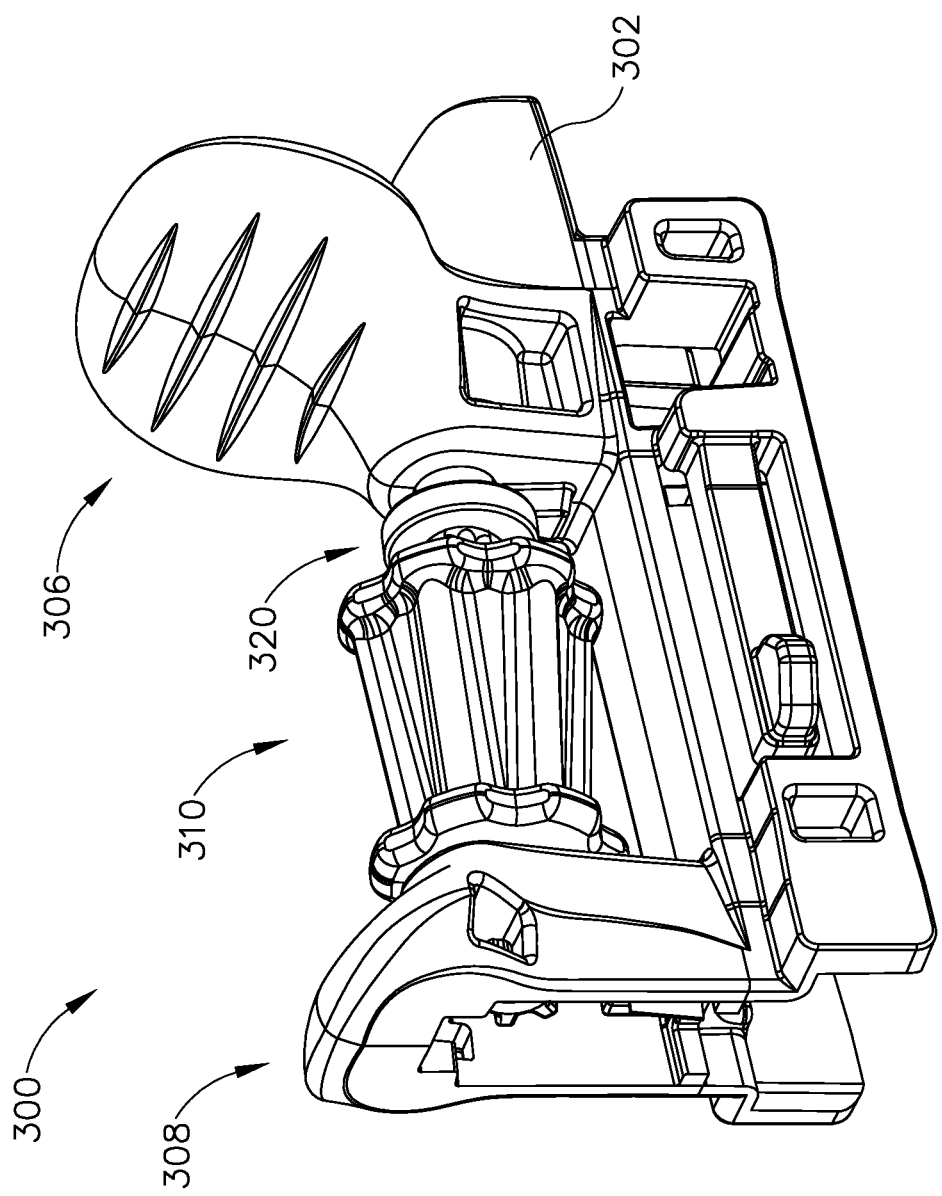
FIG. 16 depicts a perspective view of an exemplary guidewire movement mechanism that may be incorporated into the instrument of FIG. 4.
Figure 17:
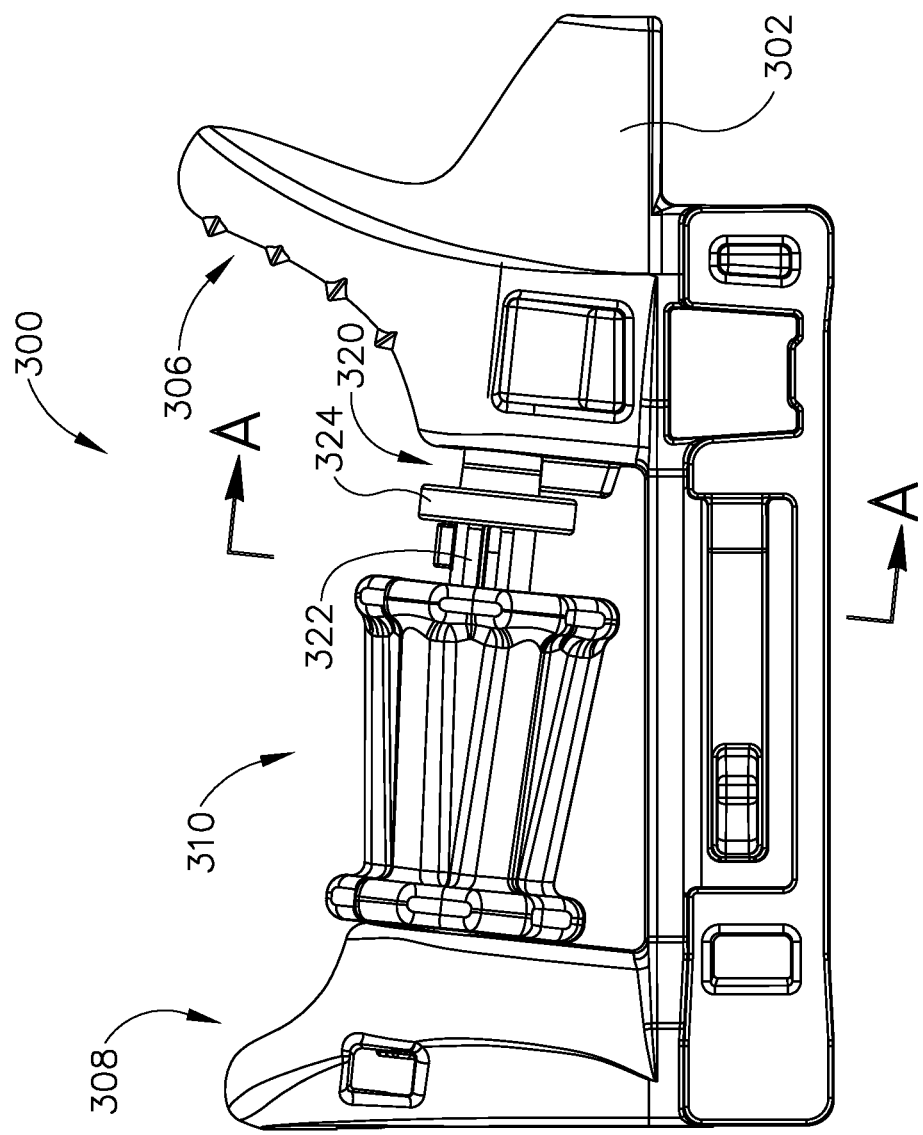
FIG. 17 depicts a side elevational view of the guidewire movement mechanism of FIG. 16.

FIGS. 13 and 15A-15B depict an exemplary inflation luer fitting (260). Inflation luer fitting (260) is configured to couple with port (26, 111) to thereby provide pressurized fluid to dilation catheter (20, 108). Inflation luer fitting (260) comprises a cylindrical body (262) with a tube (264) extending distally therefrom. In some versions, cylindrical body (262) may include an internal threading, similar to threading (258). In the present example, the outer diameter of cylindrical body (262) is larger than the inner diameter of proximal cylindrical portion (242A). As shown in FIGS. 15A and 15B, as luer fitting (260) is moved toward the proximal end of coupler assembly (220), a distal face of cylindrical body (262) engages a proximal face of proximal cylindrical portion (242A) to thereby prevent coupling of inflation luer fitting (260) to coupler assembly (220) and insertion of tube (264) within tubular body (232). Inflation luer fitting (260) is thus unable to provide pressurized fluid to irrigation catheter assembly (200).

It should be understood from the foregoing that coupler assembly (220) may physically prevent a source of inflation fluid from being coupled with a catheter (210) that is intended for irrigation. It should also be understood that coupler assembly may be opaque to aid in identification, be clear or translucent to aid in visualization of thread (236) during connection, or have any other suitable properties. In addition, while coupler assembly (220) of this example comprises a guard (240) that is snapped onto a coupler (230), in other versions guard (240) may be formed unitarily with coupler (230) (e.g., molded together as a single component).

IV. Exemplary Guidewire Movement Mechanism with Rotation Limitation Feature

As noted above, knob (134) of guidewire movement mechanism (112) is operable to rotate guidewire (106) about the longitudinal axis of guidewire (106). In some versions of instrument (100), guidewire (106) may be rotated through a virtually infinite number of revolutions. This may damage some versions of guidewire (106), such as versions of guidewire (106) having light fibers that may become damage if twisted too many times. It may therefore be beneficial to restrict the degree to which guidewire (106) may be rotated about the longitudinal axis of guidewire (106). In addition to reducing the risk of damage to guidewire (106) that might otherwise occur due to over-rotation, restricting the degree to which guidewire (106) may be rotated about the longitudinal axis of guidewire (106) may provide the operator with a tactile reference point to indicate when guidewire (106) has spun at least once around.

FIGS. 16-20E show one merely illustrative example of a guidewire movement mechanism (300) that is configured to restrict the degree to which guidewire (106) may be rotated about the longitudinal axis of guidewire (106). Guidewire movement mechanism (300) may be used as a substitute for guidewire movement mechanism (112), such that guidewire movement mechanism (112) may be readily incorporated into instrument (100). Guidewire movement mechanism (300) is configured to operate substantially similar to guidewire movement mechanism (112) discussed above except for the differences discussed below. In particular, guidewire movement mechanism (300) is operable to longitudinally advance and retract guidewire (106) relative to handle (102), through guidewire support (118), and through the second lumen of dilation catheter (108) by longitudinally sliding guidewire movement mechanism (300) along the length of handle (102). To facilitate such movement of guidewire movement mechanism (300), the distal end of the body (302) of guidewire movement mechanism (300) includes a raised pommel portion (306) and the proximal end of body (302) includes a raised cantle portion (308). Pommel and cantle portions (306, 308) are configured to receive and engage an operator's finger and thereby provide surfaces for the operator's finger to bear against to drive guidewire movement mechanism (300) distally and proximally relative to handle (102).

Guidewire movement mechanism (300) also includes a rotation knob (310). Rotation knob (310) is positioned between pommel and cantle portions (306, 308) and is rotatably supported by body (302). Rotation knob (310) is secured to guidewire (106) such that knob (310) is operable to rotate guidewire (106) about the longitudinal axis of guidewire (106), similar to knob (134) described above. However, unlike guidewire movement mechanism (112) described above, guidewire movement mechanism (300) of the present example comprises a guidewire rotation limiting assembly (320).

Figure 18:
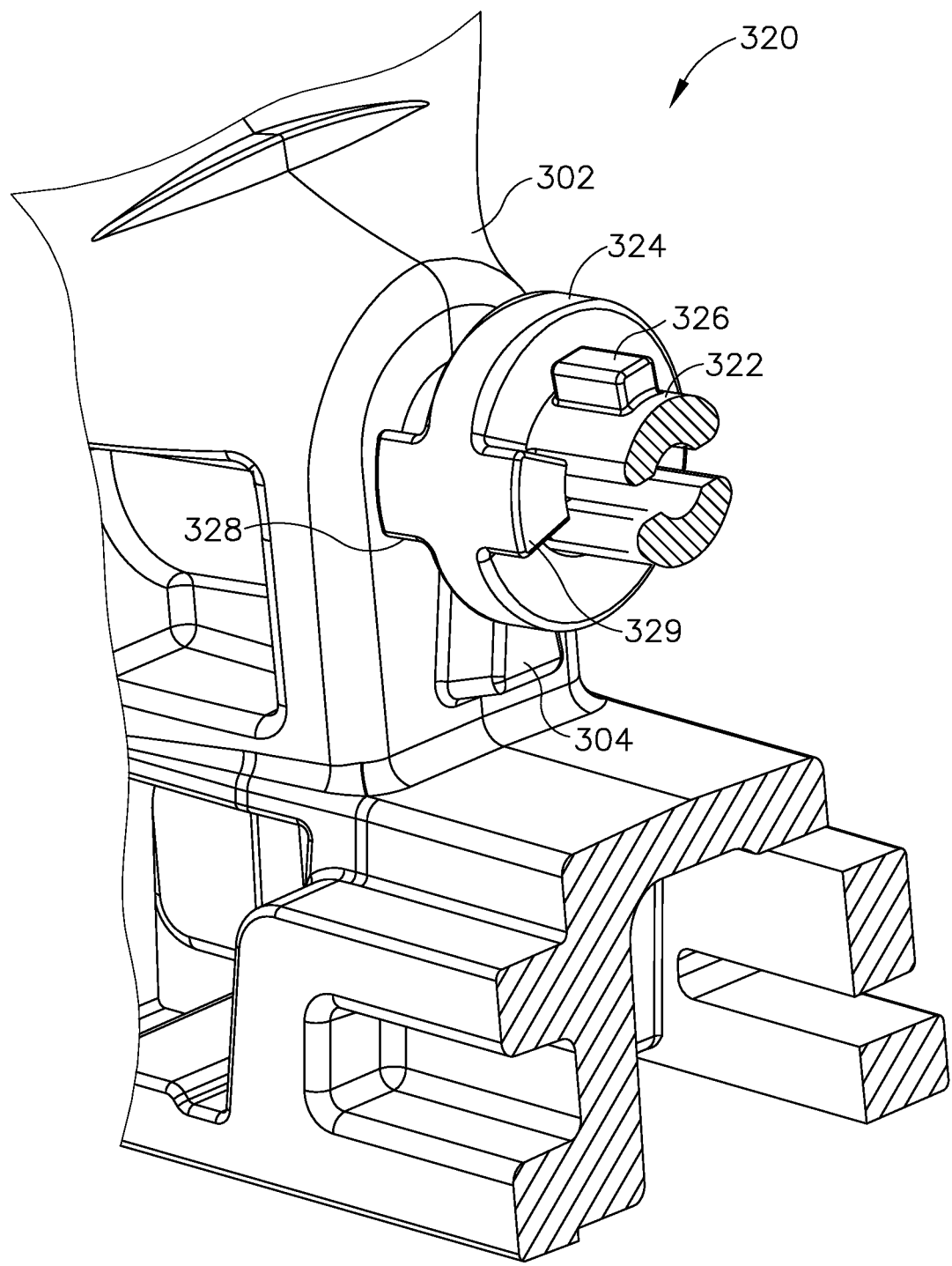
FIG. 18 depicts a cross-sectional perspective view of the guidewire movement mechanism of FIG. 16, taken along line A-A of FIG. 17.
Figure 19:
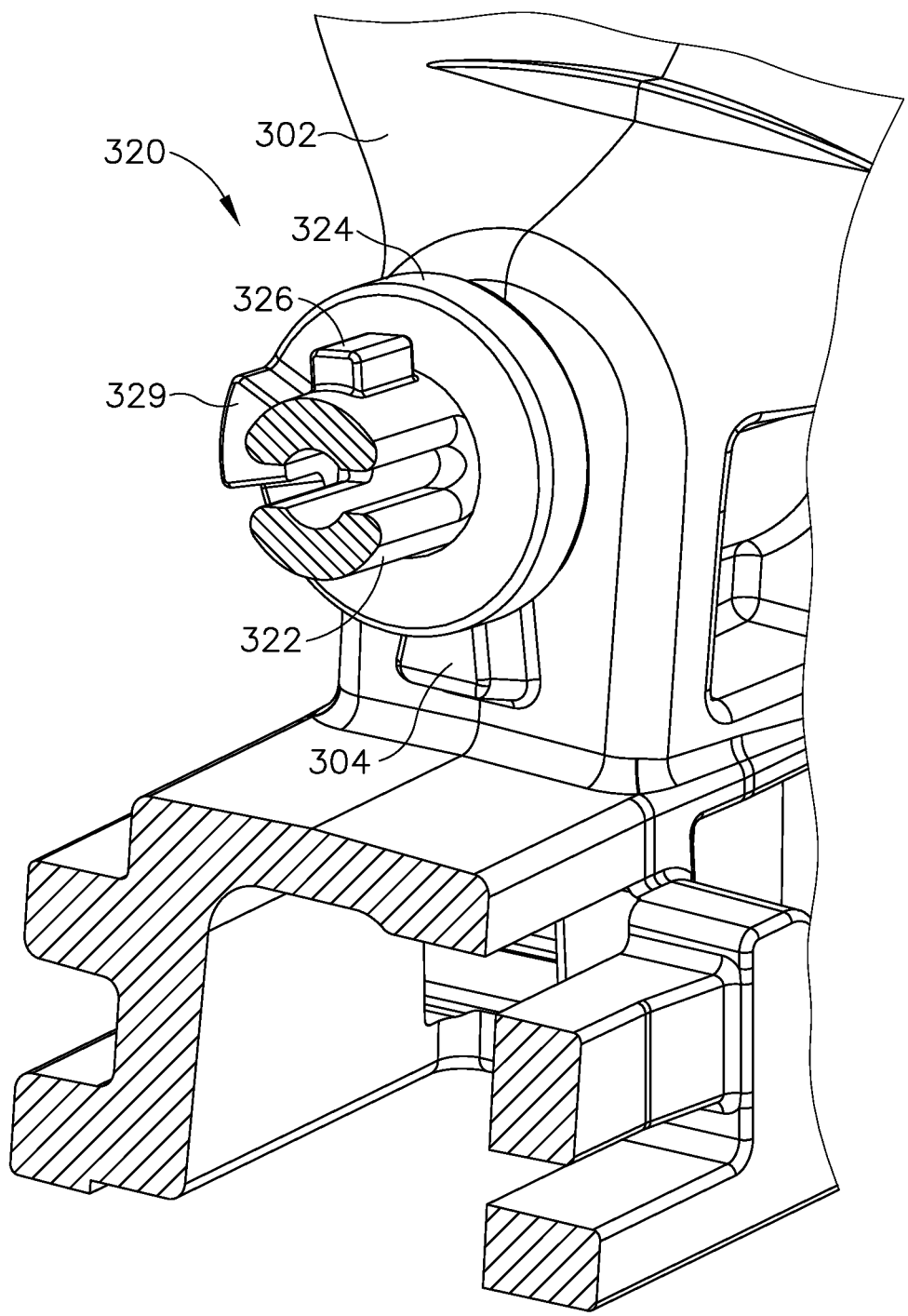
FIG. 19 depicts another cross-sectional perspective view of the guidewire movement mechanism of FIG. 16, taken along line A-A of FIG. 17.

As best seen in FIGS. 18 and 19, rotation limiting assembly (320) comprises a first member (322) and a second member (324). First member (322) is a unitarily integral feature of rotation knob (310) and is positioned at the distal end of rotation knob (310). First member (322) is thus rotatably supported by body (302) such that first member (322) is operable to rotate, unitarily with the rest of rotation knob (310), relative to body (302). It should be understood that, as a unitary feature of rotation knob (310), first member (322) rotates unitarily with guidewire (106). Second member (324) is rotatably disposed about first member (322) such that first member (322) and second member (324) are operable to rotate independently of one another through a certain angular range of motion.

First member (322) comprises a projection (326) extending radially outwardly from an exterior surface of first member (322), adjacent to a proximal face of second member (324). Second member (324) comprises a distal projection (328) extending distally from a distal face of second member (324); and a proximal projection (329) extending proximally from a proximal face of second member (324). Projections (328, 329) are located at the same angular position about the longitudinal axis passing through the radial center of second member (324) in this example. In some other versions, projections (328, 329) may be angularly offset from each other about the longitudinal axis passing through the radial center of second member (324). Body (302) of guidewire movement mechanism (300) comprises a projection (304) extending proximally from a proximal face of body (302). Projection (304) is a unitarily integral feature of body (302) such that projection (304) serves as a hard stop. As will be discussed in more detail below, projections (304, 326, 328, 329) are configured to engage one another during rotation of first member (322) and second member (324) to thereby limit rotation of guidewire (106).

Figure 20A:
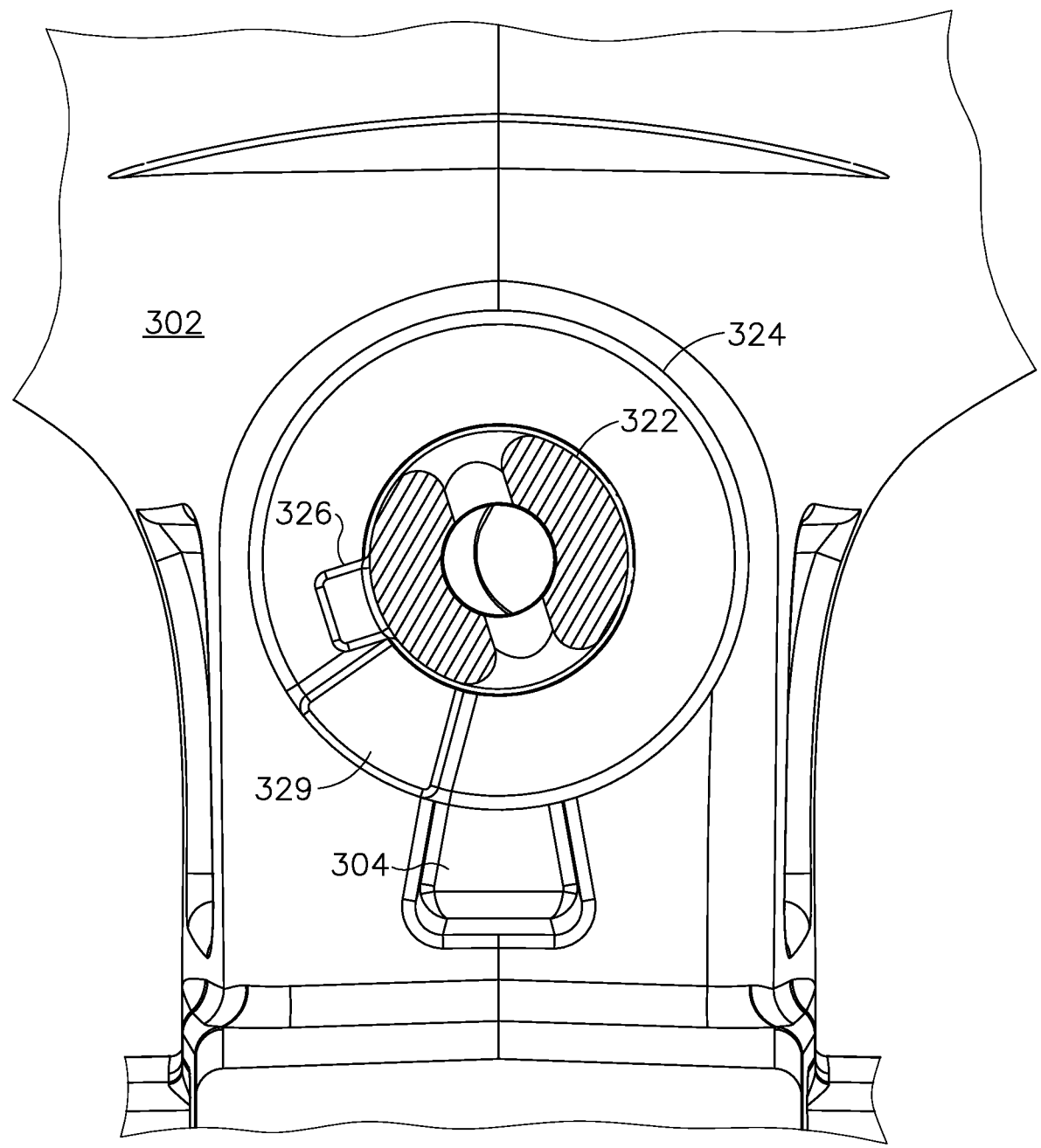
FIG. 20A depicts a cross-sectional rear elevational view of the guidewire movement mechanism of FIG. 16, taken along line A-A of FIG. 17, with the guidewire in a first rotational position, with a first rotary member in a first rotational position, and with a second rotary member in a first rotational position.
Figure 20B:
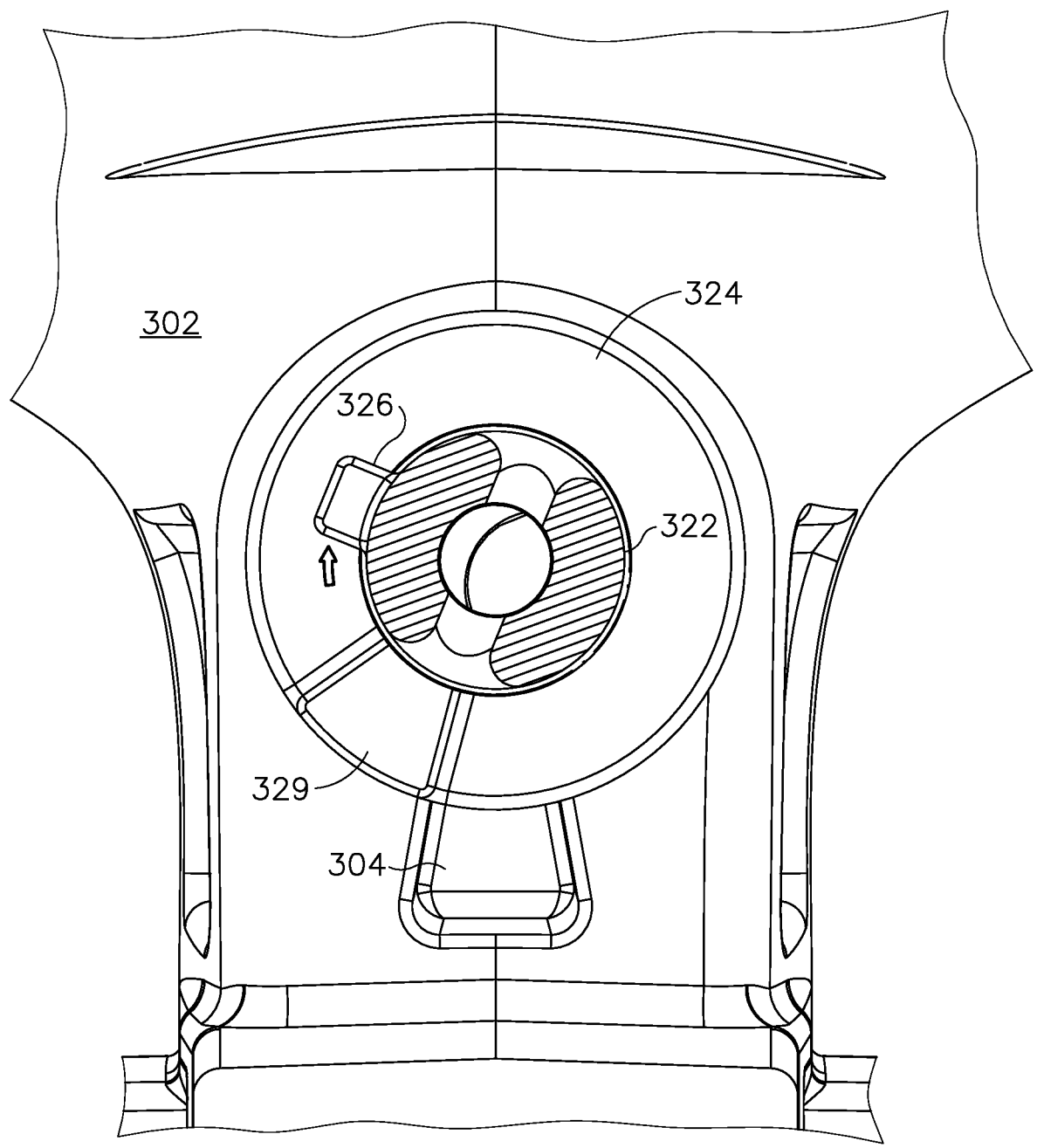
FIG. 20B depicts a cross-sectional rear elevational view of the guidewire movement mechanism of FIG. 16, taken along line A-A of FIG. 17, with the guidewire rotated into a second rotational position by rotation of the first rotary member into a second rotational position, and with the second rotary member remaining in the first rotational position.

FIGS. 20A-20E show an exemplary sequence of rotation of guidewire (106) about the longitudinal axis of guidewire (106). While guidewire (106) is not shown in FIGS. 20A-20E, it should be understood that guidewire (106) is coaxially disposed along the central longitudinal axis that is shared by members (322, 324). FIG. 20A shows rotation limiting assembly (320) in a counter-clockwise-most rotational position. In this position, projection (326) of first member (322) is engaged with a first surface of proximal projection (329) of second member (324), and distal projection (328) is also engaged with a first surface of projection (304) of body (302) such that guidewire (106) is unable to be rotated counter-clockwise any further. FIG. 20B shows first member (322) rotated clockwise, independently of second member (324), through a first range of angular motion such that projection (326) is no longer engaged with proximal projection (329) and such that guidewire (106) is also rotated clockwise. At this stage, second member (324) has not rotated, such that first member (322) has rotated relative to second member (324) in addition to rotating relative to body (302).

Figure 20C:
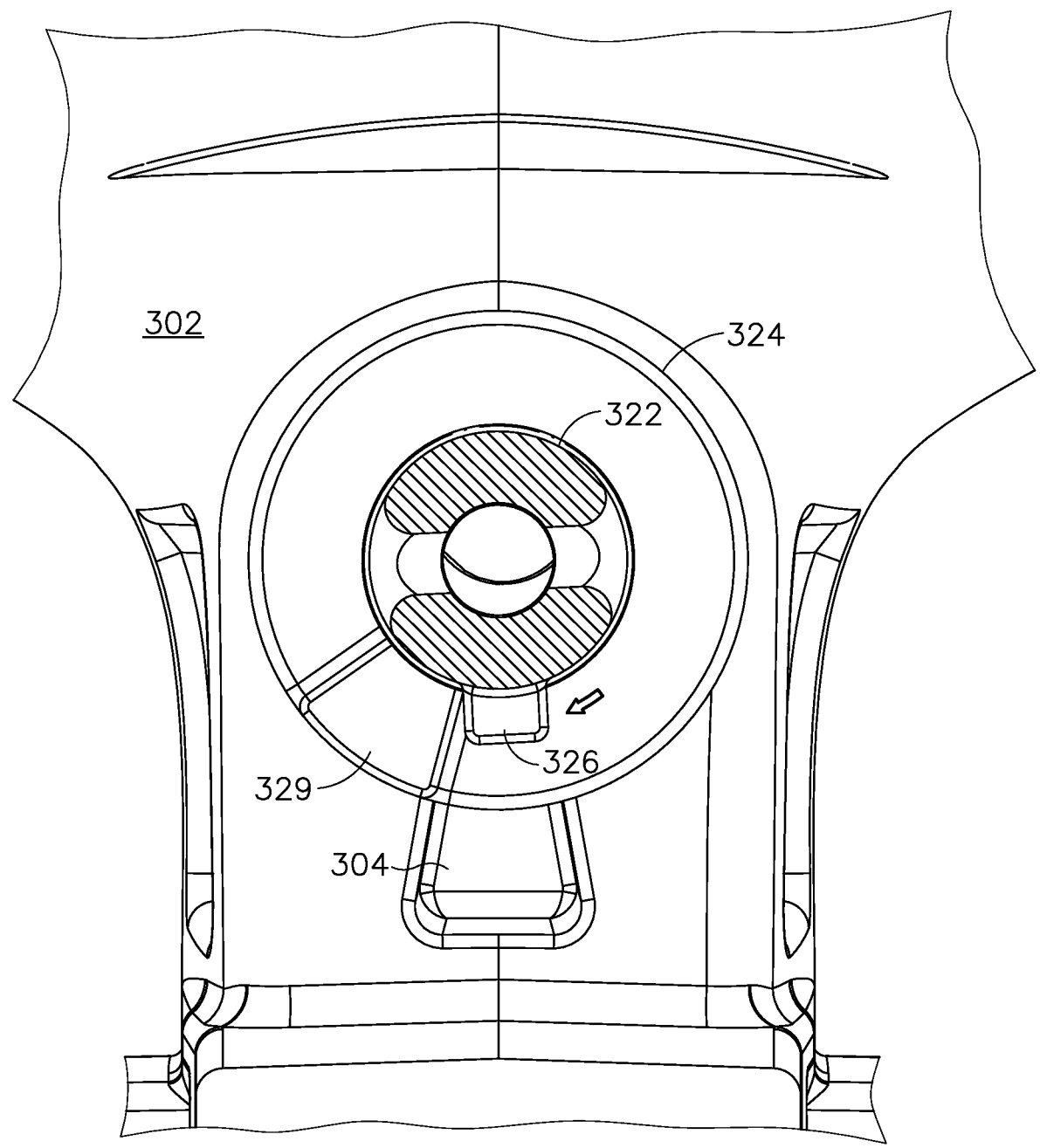
FIG. 20C depicts a cross-sectional rear elevational view of the guidewire movement mechanism of FIG. 16, taken along line A-A of FIG. 17, with the guidewire rotated into a third rotational position by rotation of the first rotary member into a third rotational position, and with the second rotary member remaining in the first rotational position.

FIG. 20C shows first member (322) rotated further clockwise, independently of second member (324), through a second range of angular motion such that projection (326) engages a second surface of proximal projection (329) and such that guidewire (106) is also further rotated clockwise.

Figure 20D:
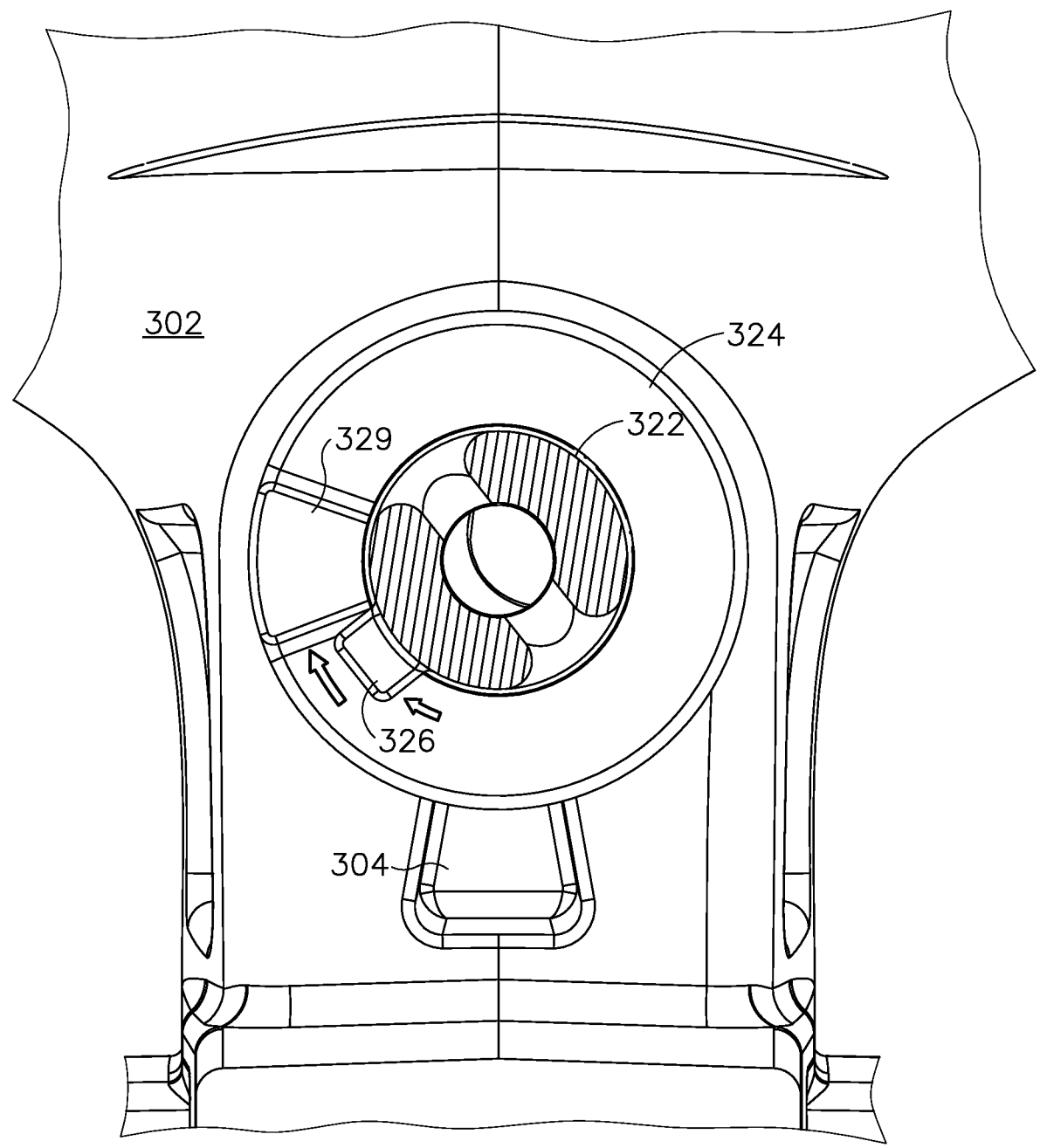
FIG. 20D depicts a cross-sectional rear elevational view of the guidewire movement mechanism of FIG. 16, taken along line A-A of FIG. 17, with the guidewire rotated into a fourth rotational position by rotation of the first rotary member into a fourth rotational position, and with the second rotary member rotated into a second rotational position.

At this stage, second member (324) has still not yet rotated, such that first member (322) has rotated relative to second member (324) in addition to rotating relative to body (302). FIG. 20D shows first member (322) rotated further clockwise through a third range of angular motion such that guidewire (106) is also further rotated clockwise. During the transition from the stage shown in FIG. 20C to the stage shown in FIG. 20D, first member (322) and second member (324) have rotated clockwise together due to engagement between projection (326) and proximal projection (329). In other words, first member (322) has driven second member (324) via projections (326, 329).

Figure 20E:
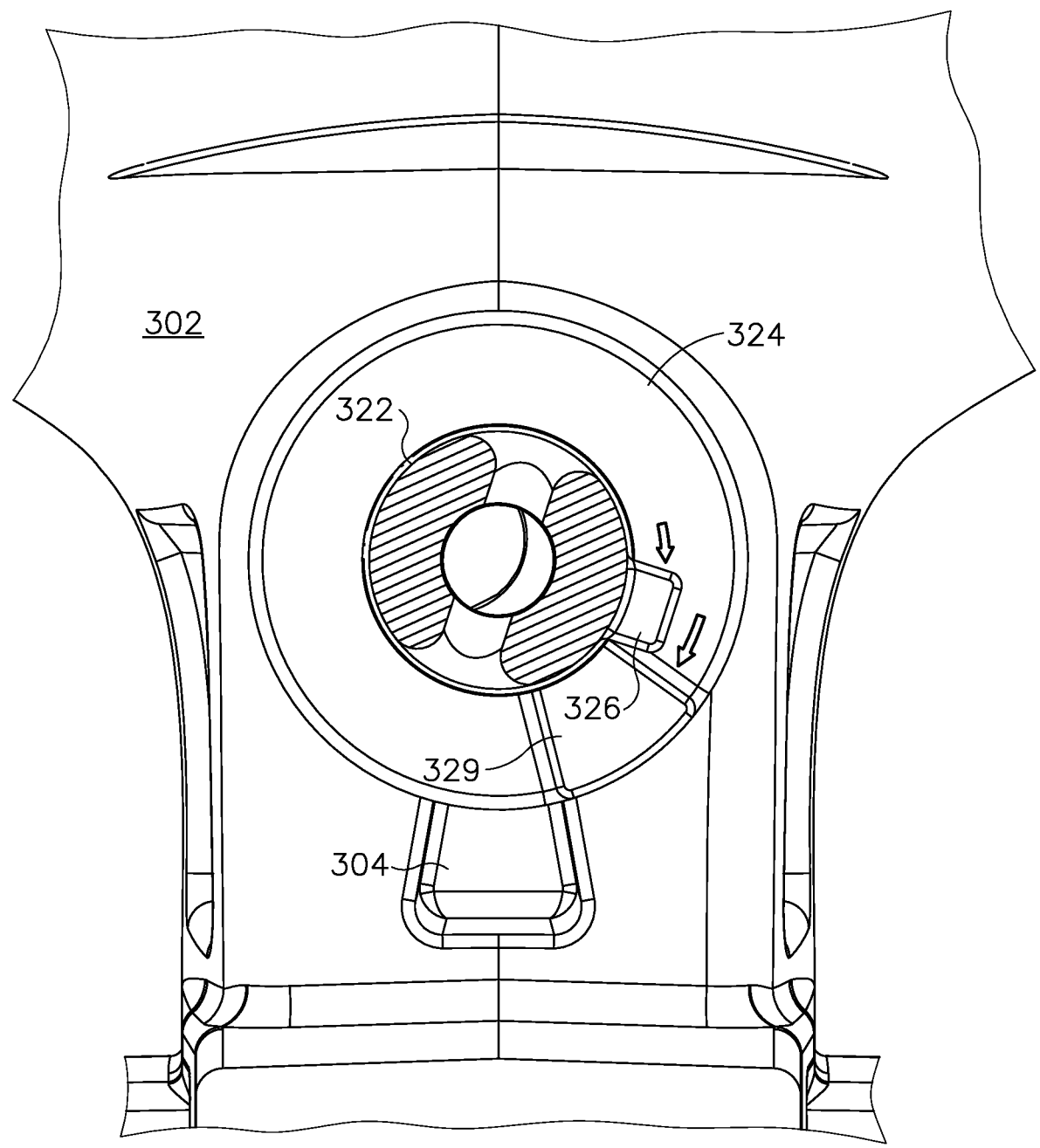
FIG. 20E depicts a cross-sectional rear elevational view of the guidewire movement mechanism of FIG. 16, taken along line A-A of FIG. 17, with the guidewire rotated into a fifth rotational position by rotation of the first rotary member into a fifth rotational position, and with the second rotary member rotated into a third rotational position.
Figure 21:
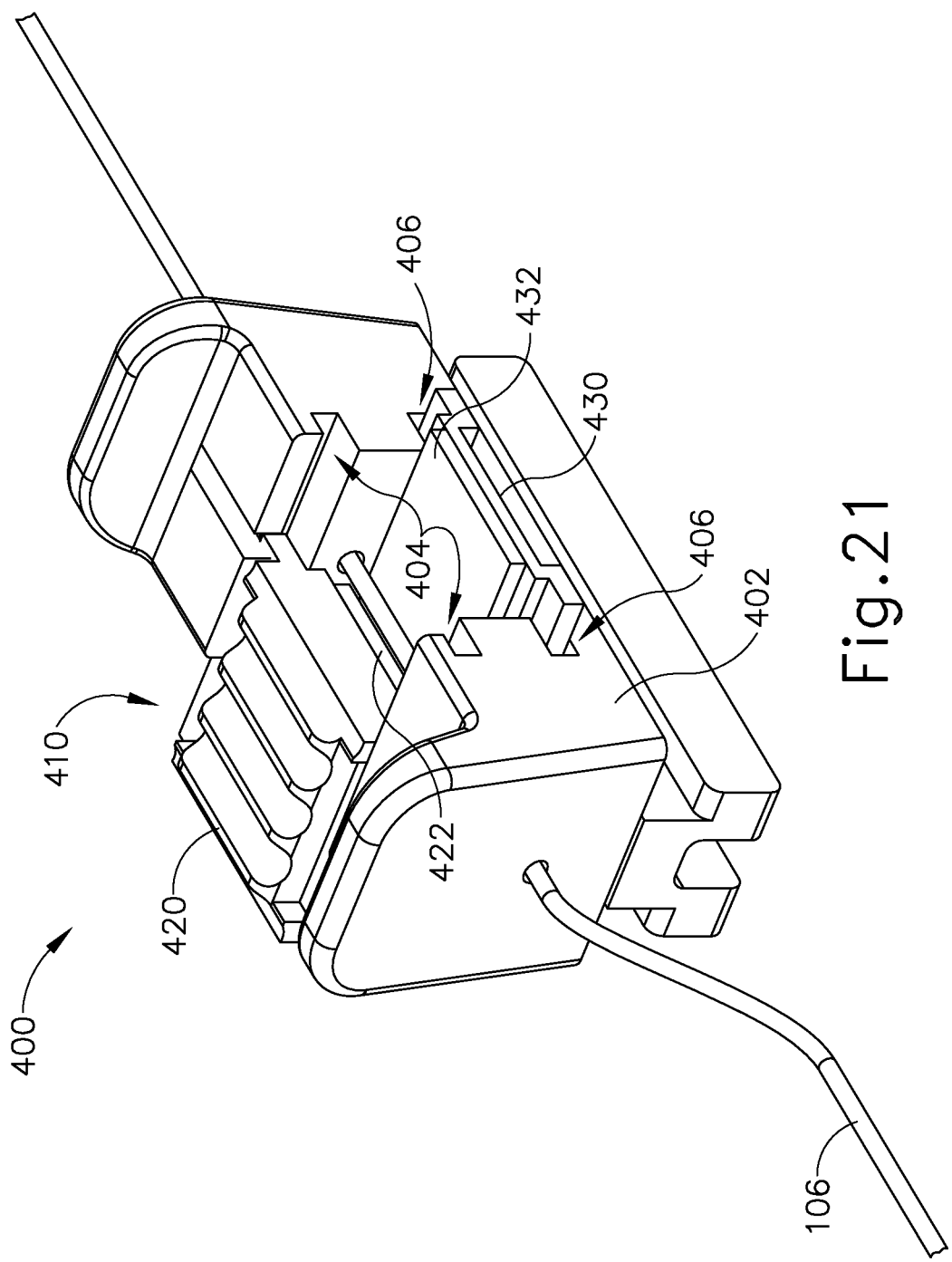
FIG. 21 depicts a perspective view of another exemplary guidewire movement mechanism that may be incorporated into the instrument of FIG. 4.
Figure 22:
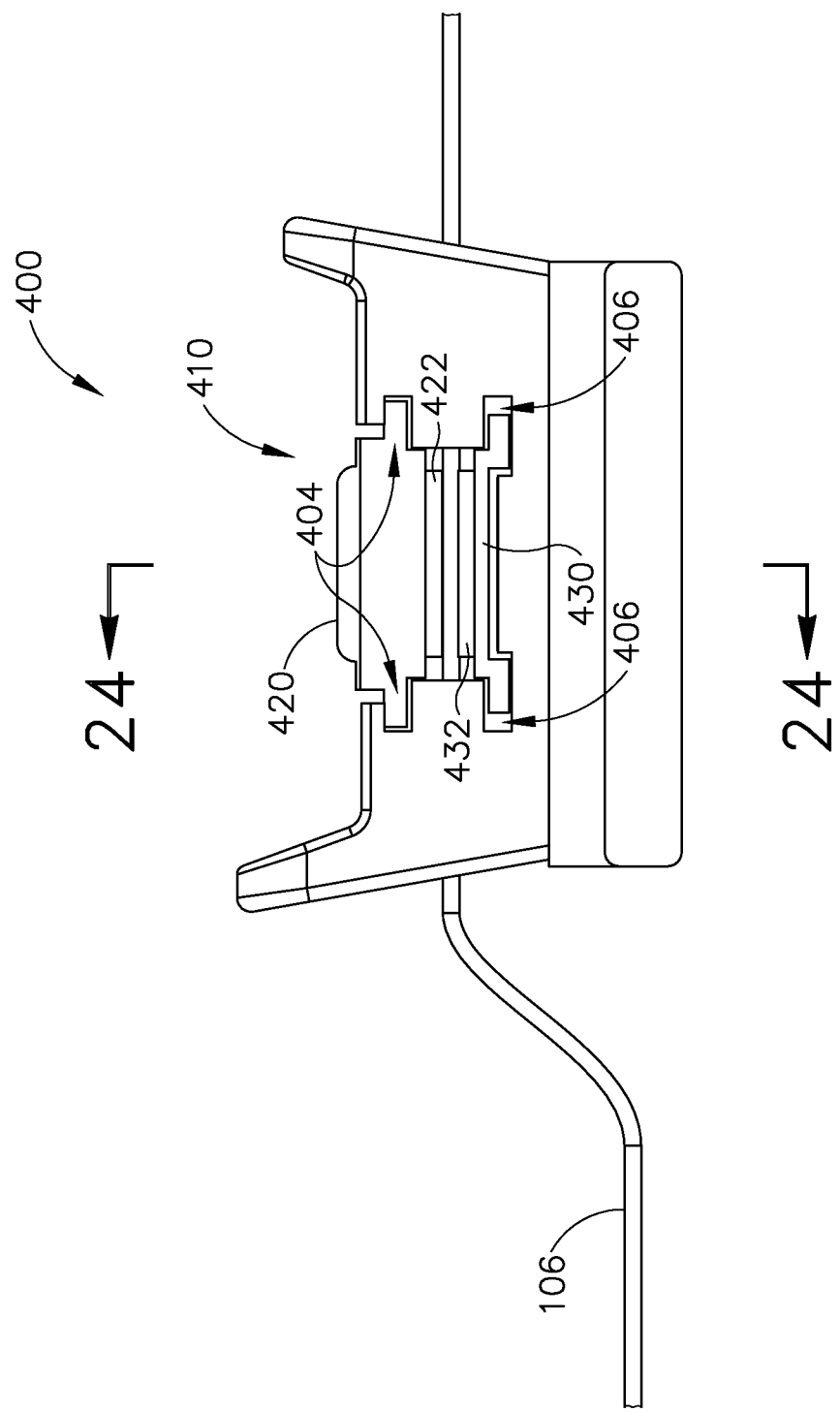
FIG. 22 depicts a side elevational view of the guidewire movement mechanism of FIG. 21.
Figure 23:
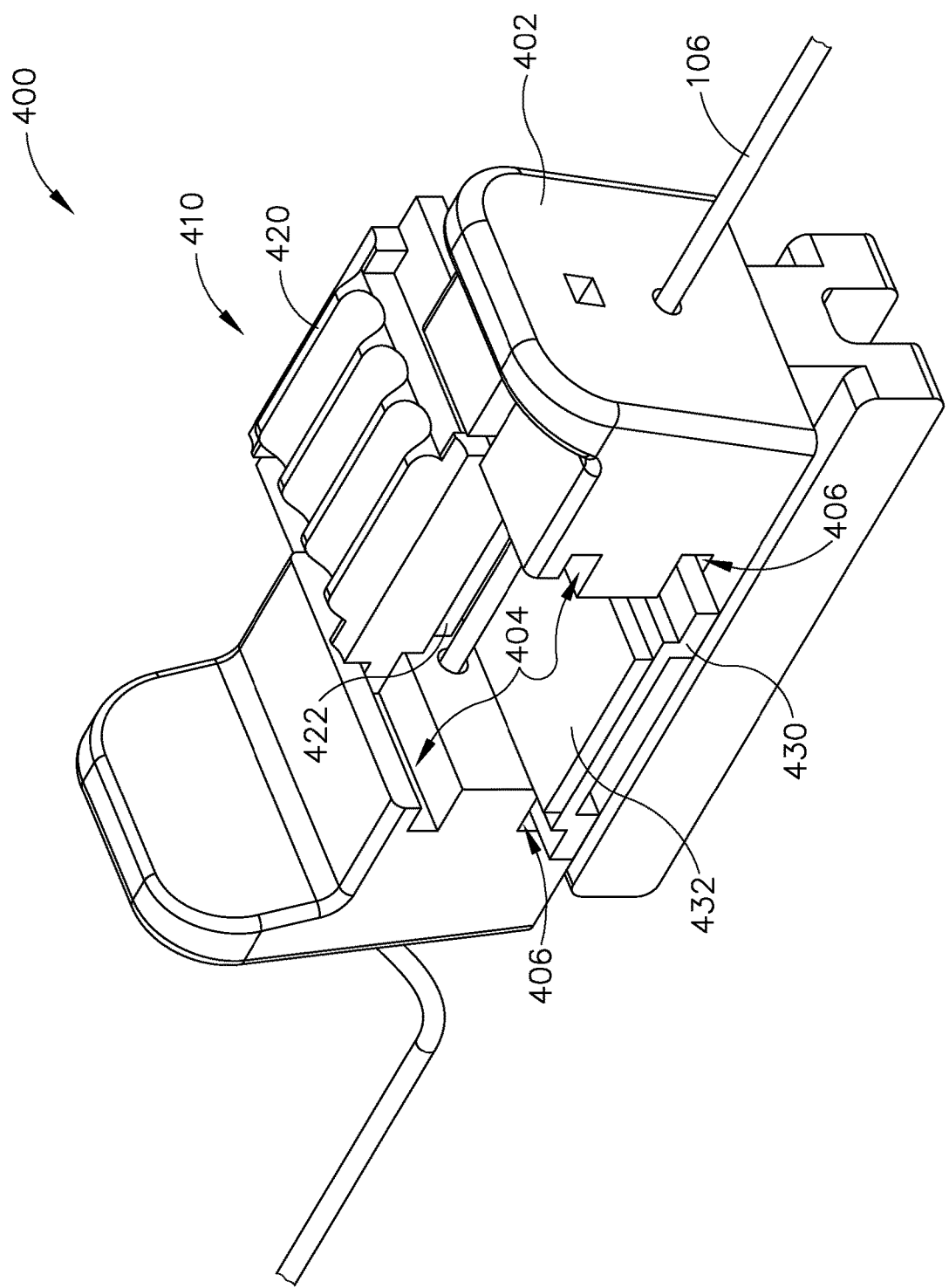
FIG. 23 depicts a perspective view of the guidewire movement mechanism of FIG. 21.

FIG. 20E shows first member (322) and second member (324) rotated further clockwise together due to engagement between projections (326, 329) into a clockwise-most position such that distal projection (328) engages a second surface of projection (304) of body (302) and such that guidewire (106) is also further rotated clockwise. At this stage, projection (304) serves as a hard stop preventing second member (324), first member (322), and guidewire (106) is from being rotated further clockwise. However, guidewire (106) may be rotated counter-clockwise back to the position shown in FIG. 20A. During such counter-clockwise rotation, first member (322) and guidewire (106) will rotate relative to body (302) and relative to second member (324) through a first range of angular motion until projection (326) engages proximal projection (329). As first member (322) and guidewire (106) continue to rotate counter-clockwise through a second range of angular motion, second member (324) will rotate with first member (322) relative to body (302) due to engagement between projections (326, 329). Body (302) will eventually arrest such counter-clockwise rotation when projection (304) engages distal projection (328), such that projection (304) again provides a hard stop.

It should be understood from the foregoing and from the series depicted in FIGS. 20A-20E that guidewire (106) is permitted to rotate through more than one full revolution about the longitudinal axis of guidewire (106); yet guidewire (106) is prevented from rotating through two or more full revolutions about the longitudinal axis of guidewire (106). It should also be understood that the angular range permitted for rotation of guidewire (106) may be varied by varying the configuration of guidewire movement mechanism (300). For instance, the angular range may be varied by changing the widths of one or more of projections (304, 326, 328, 329). The angular range may also be varied by providing an angular offset between projections (328, 329). In addition, the angular range may be varied (i.e., increased) by adding one or more additional rotatable members along the central longitudinal axis that is shared by members (322, 324) and guidewire (106). Such additional rotatable members may be configured and operable similar to second member (324). For instance, first member (322) may rotate through a first range of angular motion before engaging second member (324). First and second members (322, 324) may then rotate together through a second range of angular motion before engaging an additional rotatable member. All three members (322, 324) may then rotate together through a third range of angular motion before engaging projection (304), which may provide a hard stop preventing further rotation of the three members (322, 324) and guidewire (106). Other suitable ways in which rotation limiting assembly (320) may be varied will be apparent to those of ordinary skill in the art in view of the teachings herein.

V. Exemplary Alternative Guidewire Driving Assemblies

In examples described above, a knob (134, 310) is used to rotate guidewire (106) about the longitudinal axis of guidewire (106). In other words, a rotary movement of an actuator is used to provide rotation of guidewire (106). It may be desirable in some instances to instead provide rotation of guidewire (106) through a linear movement of an actuator. Such linear movement of an actuator may assist with providing visual and/or tactile feedback indicating where guidewire (106) is within an angular range of rotation. In addition or in the alternative, linear movement of an actuator may provide enhanced ergonomics over rotary movement of an actuator. Various examples of guidewire movement mechanisms that provide rotation of guidewire (106) through linear movement of an actuator are described below; while still other examples will be apparent to those of ordinary skill in the art in view of the teachings herein. The examples described below provide rotation of guidewire (106) through linear movement of an actuator along a path that is transverse to the longitudinal axis of guidewire (106). However, it should be understood that these examples may be readily modified to provide rotation of guidewire (106) through linear movement of an actuator along a path that is parallel to the longitudinal axis of guidewire (106).

As will be described in greater detail below, FIGS. 21-32C show several exemplary guidewire movement mechanisms (400, 450, 500) having linear-to-rotational movement mechanisms (410, 460, 510). It should be understood that any of the below described guidewire movement mechanisms (400, 450, 500) may be readily incorporated into instrument (100) in place of guidewire movement mechanism (112). Guidewire movement mechanisms (400, 450, 500) are configured to operate substantially similar to guidewire movement mechanisms (112, 300) discussed above except for the differences discussed below. In particular, guidewire movement mechanisms (400, 450, 500) are operable to longitudinally advance and retract guidewire (106) relative to handle (102), through guidewire support (118), and through the second lumen of dilation catheter (108) by longitudinally sliding guidewire movement mechanisms (400, 450, 500) along the length of handle (102). Furthermore, each guidewire movement mechanism (400, 450, 500) comprises a rotation mechanism (410, 460, 510) that is configured to operate substantially similar to rotation knobs (134, 310) discussed above except for the differences discussed below. In particular, each rotation mechanism (410, 460, 510) is operable to rotate guidewire (106) about the longitudinal axis of guidewire (106).

A. Exemplary Guidewire Movement Mechanism with Linear-to-Rotational Movement Mechanism FIGS. 21-24C show guidewire movement mechanism (400), which comprises rotation mechanism (410). Rotation mechanism (410) comprises an upper sled (420), a lower sled (430), and a biasing member (440). Upper sled (420) is slidably disposed within a pair of slots (404) formed in opposing surfaces of a body (402) of guidewire movement mechanism (400) such that upper sled (420) is operable to slide transversely relative to body (402) and relative to guidewire (106). A pad (422) is secured to a bottom surface of upper sled (420). Lower sled (430) is slidably disposed within a pair of slots (406) formed in opposing surfaces of body (402) of guidewire movement mechanism (400) such that lower sled (430) is operable to slide transversely relative to body (402) and relative to guidewire (106). A pad (432) is secured to a top surface of lower sled (430).

Figure 24A:
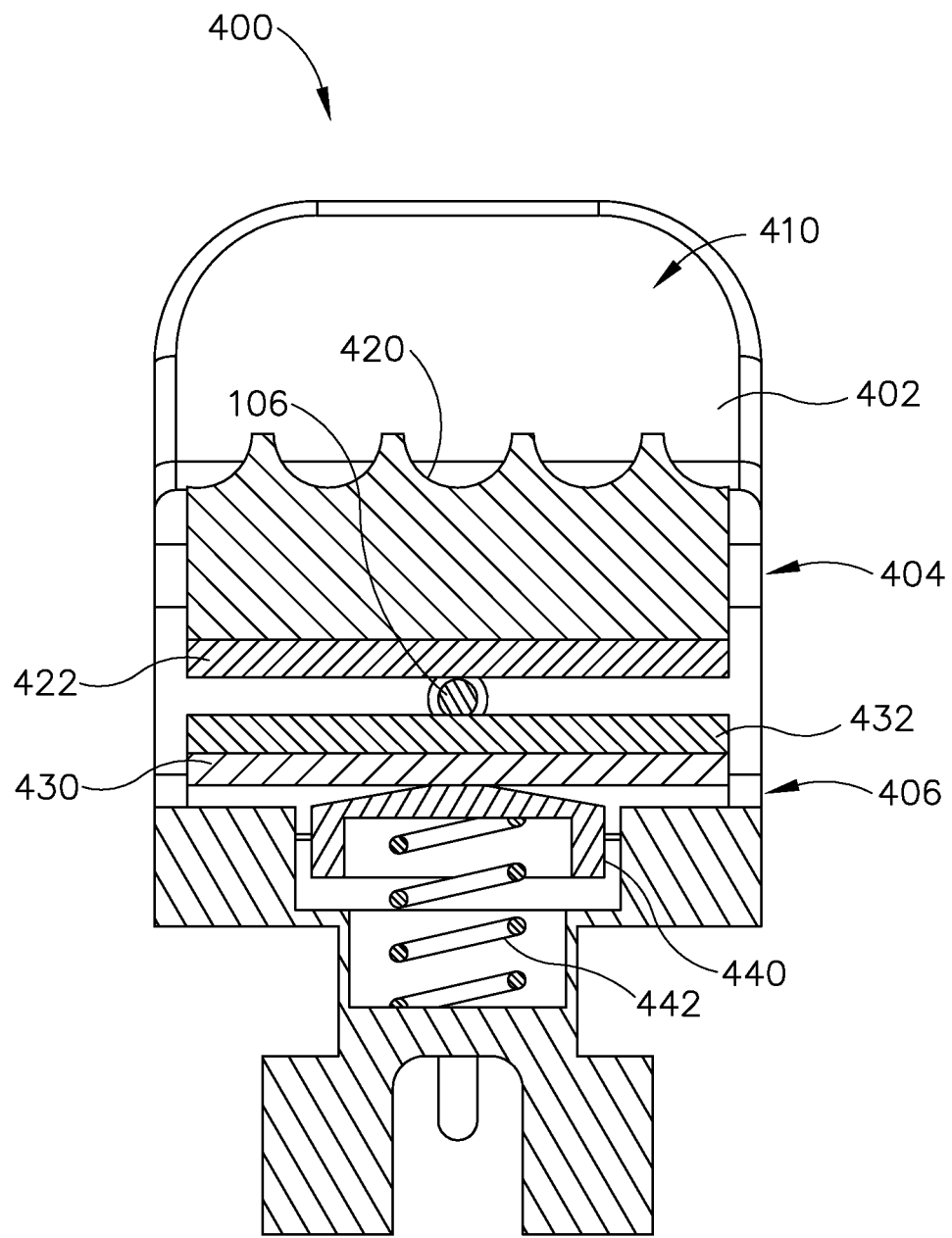
FIG. 24A depicts a cross-sectional rear view of the guidewire movement mechanism of FIG. 21, taken along line 24-24 of FIG. 22.
Figure 24B:
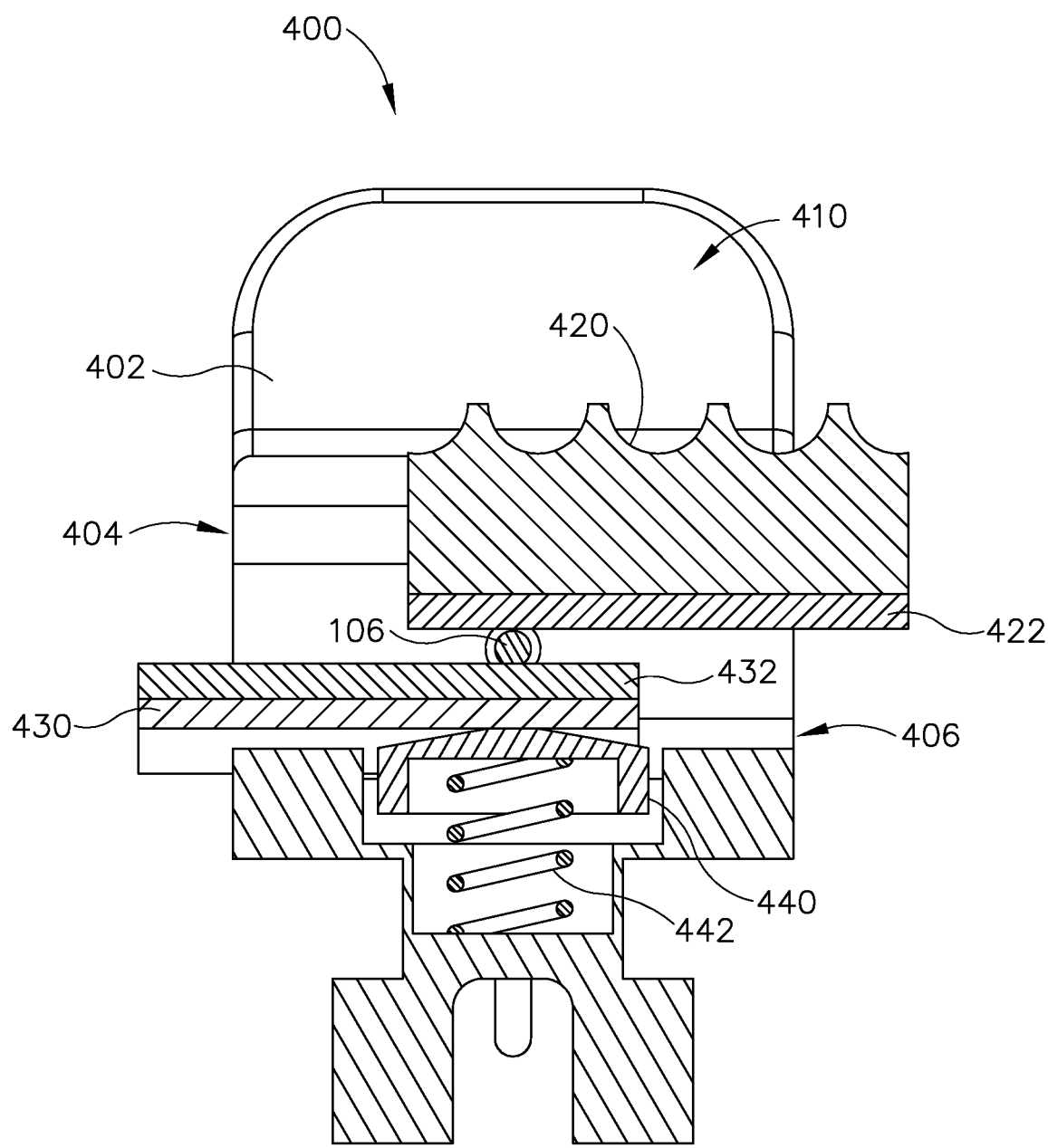
FIG. 24B depicts a cross-sectional rear view of the guidewire movement mechanism of FIG. 21, taken along line 24-24 of FIG. 22, with the guidewire rotated clockwise by opposing horizontal transverse movement of a pair of sleds.
Figure 24C:
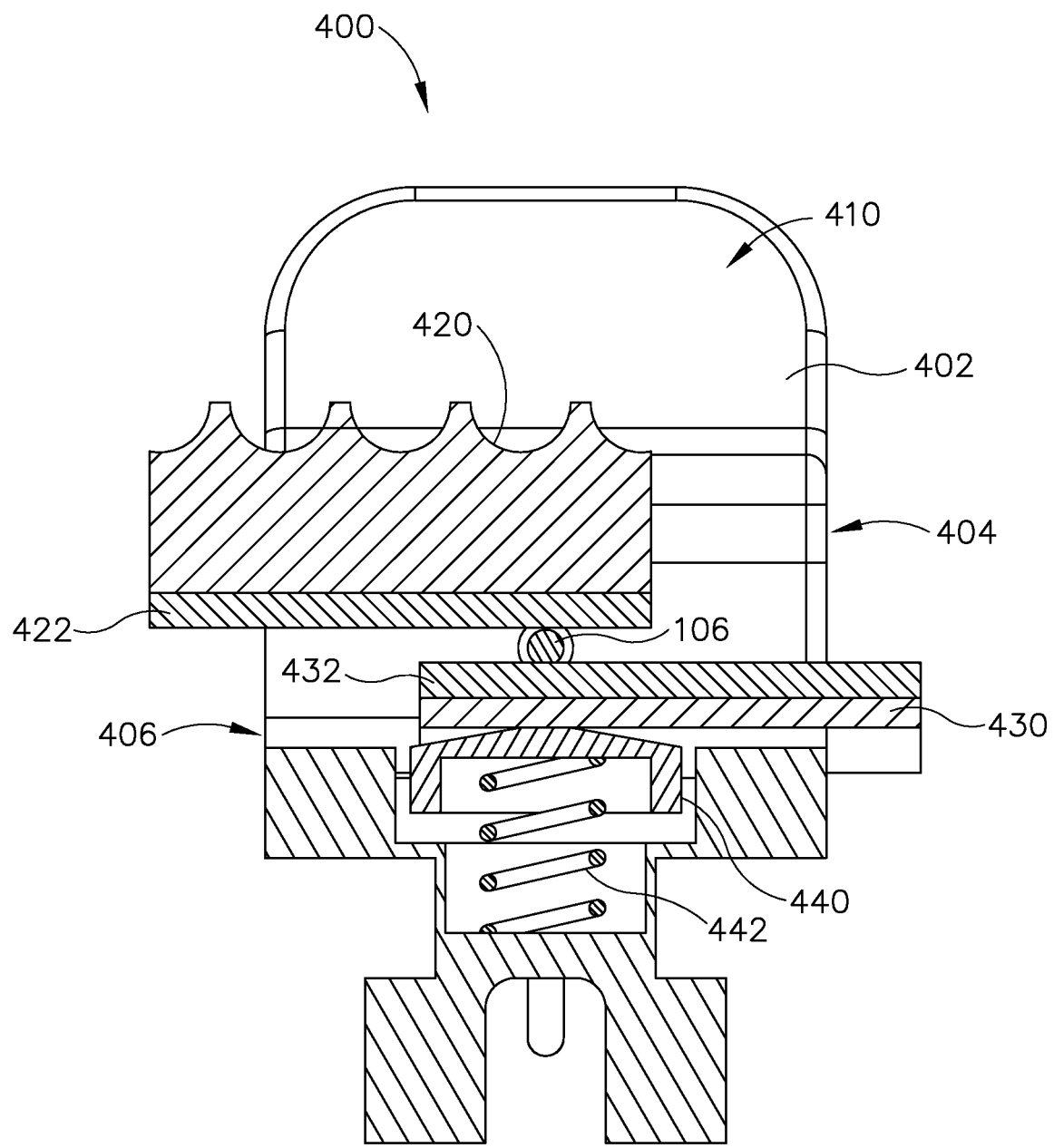
FIG. 24C depicts a cross-sectional rear view of the guidewire movement mechanism of FIG. 21, taken along line 24-24 of FIG. 22, with the guidewire rotated counter-clockwise by opposing horizontal transverse movement of the pair of sleds.
Figure 25:
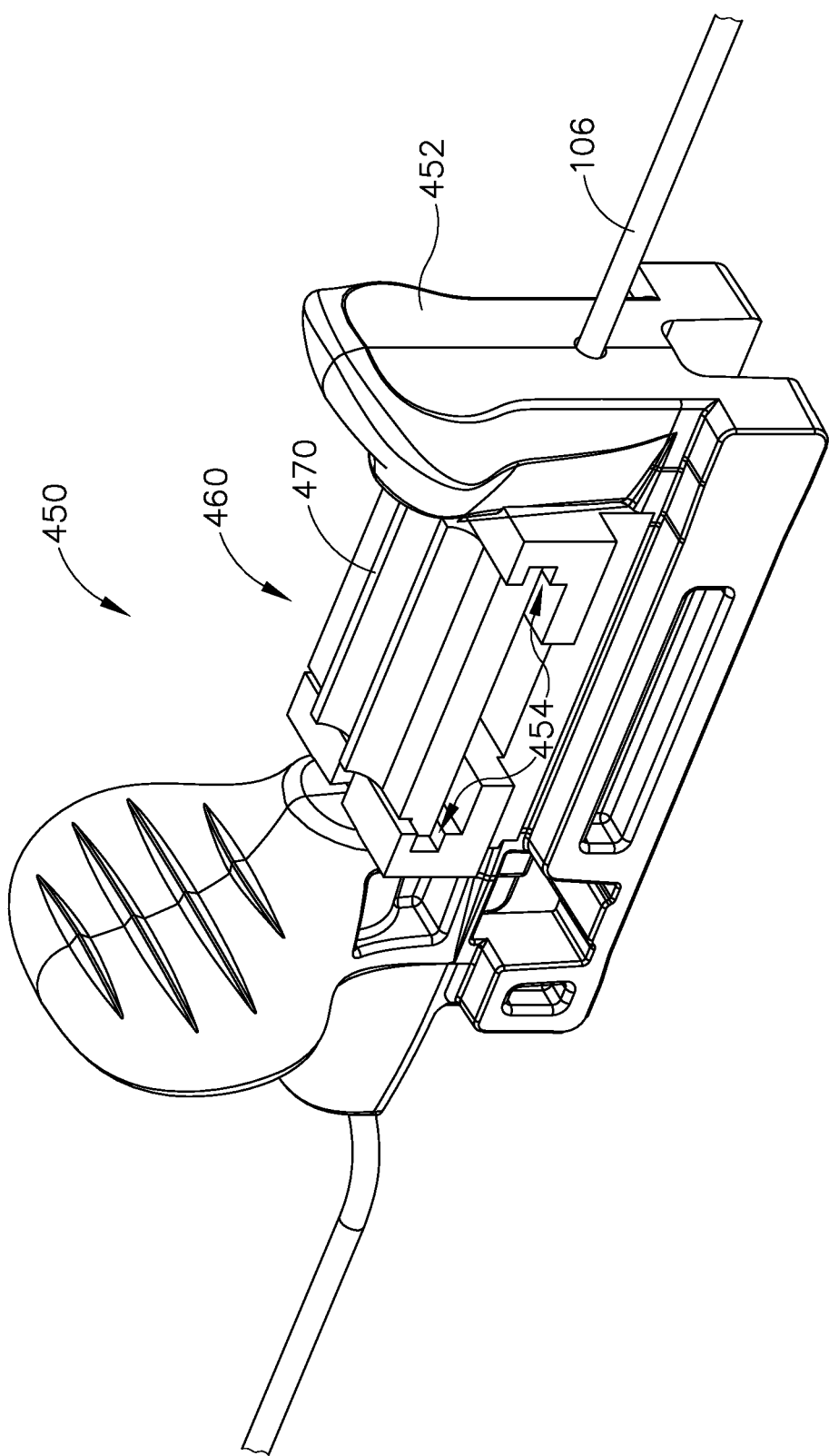
FIG. 25 depicts a perspective view of another exemplary guidewire movement mechanism that may be incorporated into the instrument of FIG. 4.
Figure 26:
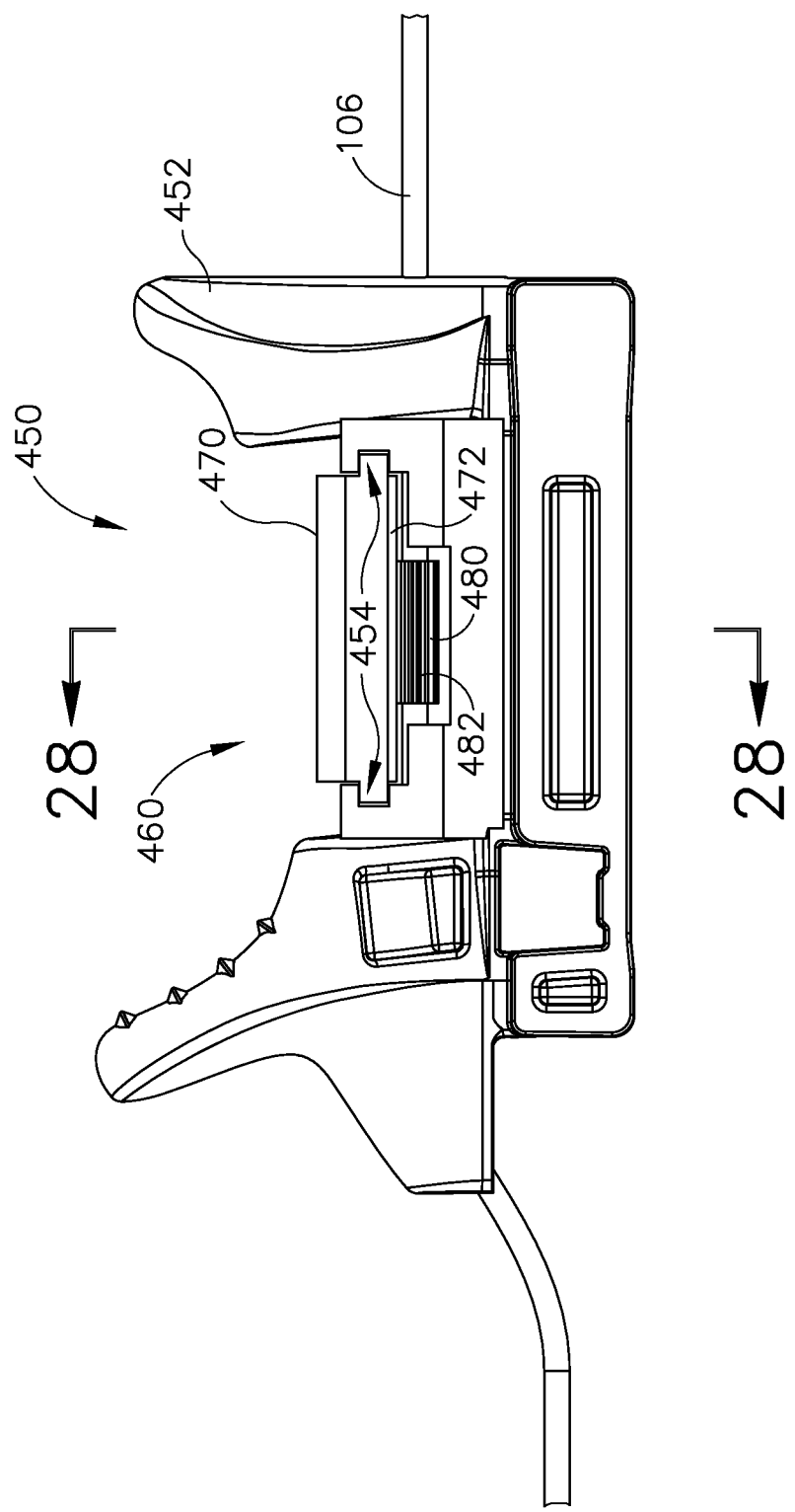
FIG. 26 depicts a side elevational view of the guidewire movement mechanism of FIG. 25.
Figure 27:
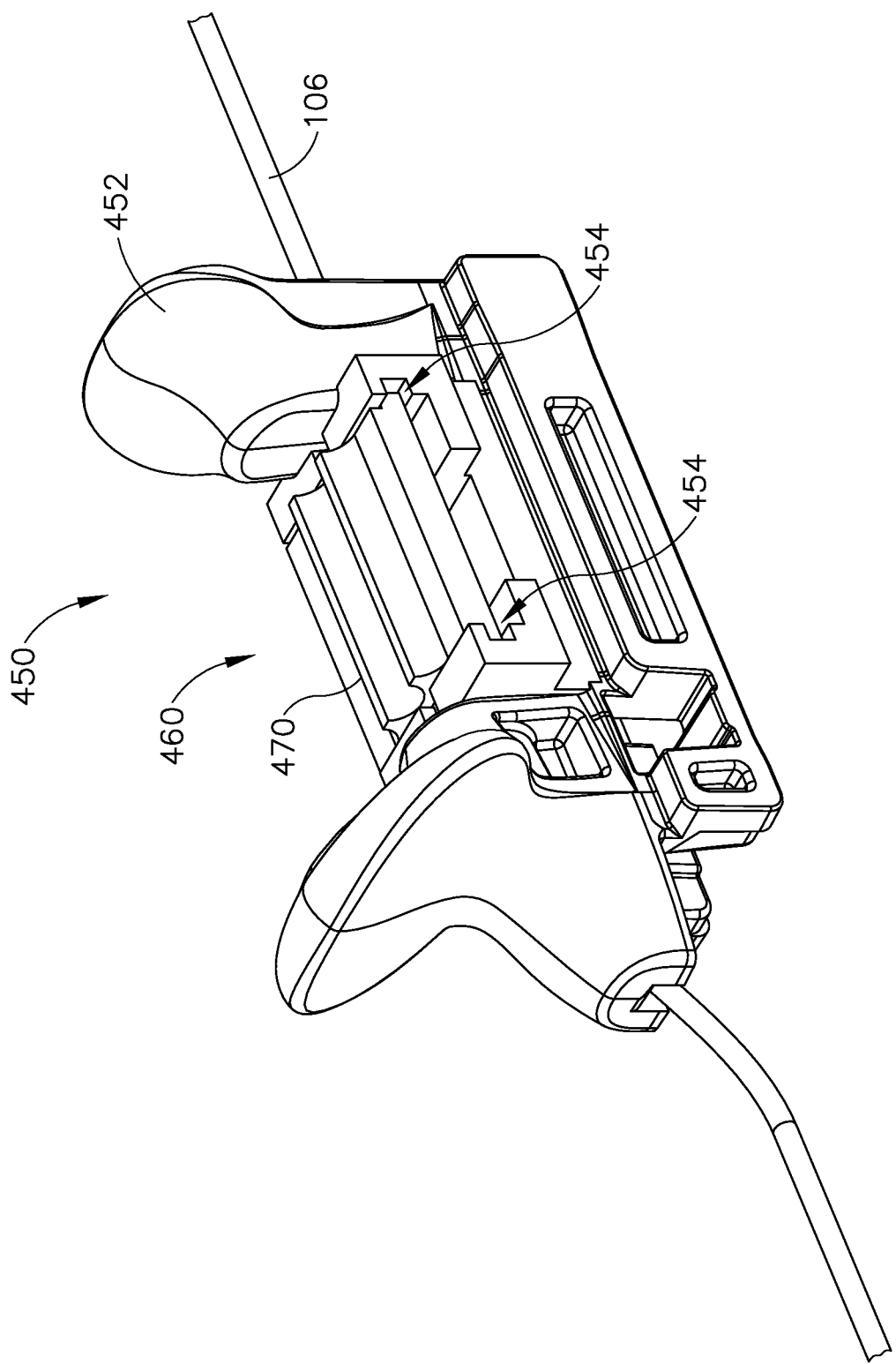
FIG. 27 depicts a perspective view of the guidewire movement mechanism of FIG. 25.

As best seen in FIGS. 24A-24C, guidewire (106) is interposed between pad (422) of upper sled (420) and pad (432) of lower sled (430) such that guidewire (106) engages a bottom surface of pad (422) and a top surface of pad (432). Pads (422, 432) may comprise a high friction material (e.g., silicone rubber, etched metal, grit blasted metal, etc.) and/or provide a deformable surface that bears upon guidewire (106) to thereby increase contact between sleds (420, 430) and guide wire (106) or otherwise prevent slippage of guidewire (106). Biasing member (440) is urged upwardly by a coil spring (442) and bears against a bottom surface of lower sled (430). Biasing member (440) thereby urges lower sled (430) upwardly so as to compress guidewire (106) between lower sled (430) and upper sled (420). This compression enhances the friction between pads (422, 432) and guidewire (106). Thus, it should be understood that opposing transverse sliding of sleds (420, 430) causes rotation of guidewire (106). It should also be understood that coil spring (442) and biasing member (440) may be modified or substituted with various other structures, including but not limited to a leaf spring, etc.

As upper sled (420) is slid transversely in a first direction as shown in the transition from FIG. 24A to FIG. 24B, engagement between pad (422) and guidewire (106) causes clockwise rotation of guidewire (106), which in turn causes opposing transverse sliding of lower sled (430) due to engagement between pad (432) and guidewire (106). As shown in the transition from FIG. 24B to FIG. 24C, as upper sled (420) is slid transversely in a second direction, engagement between pad (422) and guidewire (106) causes counter-clockwise rotation of guidewire (106), which in turn causes opposing transverse sliding of lower sled (430) due to engagement between pad (432) and guidewire (106). Thus, linear movement of sled (420) provides rotation of guidewire (106) about the longitudinal axis of guidewire (106).

Guidewire movement mechanism (400) may comprise one or more bushings (not shown) disposed about guidewire (106), between guidewire (106) and body (402), within body (402). Among other things, these bushings may provide support to guidewire (106), provide for concurrent longitudinal translation of guidewire (106) with guidewire movement mechanism (400), and permit rotation of guidewire (106) relative to body (402). In addition to or as an alternative to bushings, polytetrafluoroethylene (PTFE), and/or some other material(s) may be used to reduce friction between guidewire (106) and body (402), enhancing free rotation of guidewire (106) within body (402).

FIGS. 25-28C show guidewire movement mechanism (450), which comprises rotation mechanism (460). Rotation mechanism (460) comprises a sled (470) and a pinion gear (480). Sled (470) is slidably disposed within a pair of slots (454) formed in opposing surfaces of a body (452) of guidewire movement mechanism (450) such that sled (470) is operable to slide transversely relative to body (452) and relative to guidewire (106). Guidewire (106) is unitarily secured within gear (480) such that rotation of gear (480) causes concurrent rotation of guidewire (106). A bottom surface of sled (470) comprises a plurality of teeth (472) that are configured to engage teeth (482) of gear (480) in a rack and pinion relationship. Transverse sliding of sled (470) within slots (454) thus causes rotation of gear (480), which in turn causes rotation of guidewire (106). It should therefore be understood that transverse sliding of sled (470) relative to body (452) is causes rotation of guidewire (106).

Figure 28A:
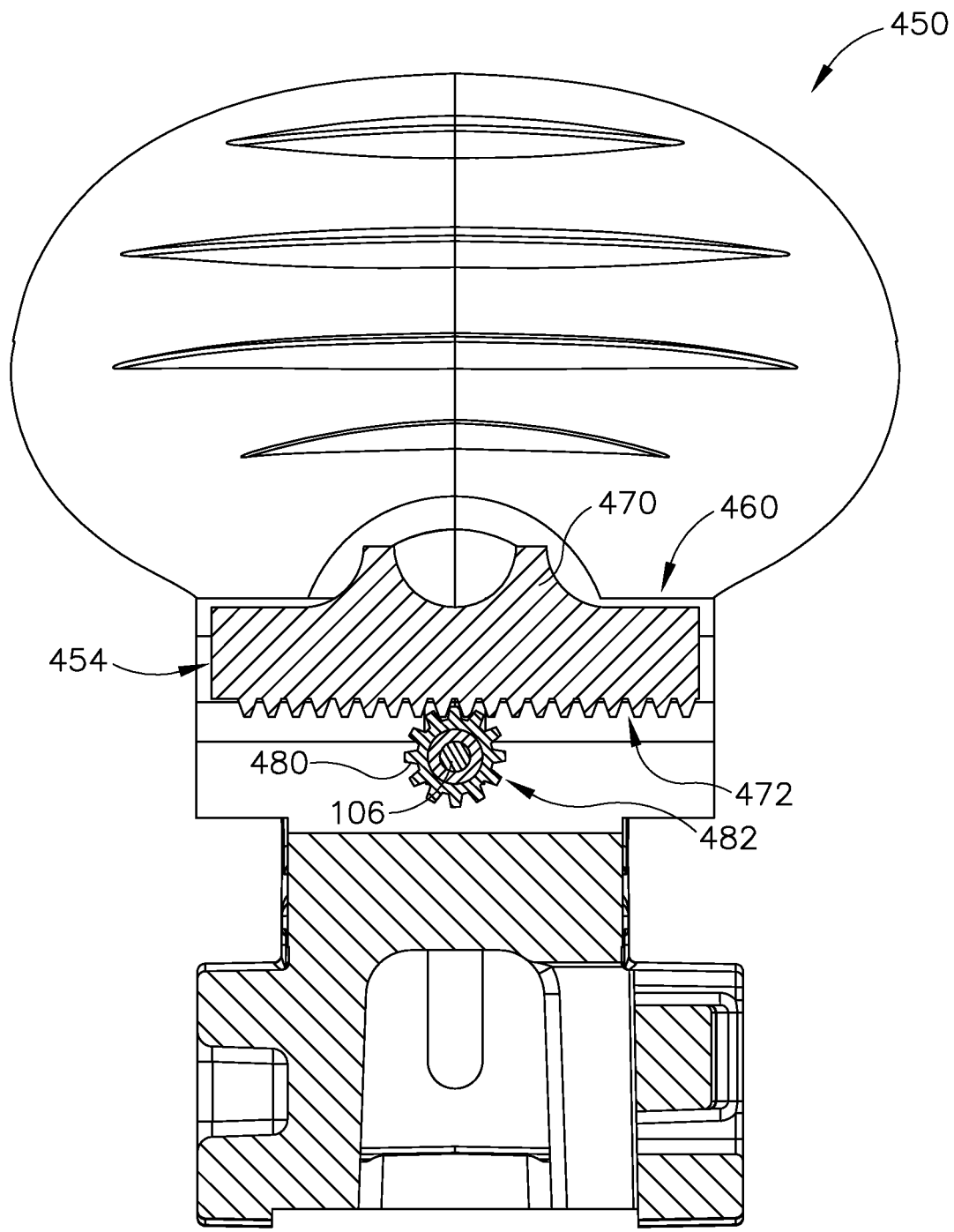
FIG. 28A depicts a cross-sectional rear view of the guidewire movement mechanism of FIG. 25, taken along line 28-28 of FIG. 26.
Figure 28B:
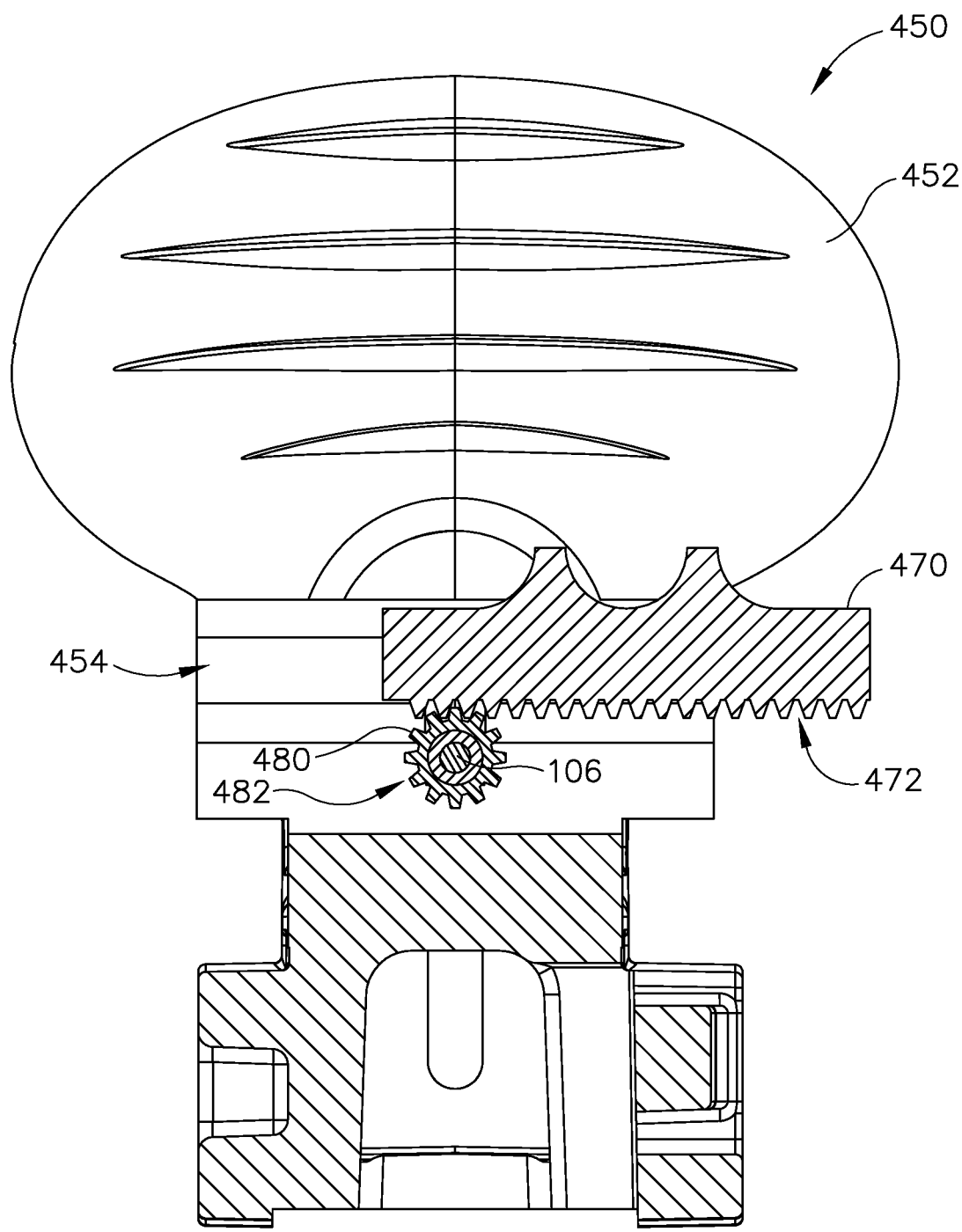
FIG. 28B depicts a cross-sectional rear view of the guidewire movement mechanism of FIG. 25, taken along line 28-28 of FIG. 26, with the guidewire rotated clockwise by horizontal transverse movement of a sled in a first direction.
Figure 28C:
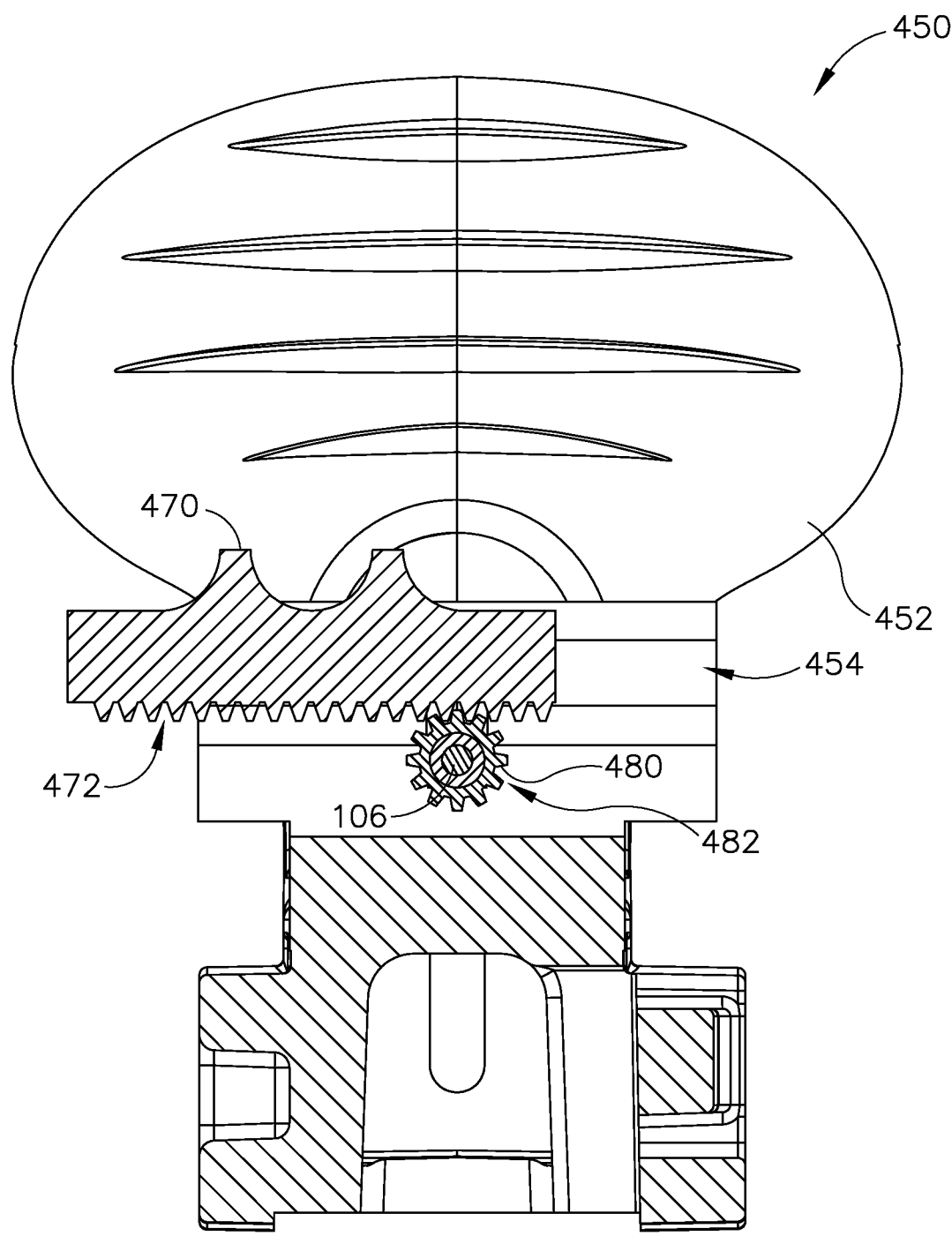
FIG. 28C depicts a cross-sectional rear view of the guidewire movement mechanism of FIG. 25, taken along line 28-28 of FIG. 26, with the guidewire rotated counter-clockwise by horizontal transverse movement of the sled in a second direction.
Figure 29:
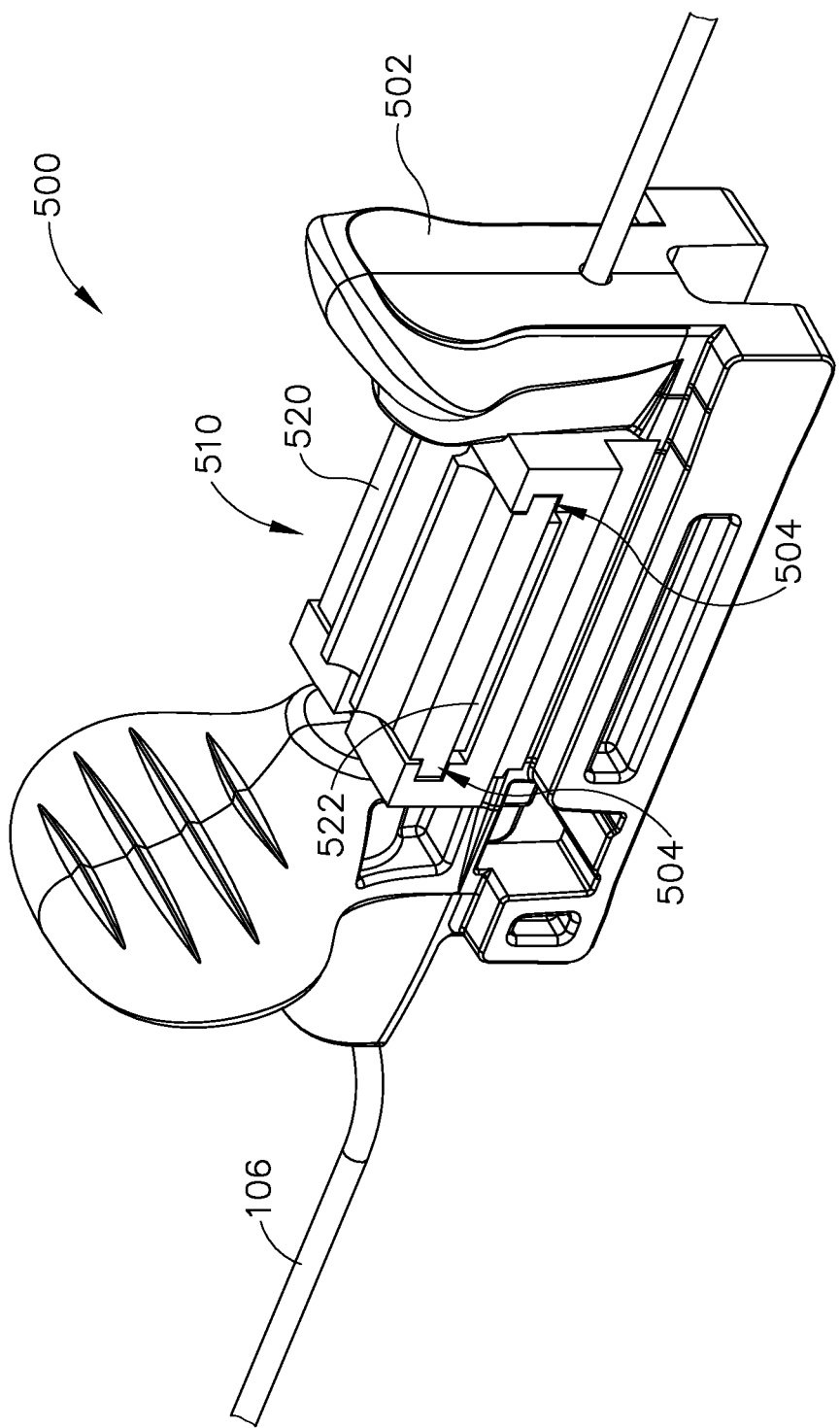
FIG. 29 depicts a perspective view of another exemplary guidewire movement mechanism that may be incorporated into the instrument of FIG. 4.
Figure 30:
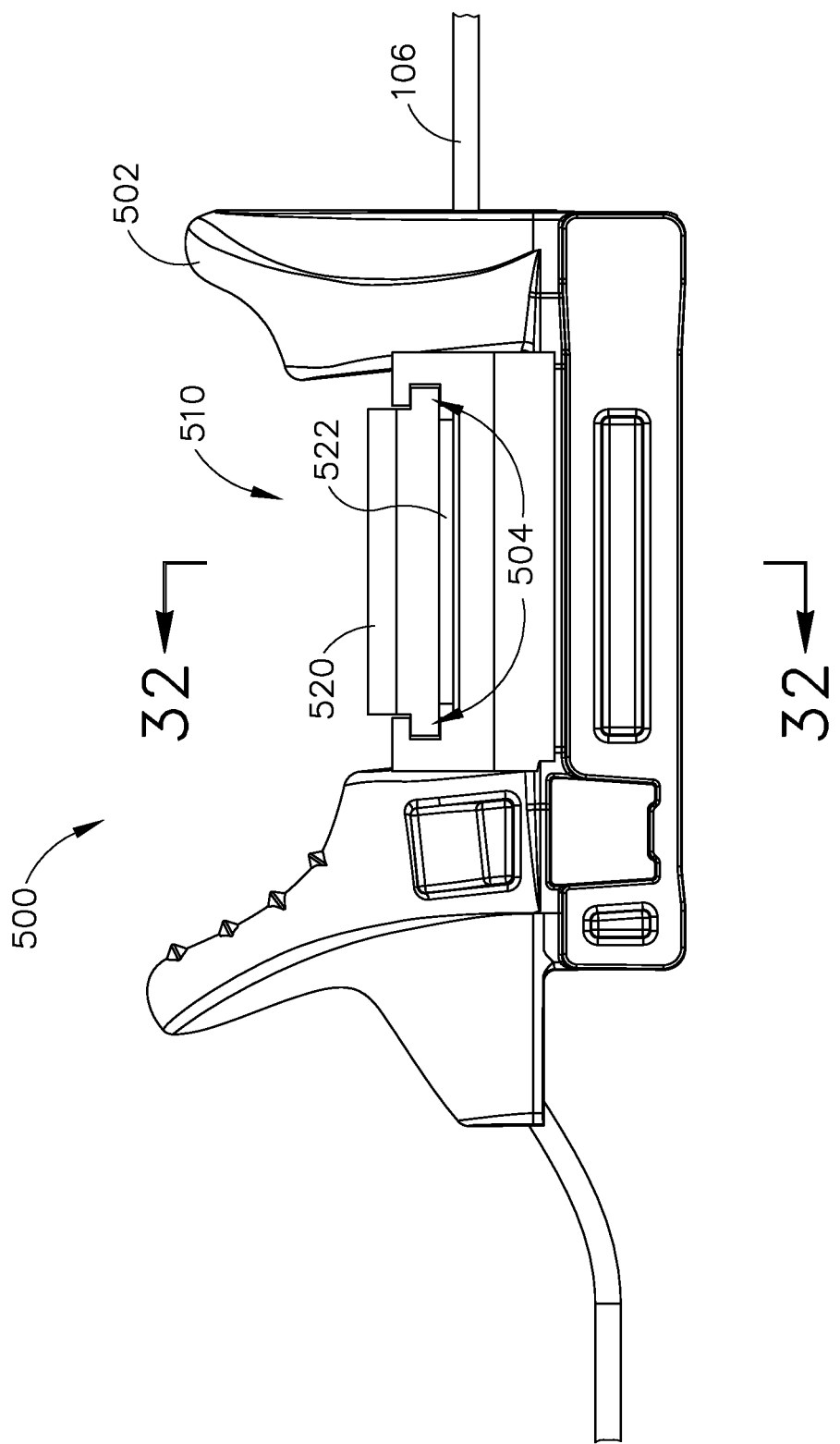
FIG. 30 depicts a side elevational view of the guidewire movement mechanism of FIG. 29.
Figure 31:
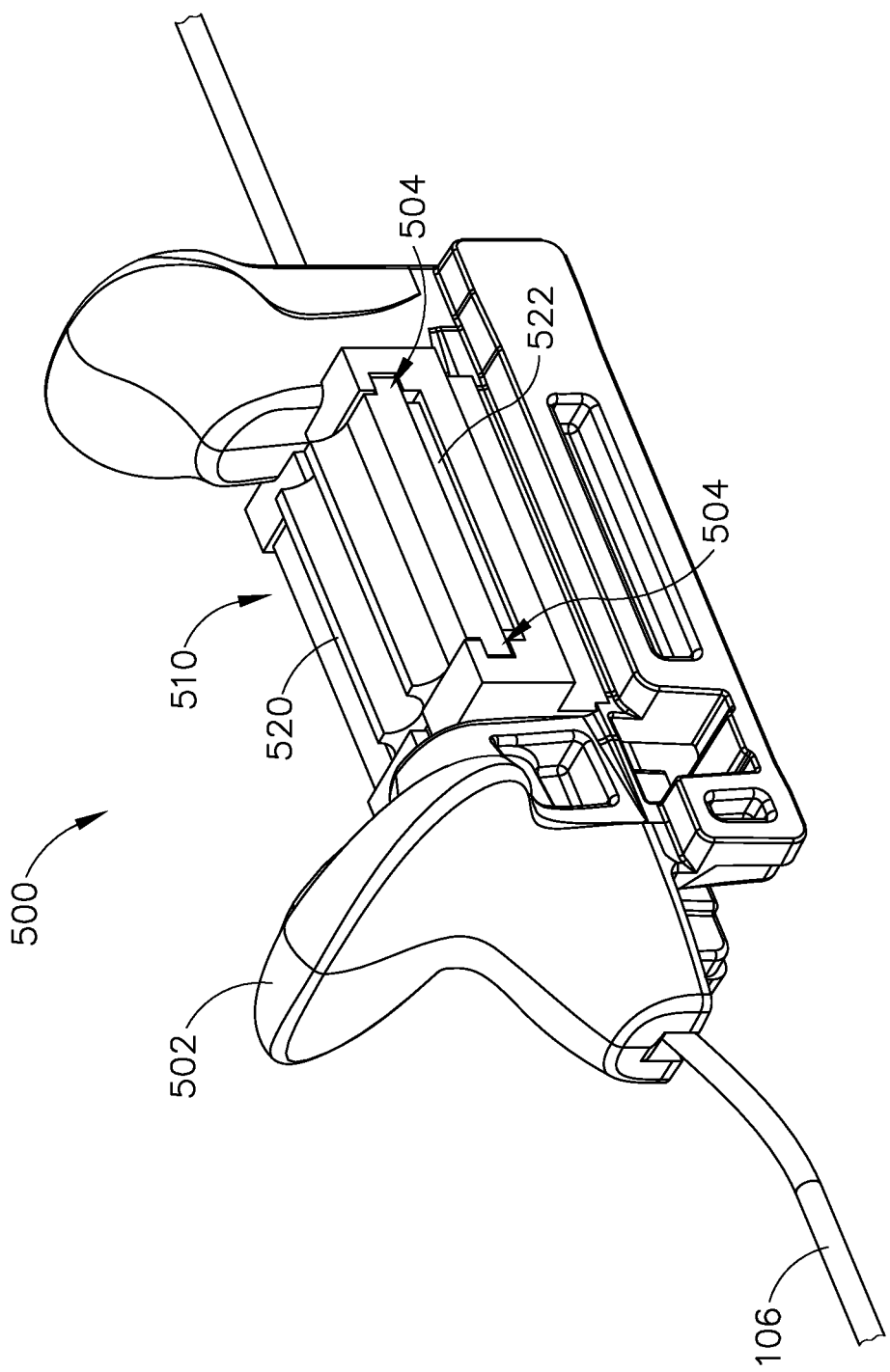
FIG. 31 depicts a perspective view of the guidewire movement mechanism of FIG. 29.

As sled (470) is slid transversely in a first direction as shown in the transition from FIG. 28A to FIG. 28B, engagement between teeth (472) of sled (470) and teeth (482) of gear (480) causes clockwise rotation of guidewire (106). Also shown in the transition from FIG. 28B to FIG. 28C, as sled (470) is slid transversely in a second direction, engagement between teeth (472) of sled (470) and teeth (482) of gear (480) causes counter-clockwise rotation of guidewire (106). Thus, linear movement of sled (470) provides rotation of guidewire (106) about the longitudinal axis of guidewire (106).

Guidewire movement mechanism (450) may comprise one or more bushings (not shown) disposed about guidewire (106), between guidewire (106) and body (452), within body (452). Among other things, these bushings may provide support to guidewire (106), provide for concurrent longitudinal translation of guidewire (106) with guidewire movement mechanism (450), and permit rotation of guidewire (106) relative to body (452). In addition to or as an alternative to bushings, PTFE, and/or some other material(s) may be used to reduce friction between guidewire (106) and body (452), enhancing free rotation of guidewire (106) within body (452).

FIGS. 29-32C show guidewire movement mechanism (500), which comprises rotation mechanism (510). Rotation mechanism (510) comprises a sled (520). Sled (520) is slidably disposed within a pair of slots (504) formed in opposing surfaces of a body (502) of guidewire movement mechanism (500) such that sled (520) is operable to slide transversely relative to body (502) and relative to guidewire (106). A pad (522) is secured to a bottom surface of sled (520). As best seen in FIGS. 24A-24C, guidewire (106) is disposed within a longitudinal channel (506) formed in body (502) such that guidewire (106) engages a bottom surface of pad (522) of sled (520). Guidewire (106) is free to rotate within channel (506). Thus, transverse sliding of sled (520) relative to body (502) cause rotation of guidewire (106).

It should be understood that pad (522) may comprise a high friction material (e.g., silicone rubber, etched metal, grit blasted metal, etc.) and/or provide a deformable surface that bears upon guidewire (106) to thereby increase contact between sled (520) and guide wire (106) or otherwise prevent slippage of guidewire (106). It should also be understood that a lubricious material (e.g., PTFE, acetal, etc.) may be provided in channel (506) to reduce friction between guidewire (106) and body (502), thereby promoting free rotation of guidewire (106) in channel (506).

Figure 32A:
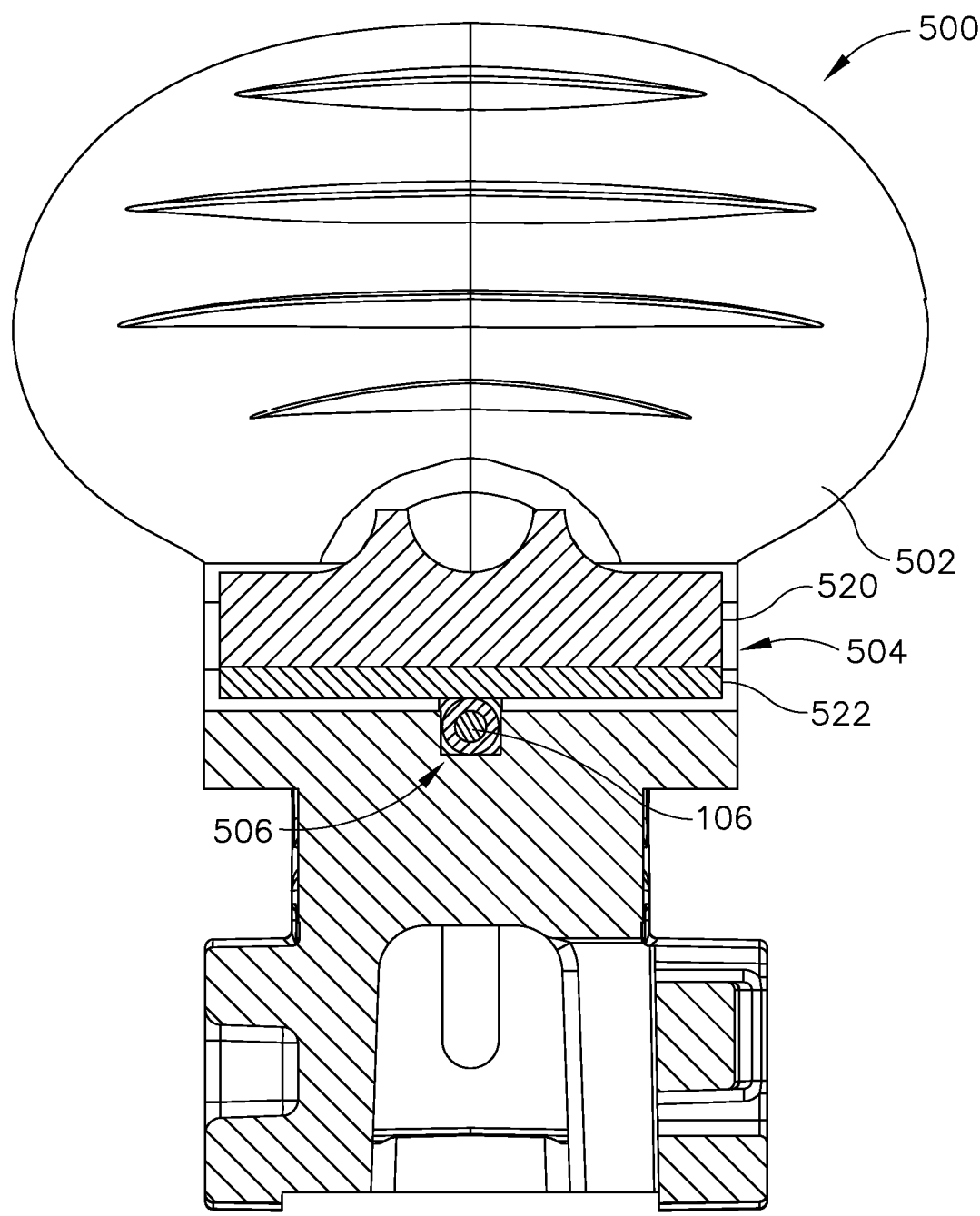
FIG. 32A depicts a cross-sectional rear view of the guidewire movement mechanism of FIG. 29, taken along line 32-32 of FIG. 30.
Figure 32B:
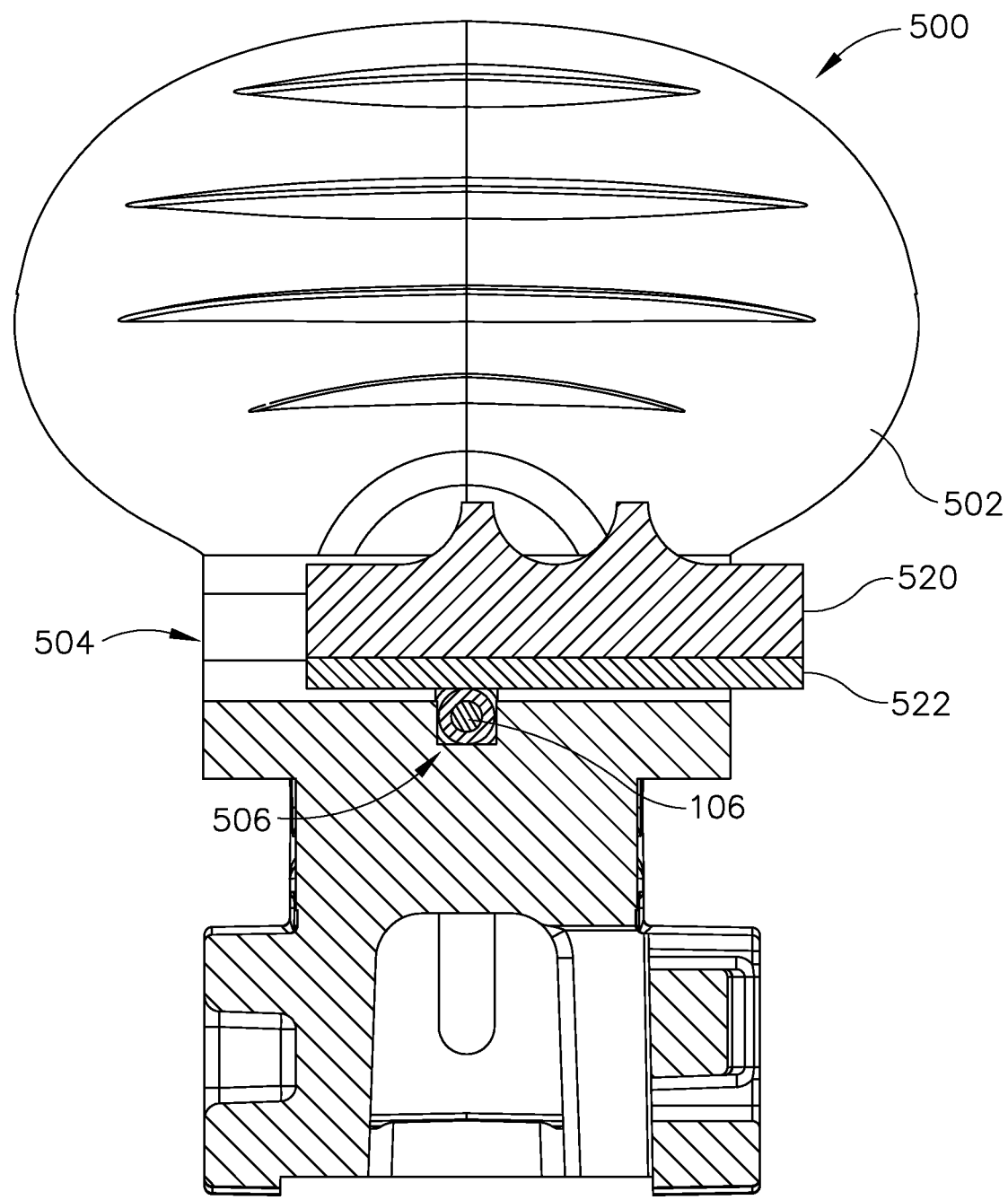
FIG. 32B depicts a cross-sectional rear view of the guidewire movement mechanism of FIG. 29, taken along line 32-32 of FIG. 30, with the guidewire rotated clockwise by horizontal transverse movement of a sled in a first direction.
Figure 32C:
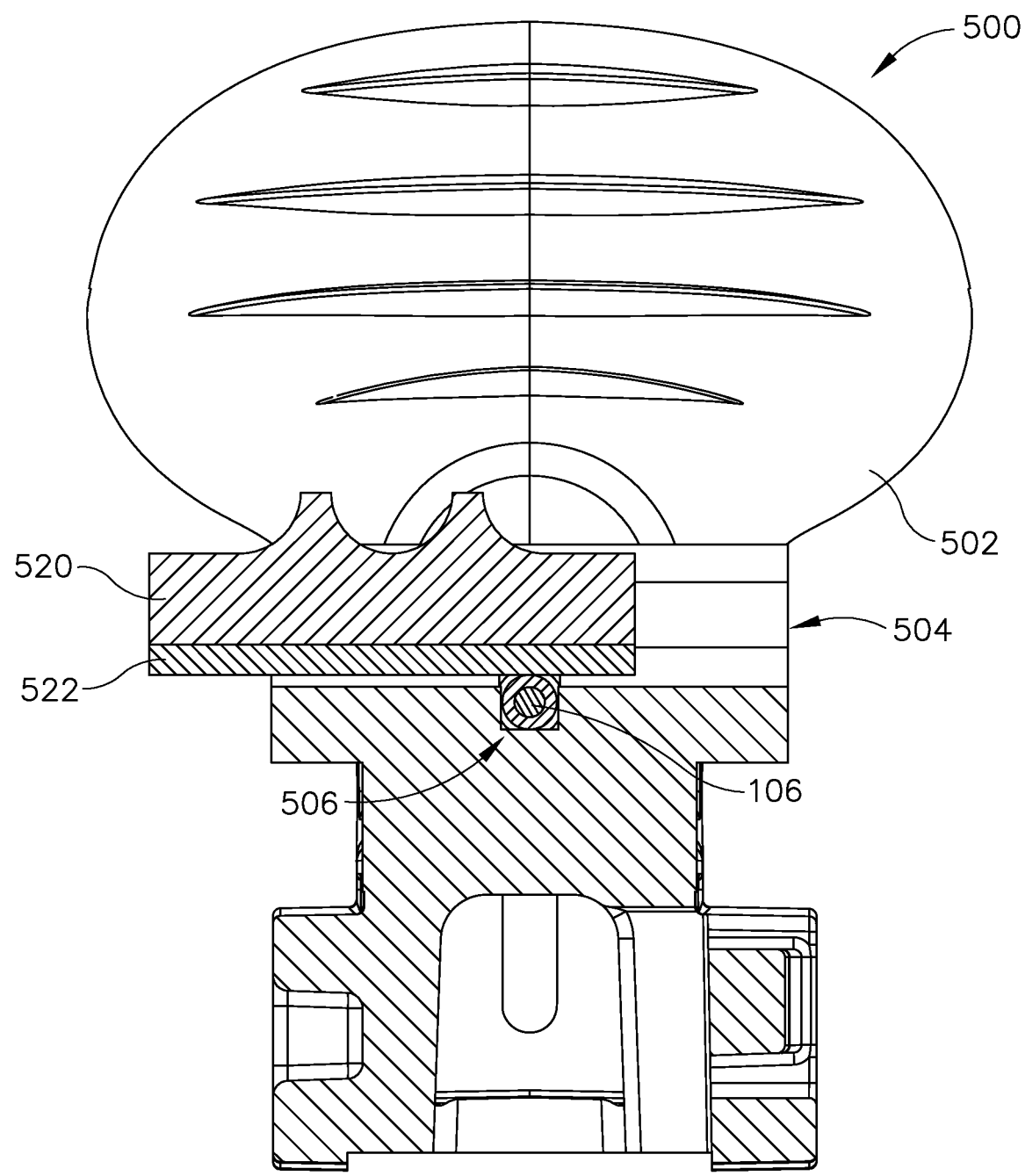
FIG. 32C depicts a cross-sectional rear view of the guidewire movement mechanism of FIG. 29, taken along line 32-32 of FIG. 30, with the guidewire rotated counter-clockwise by horizontal transverse movement of a sled in a second direction.
Figure 33:
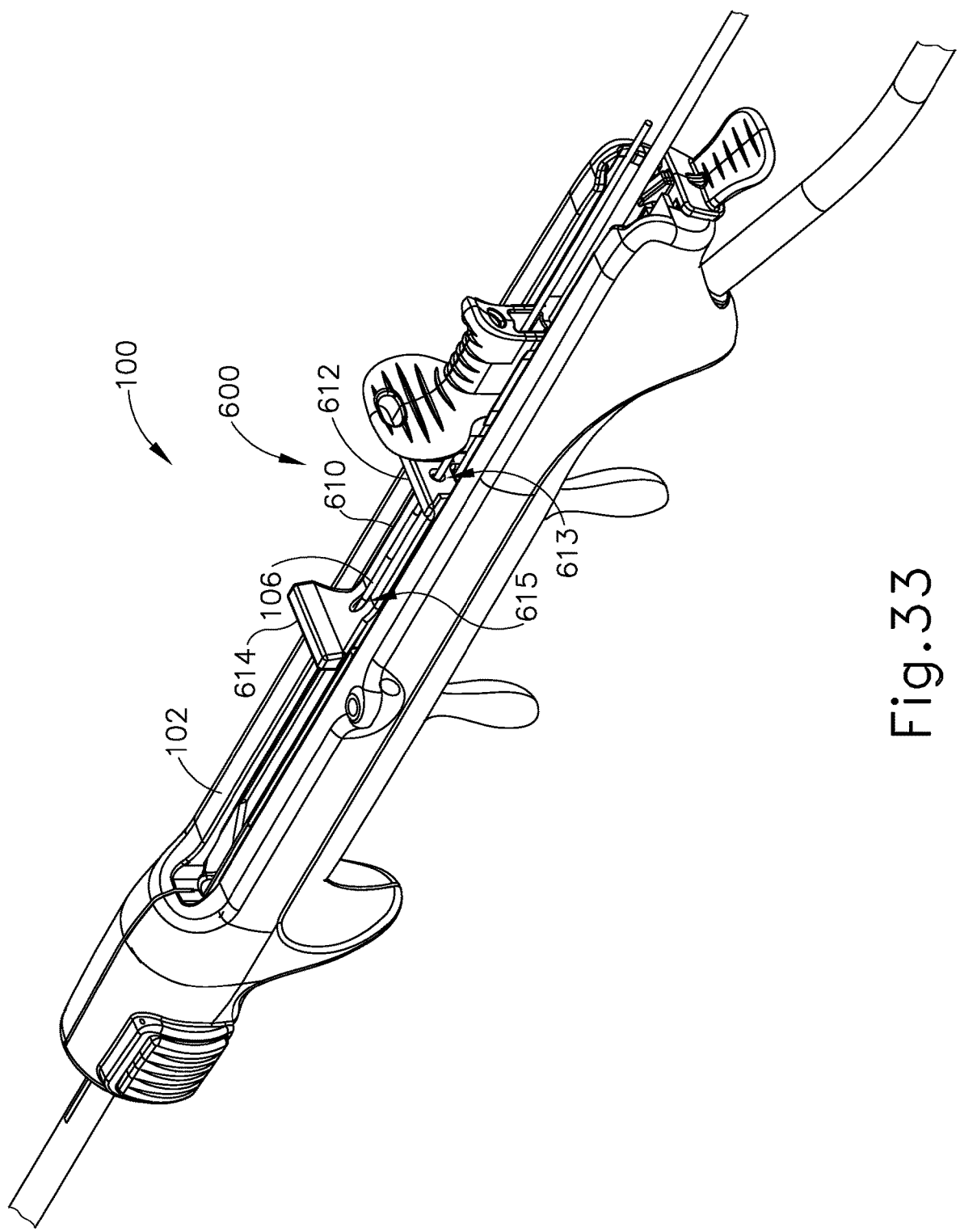
FIG. 33 depicts a perspective view of another exemplary instrument suitable for incorporation into the dilation catheter system of FIG. 1.

As sled (520) is slid transversely in a first direction as shown in the transition from FIG. 32A to FIG. 32B, engagement between pad (522) and guidewire (106) causes clockwise rotation of guidewire (106). As shown in the transition from FIG. 32B to FIG. 32C, as sled (520) is slid transversely in a second direction, engagement between pad (522) and guidewire (106) causes counter-clockwise rotation of guidewire (106). Thus, linear movement of sled (520) provides rotation of guidewire (106) about the longitudinal axis of guidewire (106).

Guidewire movement mechanism (500) may comprise one or more bushings (not shown) disposed about guidewire (106), between guidewire (106) and body (502), within body (502). Among other things, these bushings may provide support to guidewire (106), provide for concurrent longitudinal translation of guidewire (106) with guidewire movement mechanism (500), and permit rotation of guidewire (106) relative to body (502). In addition to or as an alternative to bushings, PTFE, and/or some other material(s) may be used to reduce friction between guidewire (106) and body (502), enhancing free rotation of guidewire (106) within body (502).

B. Exemplary Guidewire Movement Mechanism with Direct Guidewire Contact

In some versions of instrument (100), it may be desirable to provide a guidewire movement mechanism (112) with features that provide for direct contact with guidewire (106) to thereby provide rotational movement to guidewire (106). FIGS. 33-44 show an exemplary guidewire movement mechanism (600) having such features. It should be understood that guidewire movement mechanism (600) may be readily incorporated into instrument (100) in place of guidewire movement mechanism (112). Guidewire movement mechanism (600) is configured to operate substantially similar to guidewire movement mechanism (112) discussed above except for the differences discussed below. In particular, guidewire movement mechanism (600) is operable to longitudinally advance and retract guidewire (106) relative to handle (102), through guidewire support (118), and through the second lumen of dilation catheter (108) by longitudinally sliding guidewire movement mechanism (600) along the length of handle (102).

Figure 34:
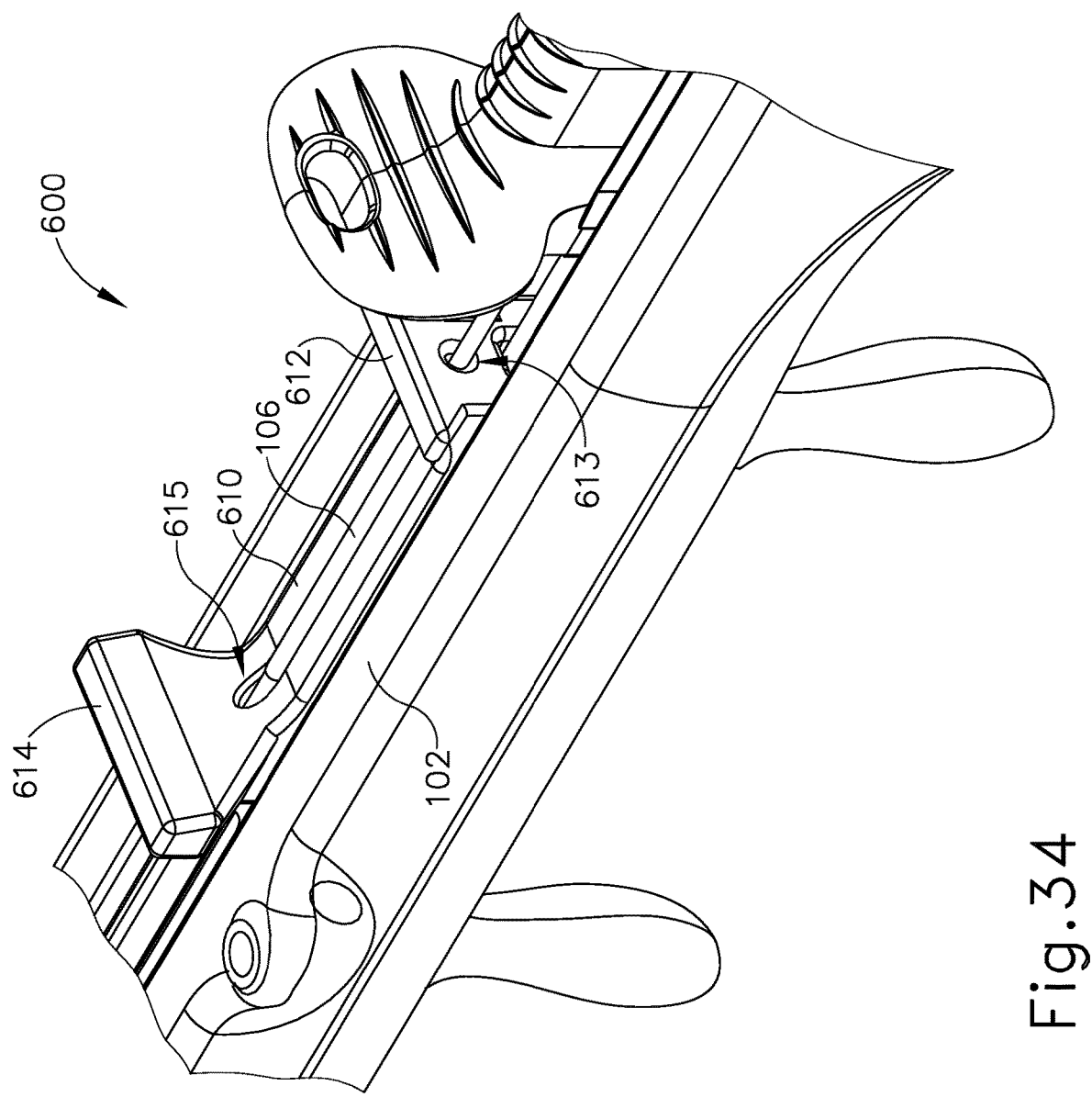
FIG. 34 depicts a detailed perspective view of the instrument of FIG. 33.
Figure 35:
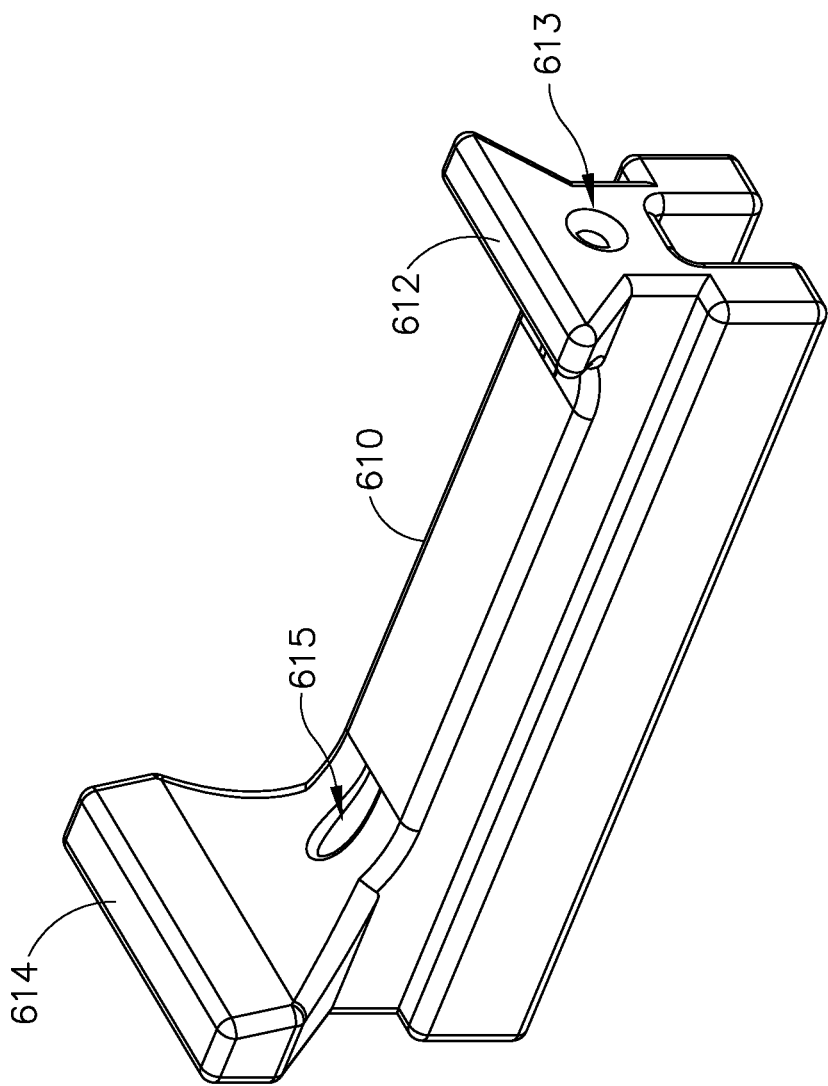
FIG. 35 depicts a perspective view of a distal member of a guidewire movement mechanism of the instrument of FIG. 33.
Figure 36:
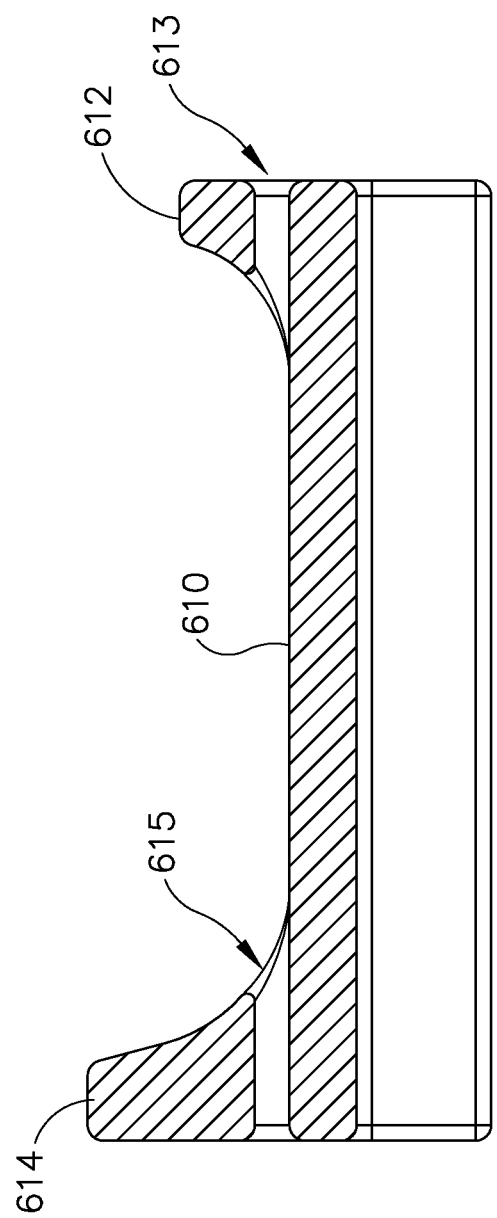
FIG. 36 depicts a cross-sectional side elevational view of the distal member of FIG. 35.

Guidewire movement mechanism (600) of the present example comprises a body (610) that is configured to slide along the length of handle (102) of instrument (100). As best seen in FIGS. 34-36, body (610) comprises a proximal cantle portion (612) and a distal pommel portion (614). Pommel and cantle portions (614, 612) are configured to receive and engage an operator's finger and thereby provide surfaces for the operator's finger to bear against to drive guidewire movement mechanism (600) distally and proximally relative to handle (102). Guidewire (106) is rotatably disposed within a pair of openings (613, 615) that are formed through cantle and pommel portions (612, 614); and passes along the length of body (610). As shown in FIG. 34, a portion of guidewire (106) is exposed between cantle and pommel portions (612, 614) such that an operator may directly contact guidewire (106) with the operator's finger to thereby rotate guidewire (106) about the longitudinal axis of guidewire (106). For instance, the operator may engage guidewire (106) with his or her index finger or thumb to thereby directly rotate guidewire (106) by moving the finger or thumb along a path that is generally transverse to the longitudinal axis of guidewire (106).

Figure 37:
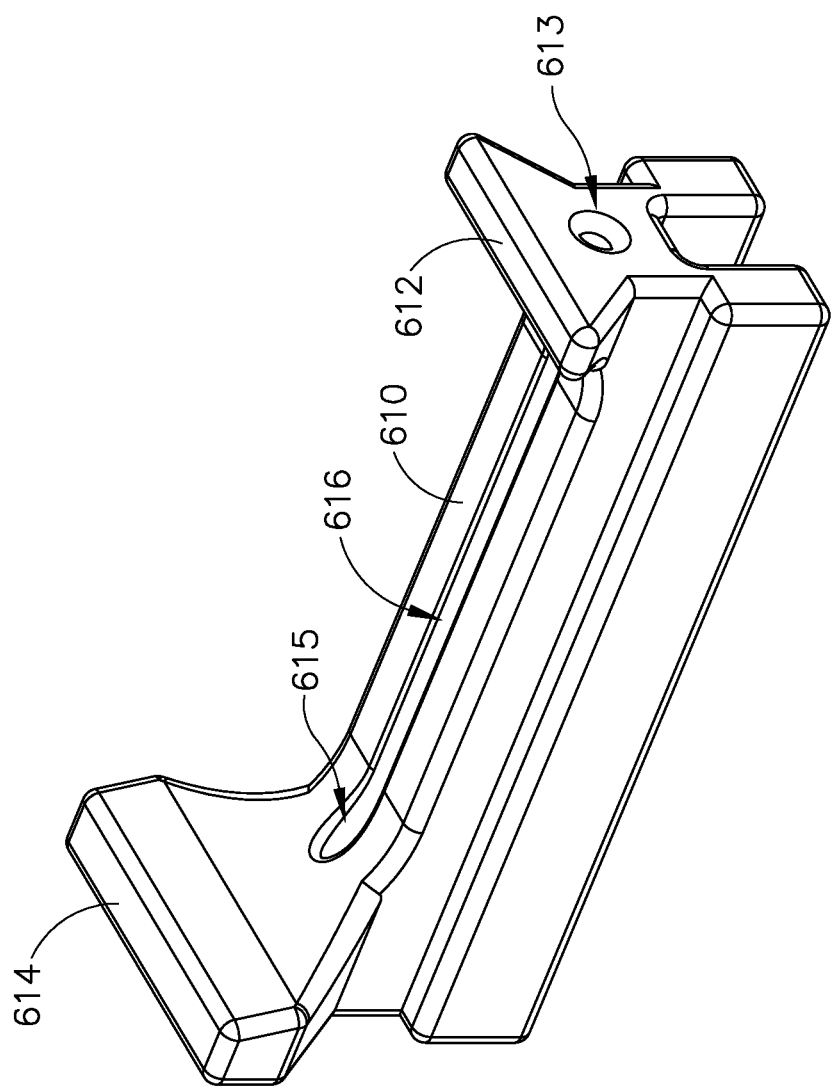
FIG. 37 depicts a perspective view of an exemplary alternative distal member of a guidewire movement mechanism of the instrument of FIG. 33.
Figure 38:
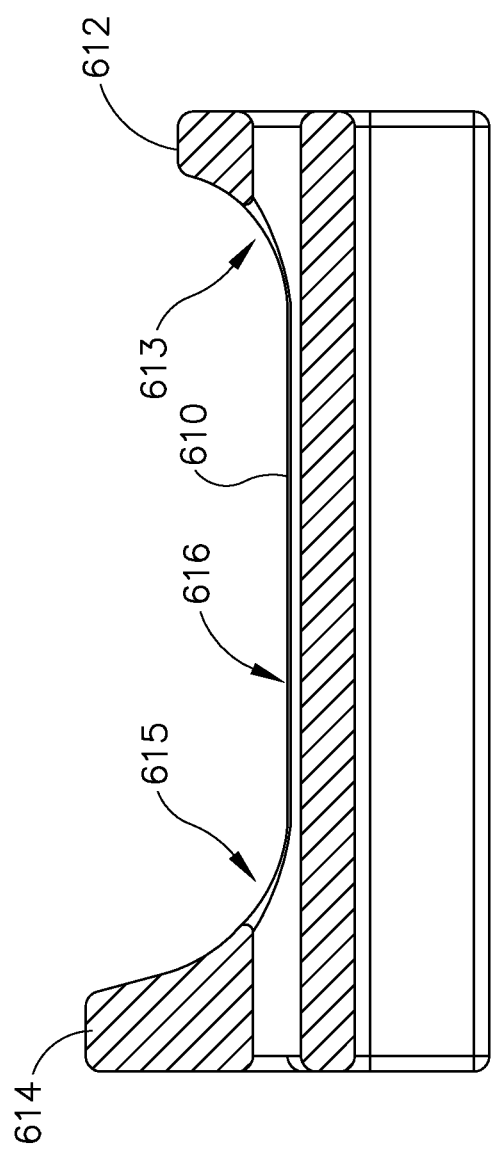
FIG. 38 depicts a cross-sectional side elevational view of the distal member of FIG. 37.

In some instances, the operator may inadvertently cause guidewire (106) to move transversely when the operator attempts to rotate guidewire (106). This may in turn cause longitudinal movement of guidewire (106). Thus, it may be desirable to provide body (610) and/or guidewire (106) with features that are configured to retain and/or provide lateral strength to at least a portion of guidewire (106) so as to avoid inadvertent transverse movement of guidewire (106) between cantle and pommel portions (612, 614). By way of example only, as shown in FIGS. 37-38, body (610) may comprise an elongate channel (616) extending between openings (613, 615). Guidewire (106) is rotatably disposed within channel (616). Channel (616) is configured to prevent transverse movement of guidewire (106) between cantle and pommel portions (612, 614). With guidewire (106) disposed within channel (616), a top portion of guidewire (106) remains exposed such that the operator may contact guidewire (106) directly with the operator's finger to thereby cause rotation of guidewire (106) while preventing transverse movement of guidewire (106).

Figure 40:
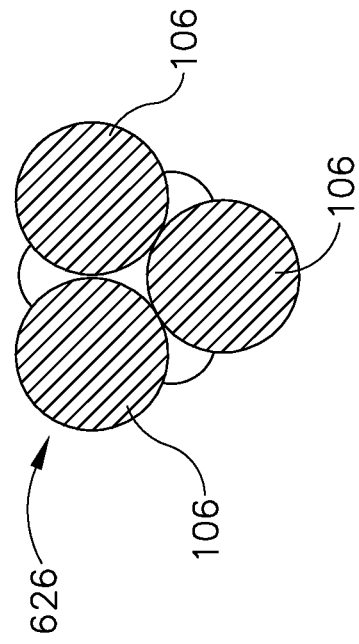
FIG. 40 depicts a cross-sectional rear view of the guidewire assembly of FIG. 39.
Figure 39:
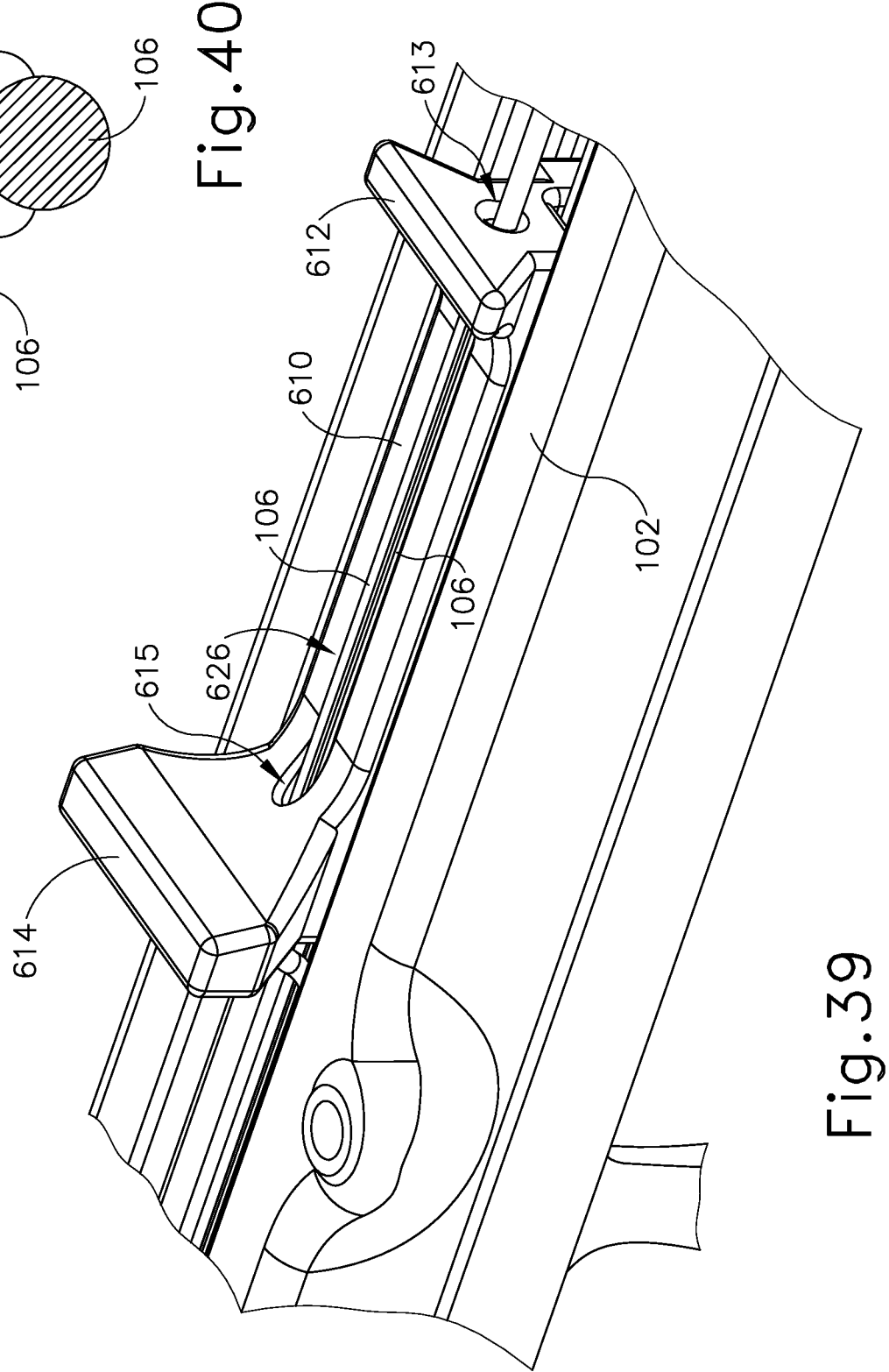
FIG. 39 depicts a detailed perspective view of the instrument of FIG. 33 with an exemplary alternative guidewire assembly.

FIGS. 39 and 40 show an exemplary guidewire assembly (620) with enhanced lateral strength to prevent transverse movement of guidewire (106) between cantle and pommel portions (612, 614). Guidewire assembly (620) comprises a plurality of guidewires (106) that are welded together to thereby provide additional strength to guidewire assembly (620). In particular, and as best shown in FIG. 40, guidewire assembly (620) of the present example comprises three guidewires (106) welded together in a triangular orientation. It should be understood, however, that guidewire assembly (620) may comprise any appropriate number of guidewires (106) welded together in any appropriate orientation. It should also be understood that, in some versions, guidewire assembly (620) is only provided in the region between cantle and pommel portions (612, 614), such just a single guidewire (106) extends distally from pommel portion (614) and just a single guidewire (106) extends proximally from cantle portion (612).

Figure 41:
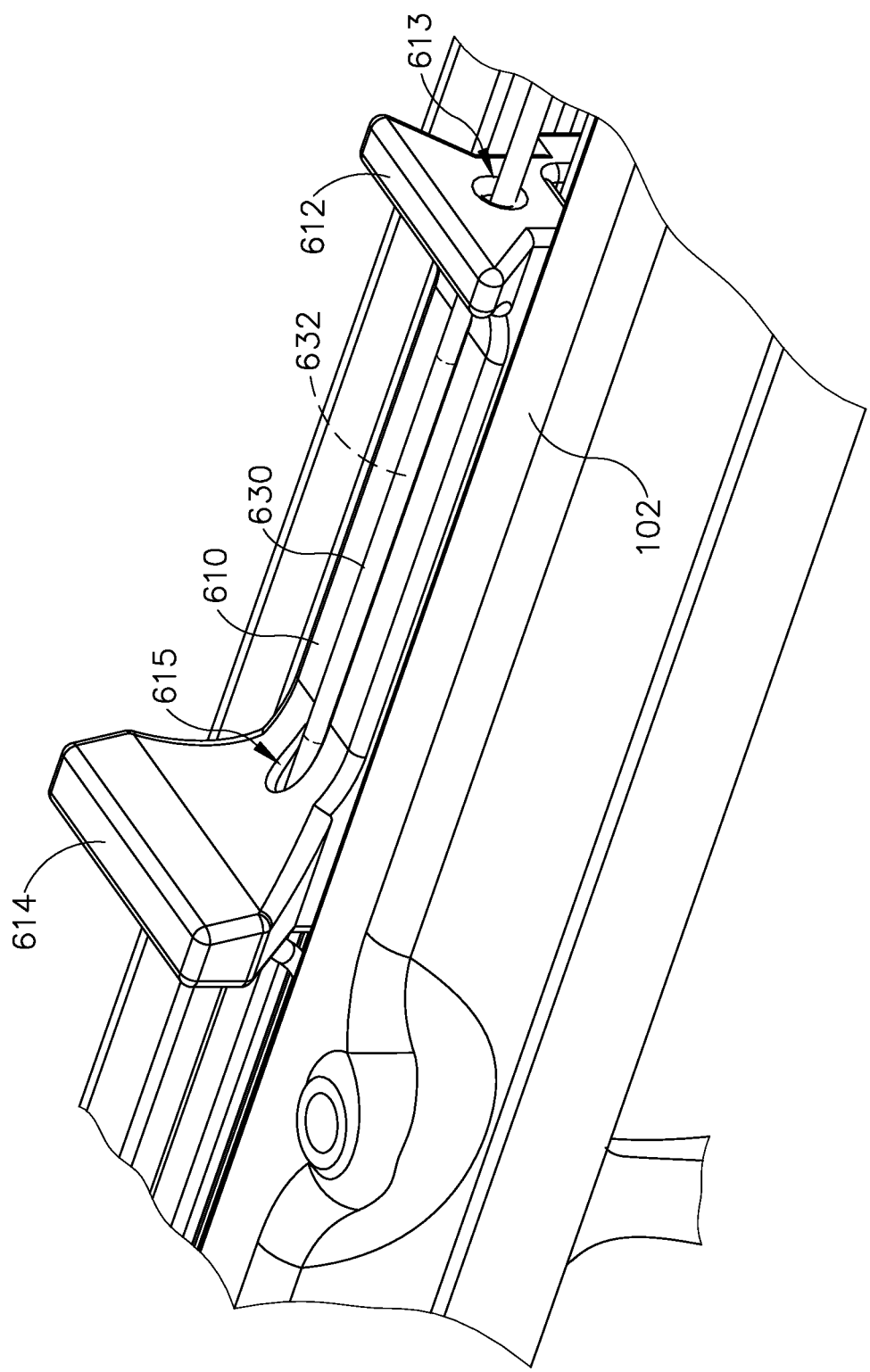
FIG. 41 depicts a detailed perspective view of the instrument of FIG. 33 with another exemplary alternative guidewire.
Figure 42:
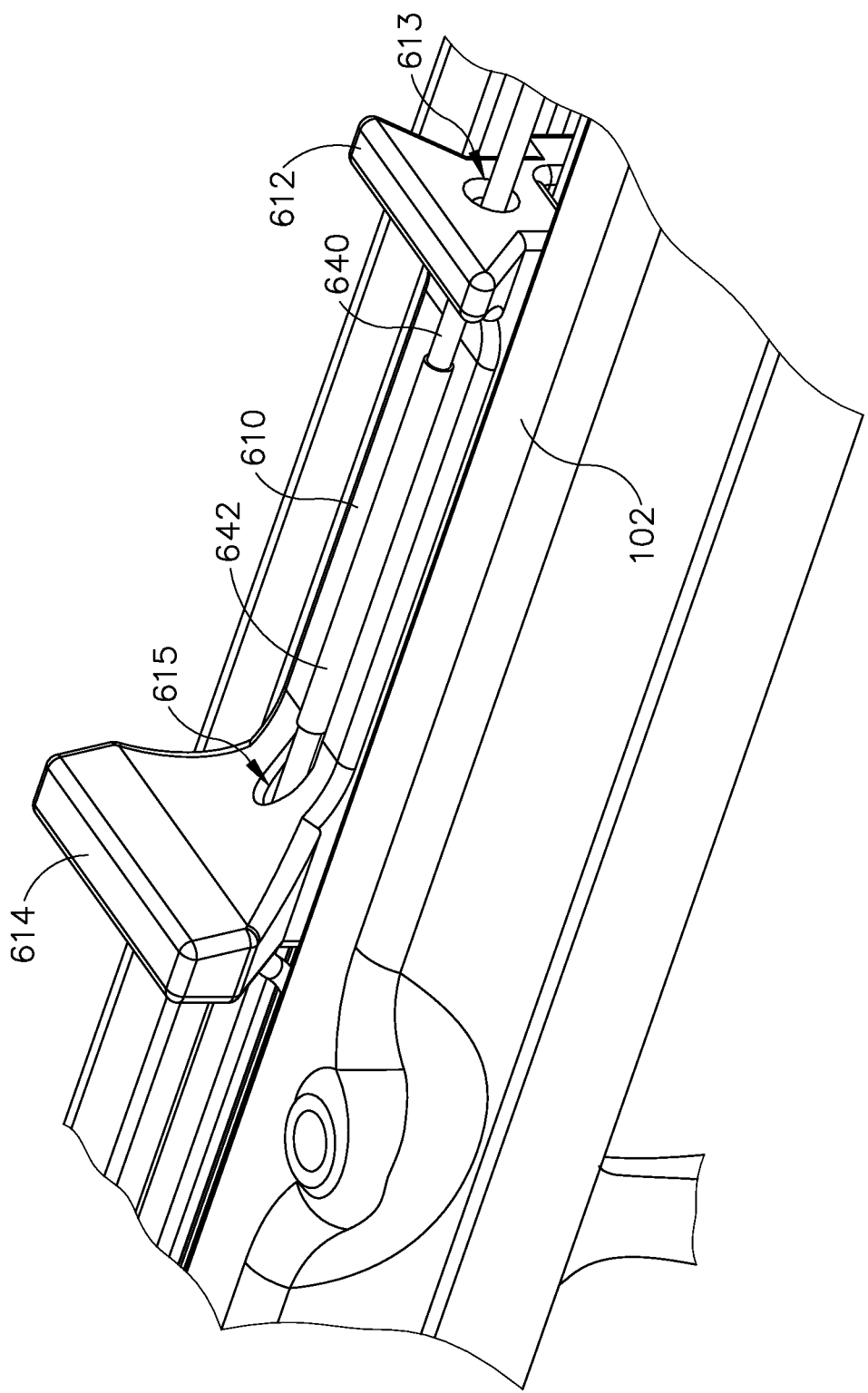
FIG. 42 depicts a detailed perspective view of the instrument of FIG. 33 with another exemplary alternative guidewire.
Figure 43:
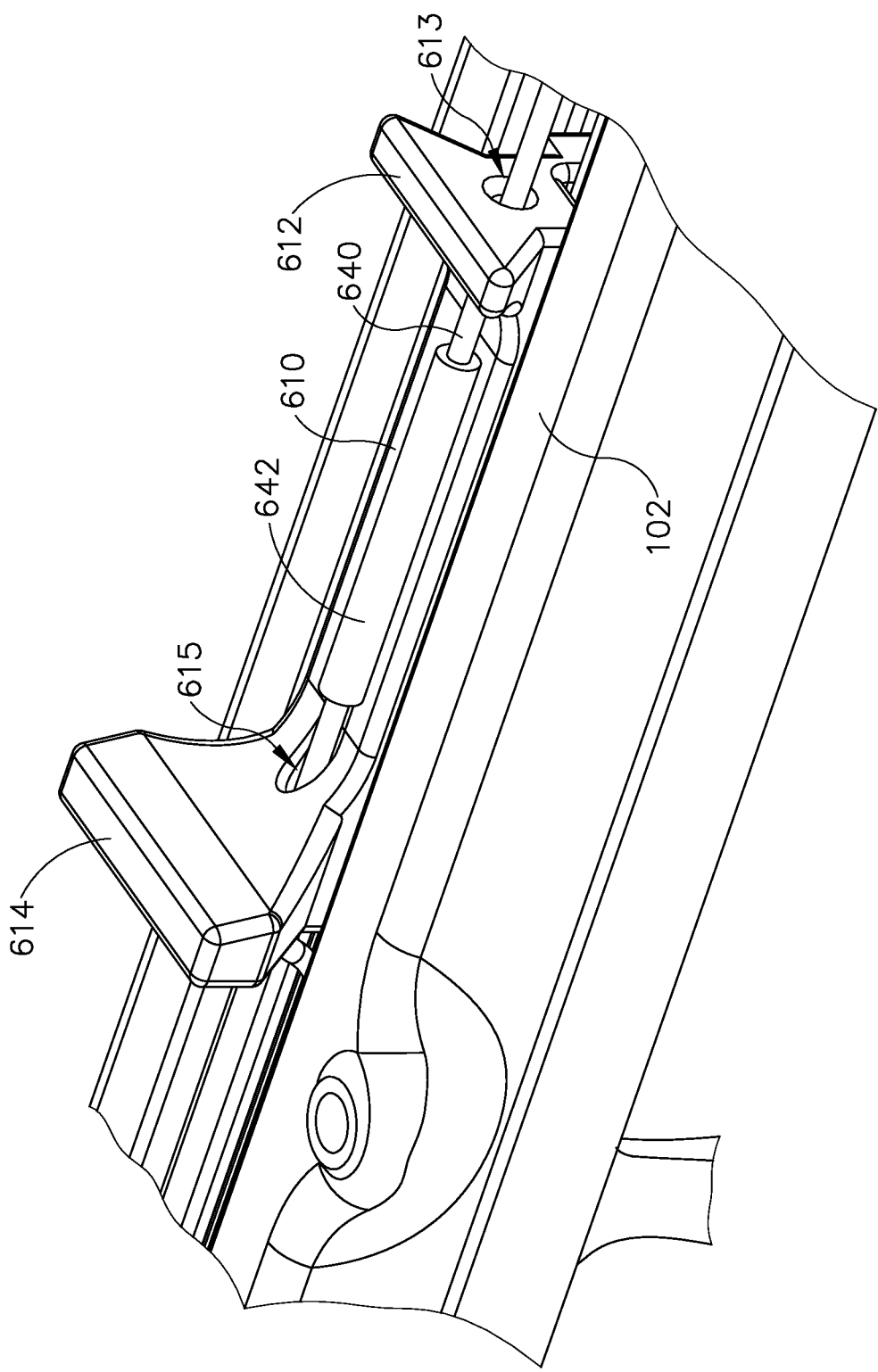
FIG. 43 depicts a detailed perspective view of the instrument of FIG. 33 with another exemplary alternative guidewire.

FIG. 41 shows another exemplary guidewire (630). Guidewire (630) of this example comprises a hypotube (632) that is secured between two segments of guidewire (630) to thereby provide additional lateral strength to guidewires (630). In other words, hypotube (632) is longitudinally interposed between two segments of guidewire (630) and is fixedly secured to those segments. Hypotube (632) is disposed within a portion of guidewire (630) between cantle and pommel portions (612, 614). FIG. 42 shows yet another exemplary guidewire (640). Guidewire (640) of this example comprises a hypotube (642) that is secured about guidewire (640) to thereby provide additional lateral strength to guidewire (640). As with hypotube (632), hypotube (642) of this example is disposed about a portion of guidewire (640) between cantle and pommel portions (612, 614). As shown in FIG. 43, in order to provide even more lateral strength to guidewire (640), the thickness of hypotube (642) may be increased to thereby increase the additional strength provided to guidewire (640). In the present example, each hypotube (632, 642) is formed of steel or some other metal. It should be understood, however, that hypotube (632, 642) may be formed of a plastic and/or any other suitable material(s).

Figure 44:
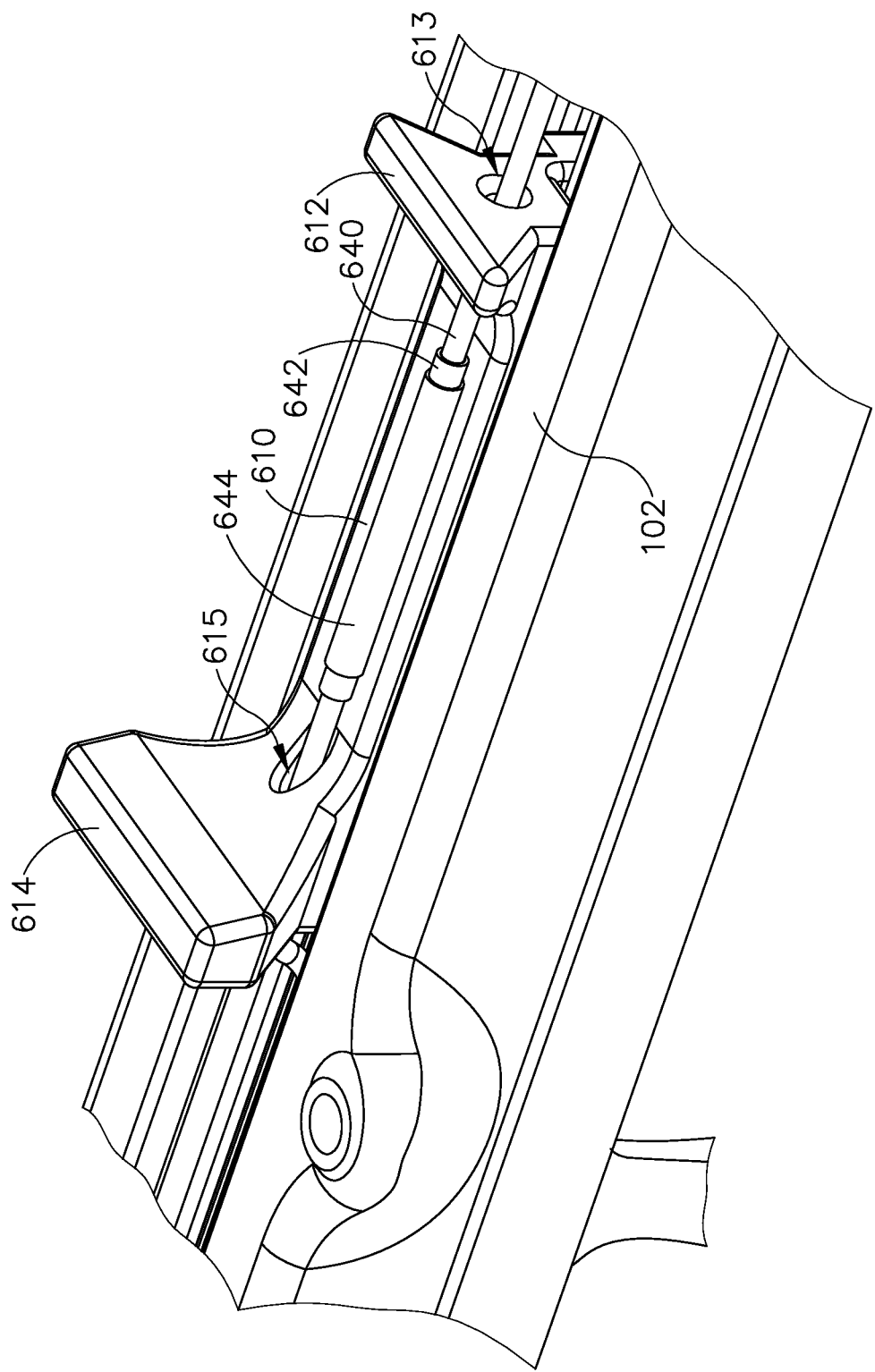
FIG. 44 depicts a detailed perspective view of the instrument of FIG. 33 with another exemplary alternative guidewire.

It may also be desirable to provide additional friction to guidewires (106, 620, 630, 640) so as to prevent slipping between the operator's fingers and guidewires (106, 620, 630, 640). For instance, an exterior surface of guidewires (106, 620, 630, 640) and/or hypotubes (632, 642) may be provided with a coating, sleeve, and/or other feature(s) that is/are configured to prohibit slipping between the operator's fingers and guidewires (106, 620, 630, 640). For instance, the coating, sleeve, and/or other feature(s) may provide for a rough or sticky surface. Additionally or alternatively, guidewires (106, 620, 630, 640) may comprise a grip (644) disposed about guidewires (106, 620, 630, 640) and/or hypotubes (632, 642) as shown in FIG. 44. For instance, grip (644) may comprise a rough or sticky exterior surface. In some versions, grip (644) comprises an elastomeric material such as silicone rubber. It should be understood that, in versions having a high friction material, it may be desirable to provide a gap between the high friction material and body (610) of guidewire movement mechanism (600). Other suitable variations will be apparent to those of ordinary skill in the art in view of the teachings herein.

C. Exemplary Proximally Extending Guidewire Movement Mechanism

In the examples described above, guidewire (106) deviates from the longitudinal axis that is shared by guide catheter (104) and dilation catheter (108) in order to engage guidewire movement mechanism (112, 300, 400, 450, 500). After exiting guidewire movement mechanism (112, 300, 400, 450, 500), guidewire (106) is eventually aligned along the longitudinal axis that is shared by guide catheter (104) and dilation catheter (108); but guidewire (106) is nevertheless laterally offset from that longitudinal axis in the region where guidewire (106) engages guidewire movement mechanism (112, 300, 400, 450, 500). In some instances, this offset may reduce the ability of the operator to sense forces being encountered at the distal end of guidewire (106). In addition or in the alternative, this offset may create a whipping effect when guidewire (106) is rotated about the longitudinal axis of guidewire (106), due to regions of guidewire (106) storing and then suddenly releasing torque as a proximal portion of guidewire (106) is rotated. It may therefore be desirable to provide a guidewire movement mechanism that engages guidewire (106) along the same longitudinal axis that is shared by guide catheter (104) and dilation catheter (108), eliminating a need for guidewire (106) to deviate from that longitudinal axis in order to engage the guidewire movement mechanism. This may reduce the amount of stored torque that is built up within guidewire (106) and provide for improved rotational control of guidewire (106). It may still be desirable to provide a control feature for guidewire movement mechanism that may be engaged by the operator at a location that is offset from the longitudinal axis that is shared by guide catheter (104), dilation catheter (108), and guidewire (106); while still providing engagement between the guidewire movement mechanism and guidewire (106) along that longitudinal axis.

FIGS. 45-48 show an exemplary guidewire movement mechanism (700) that engages guidewire (106) at the longitudinal axis that is shared by guide catheter (104), dilation catheter (108), and guidewire (106); while providing a control feature that may be engaged by the operator at a location that is offset from the longitudinal axis that is shared by guide catheter (104), dilation catheter (108), and guidewire (106). Guidewire movement mechanism (700) is operable to longitudinally advance and retract guidewire (106) relative to handle (102), through guidewire support (118), and through the lumen of dilation catheter (108) by longitudinally sliding guidewire movement mechanism (700) along the length of handle (102). Guidewire movement mechanism (700) further comprises a rotation mechanism such as a gear box (710) that is operable to rotate guidewire (106) about the longitudinal axis of guidewire (106).

Figure 45:
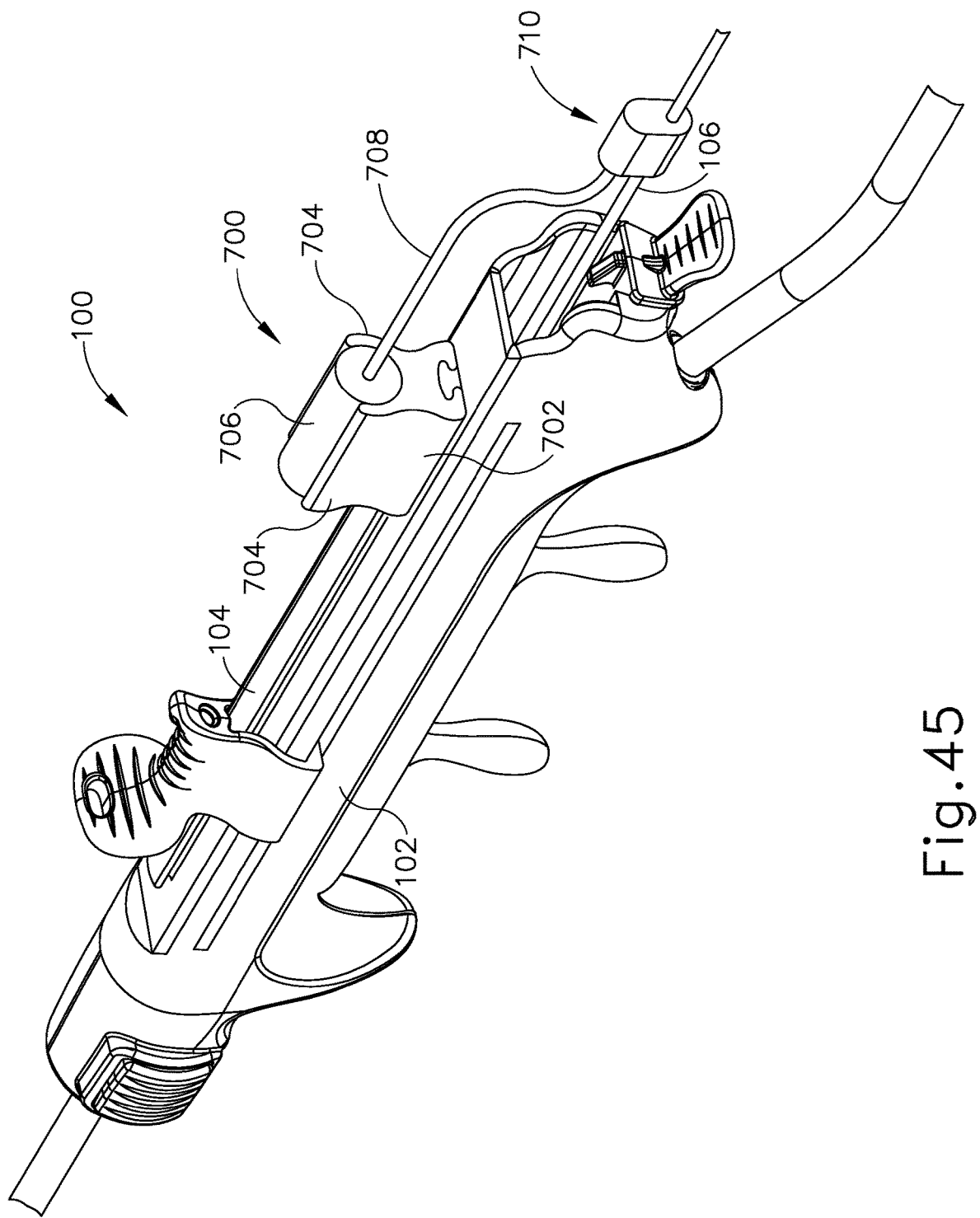
FIG. 45 depicts a perspective view of another exemplary instrument suitable for incorporation into the dilation catheter system of FIG. 1.
Figure 46:
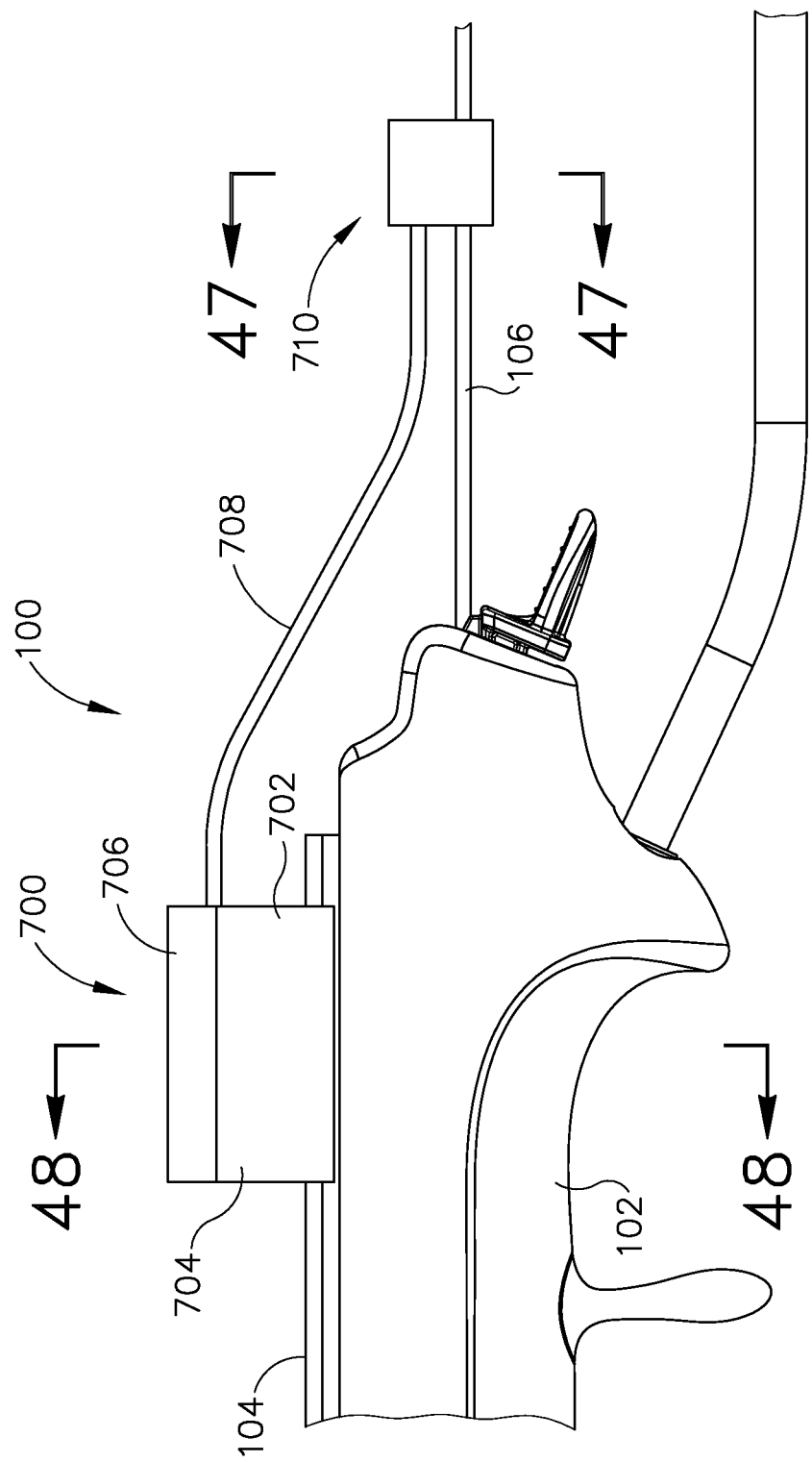
FIG. 46 depicts a detailed side elevational view of a proximal end of the instrument of FIG. 45.

As best seen in FIGS. 45-46, guidewire movement mechanism (700) of the present example comprises a body (702), a rotary member (706), a proximally extending arm (708), and a gear box (710). Body (702) comprises a pair of arcuate flanges (704) that are configured to rotatably receive and support rotary member (706). Rotary member (706) is thus rotatable relative to body (702) and is exposed for direct contact and engagement by an operator's finger. Arm (708) extends between rotary member (706) and gear box (710). Arm (708) has sufficient rigidity to provide unitary translation of body (702), arm (708), and gear box (710). Gear box (710) is located at the proximal end of arm (708) and is secured to guidewire (106) such that guidewire (106) translates longitudinally with the assembly formed by body (702), arm (708), and gear box (710). However, gear box (710) also permits guidewire (106) to rotate within gear box (710), as will be described in greater detail below. Handle (102) of the present example comprises a track (105) projecting from a top surface of handle (102). Body (702) is configured to slidably couple with track (105) such that guidewire movement mechanism (700) may be slid along the length of handle (102) to thereby translate guidewire longitudinally (106). Of course, guidewire movement mechanism (700) may be coupled with handle (102) in any other suitable fashion.

Figure 47:
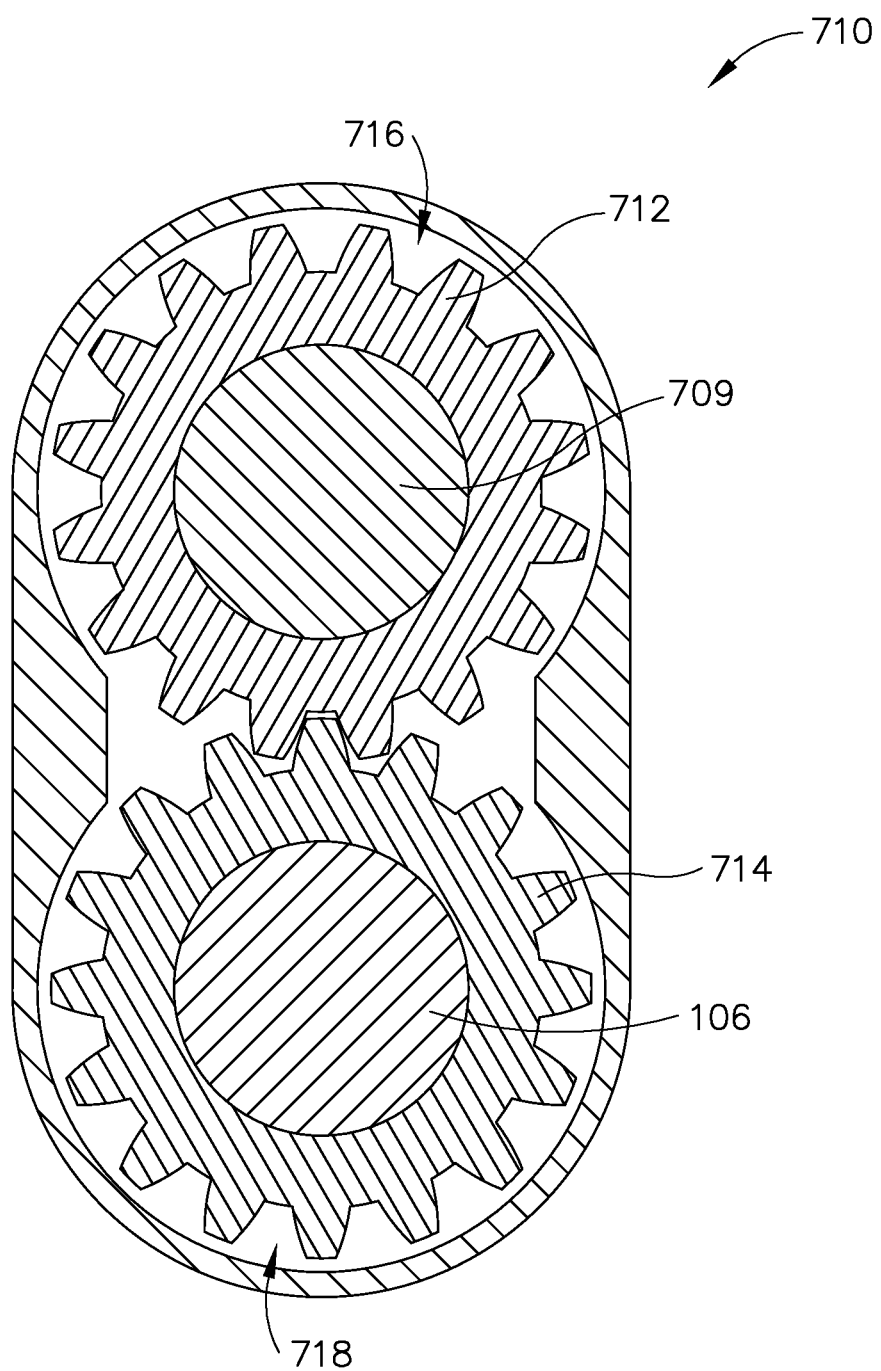
FIG. 47 depicts a cross-sectional rear view of a rotary assembly of the instrument of FIG. 45, taken along line 47-47 of FIG. 46.
Figure 48:
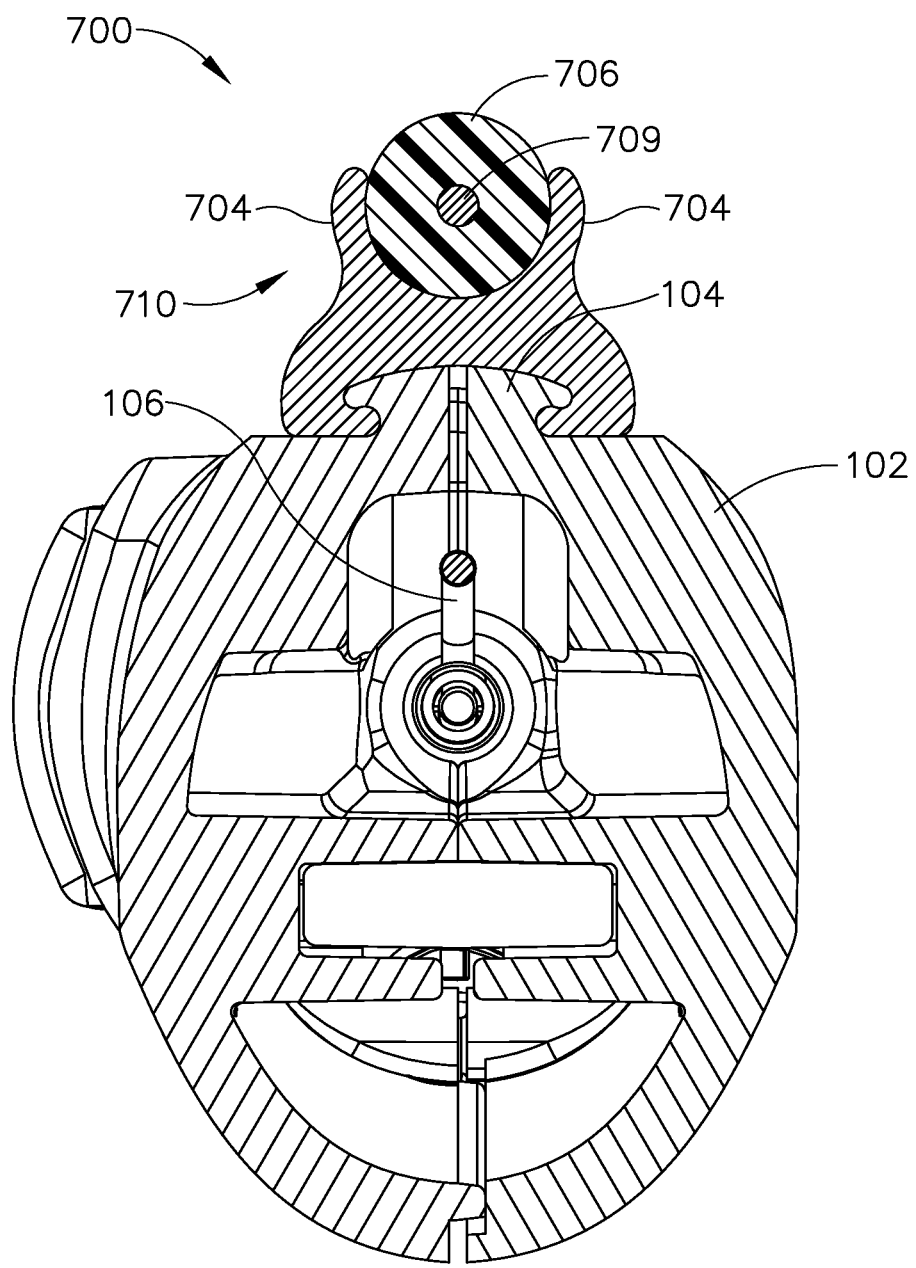
FIG. 48 depicts a cross-sectional rear view of the instrument of FIG. 45, taken along line 48-48 of FIG. 46.
Figure 49:
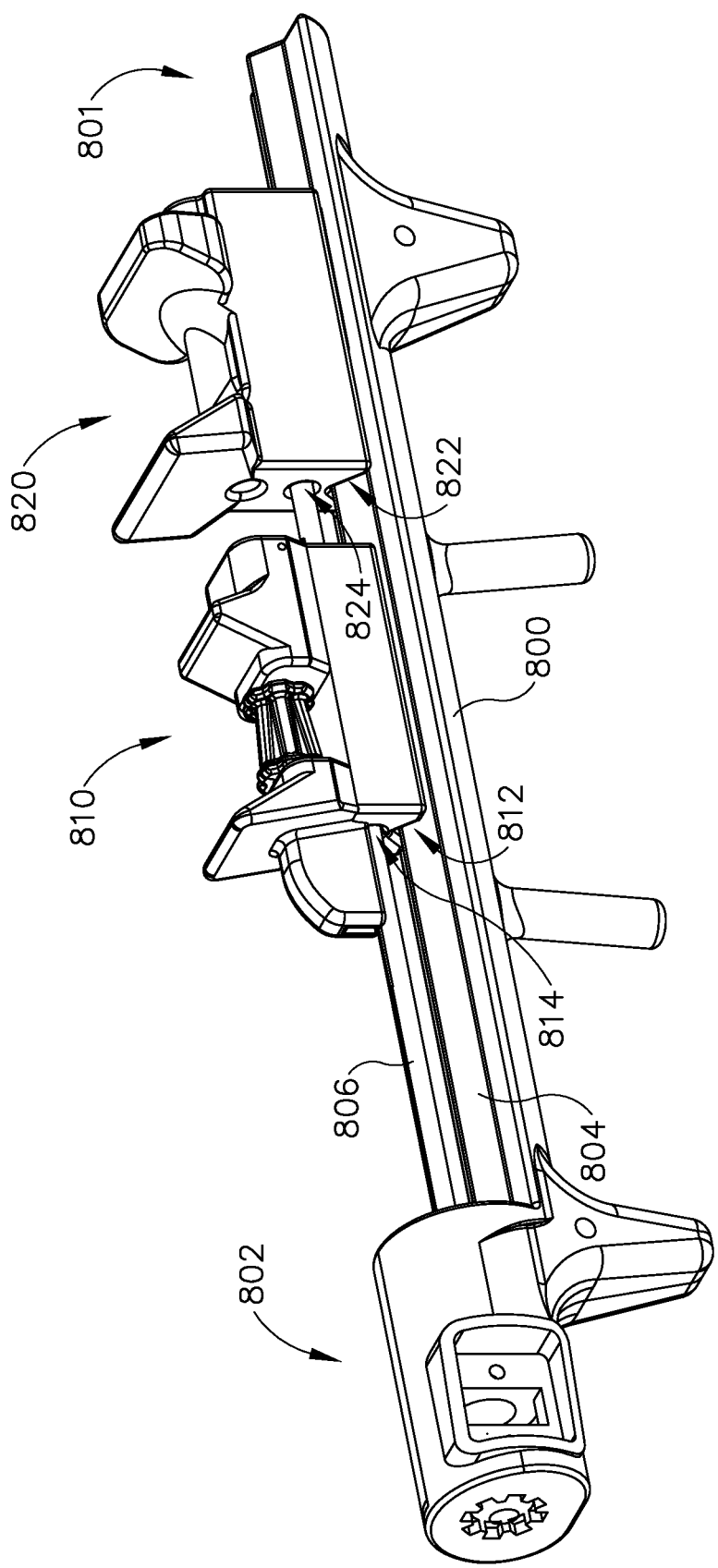
FIG. 49 depicts a perspective view of another exemplary instrument suitable for incorporation into the dilation catheter system of FIG. 1.
Figure 50:
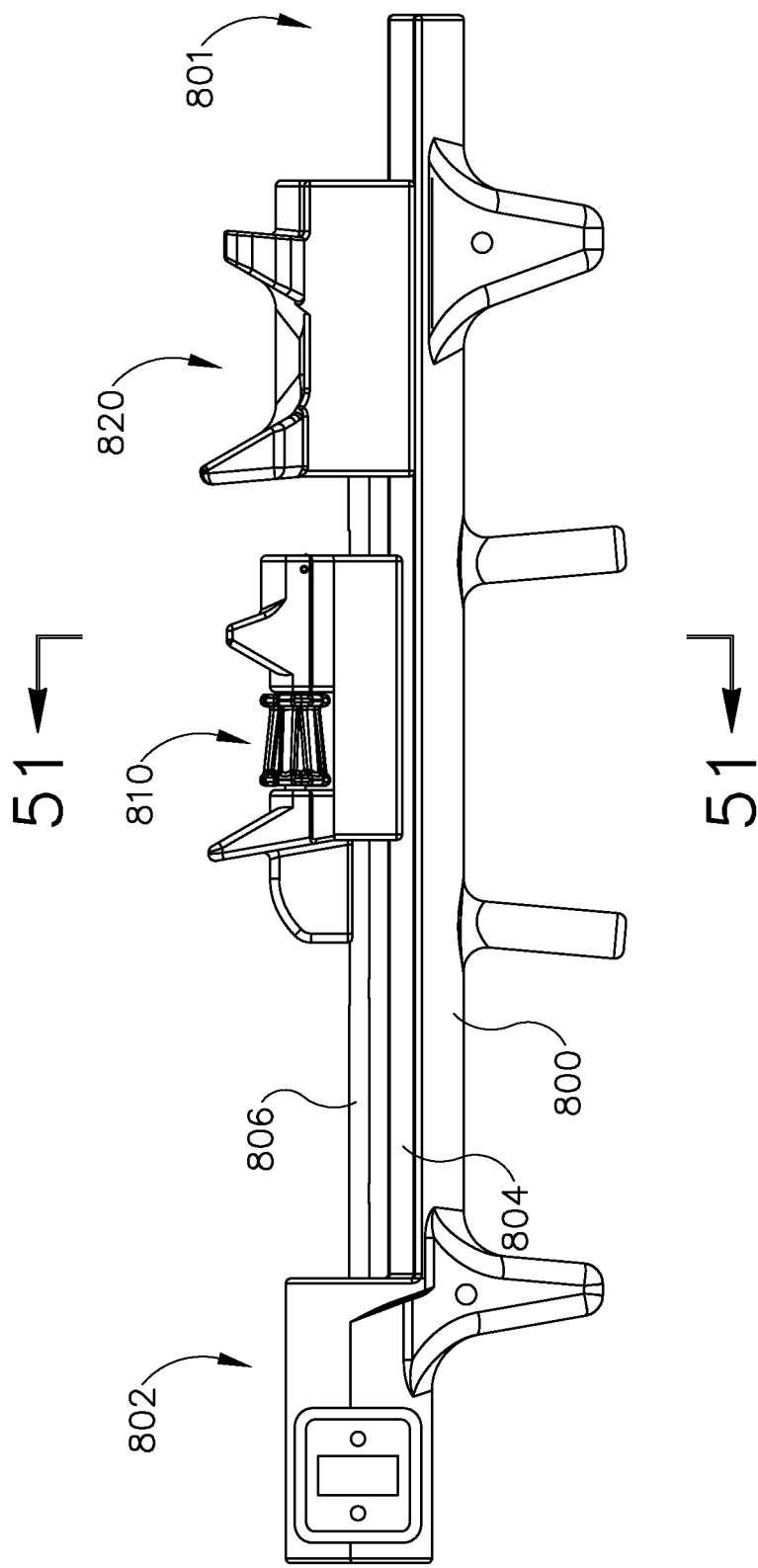
FIG. 50 depicts a side elevational view of the instrument of FIG. 49.

A torque cable (709) is rotatably supported in arm (708). As best seen in FIG. 48, a distal end of torque cable (709) is unitarily secured within rotary member (706) such that torque cable (709) rotates unitarily with rotary member (706). As best seen in FIG. 47, a proximal end of torque cable (709) is unitarily secured within a first gear (712) of gear box (710), such that first gear (712) rotates unitarily with torque cable (709). As also seen in FIG. 47, gear box (710) further comprises a second gear (714). Gears (712, 714) are both rotatably secured within gear box (710). Teeth (716) of first gear (712) mesh with teeth (718) of second gear (714) such that rotation of first gear (712) causes concurrent rotation of second gear (714) and vice versa. Second gear (714) is disposed about and is unitarily coupled to guidewire (106) at a position proximal to handle (102) such that rotation of second gear (714) causes concurrent rotation of guidewire (106). Thus, it should be appreciated that rotation of rotary member (706) causes rotation of guidewire (106) via torque cable (709) and gears (712, 714).

Because of the position of gear box (710) (as best seen in FIGS. 45-46) in this example, guidewire (106) is able to pass through handle (102) in a substantially straight manner, along the same longitudinal axis that is shared by guide catheter (104), dilation catheter (108), and guidewire (106). Gear (714) is centered on this longitudinal axis. It should be understood that the positioning of gear (714) on this longitudinal axis may provide the operator with more sensitive tactile feedback as the operator drives rotation of guidewire (106) via rotary member (706).

D. Exemplary Instrument Guidewire Movement Mechanism

In some versions of instrument (100), it may be desirable to provide handle (102), guidewire movement mechanism (112), and/or dilation catheter movement actuator (114) with alternative features that are configured to provide a slidable interface between guidewire movement mechanism (112) and handle (102); and between dilation catheter movement actuator (114) and handle (102). FIGS. 49-54 show such an exemplary handle (800), a guidewire movement mechanism (810), and a dilation catheter movement actuator (820). Guidewire movement mechanism (810) is configured to operate substantially similar to guidewire movement mechanism (112) discussed above except for the differences discussed below. In particular, guidewire movement mechanism (810) is operable to longitudinally advance and retract guidewire (106) relative to handle (800) and through the second lumen of dilation catheter (108) by longitudinally sliding guidewire movement mechanism (810) along the length of handle (800). Dilation catheter movement actuator (820) is configured to operate substantially similar to dilation catheter movement actuator (114) discussed above except for the differences discussed below. In particular, dilation catheter movement actuator (820) is operable to longitudinally advance and retract dilation catheter (108) relative to handle (800) and through the lumen of guide catheter (104) by longitudinally sliding dilation catheter movement actuator (820) along handle (800).

Figure 51:
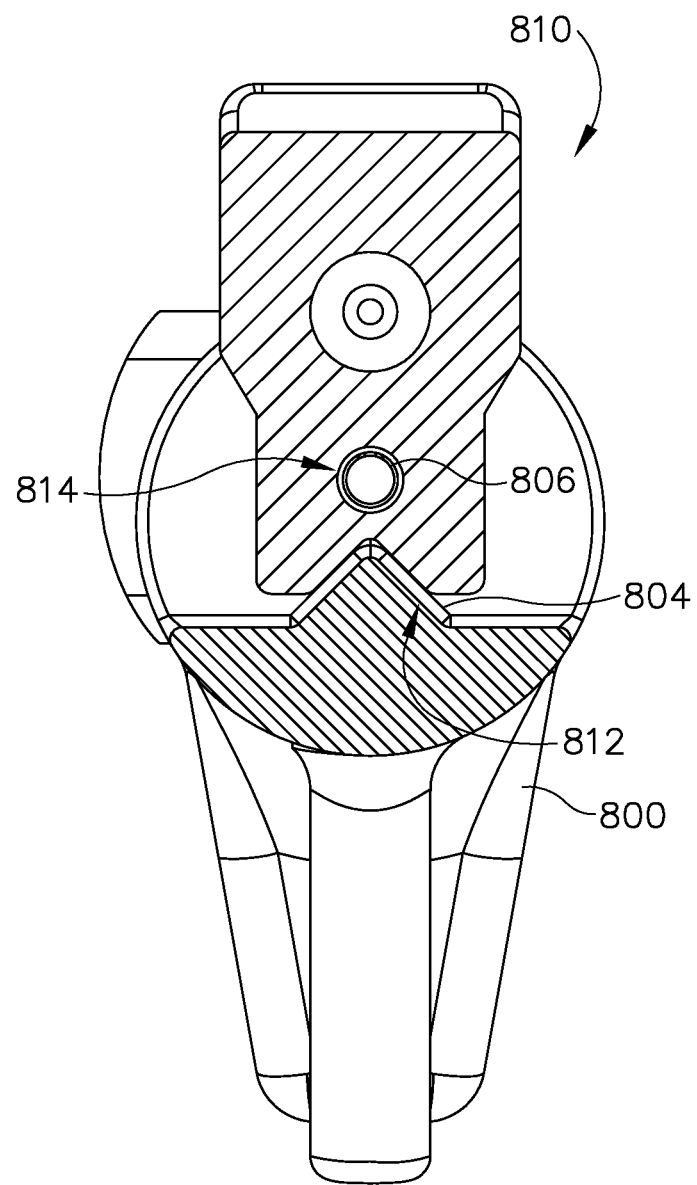
FIG. 51 depicts a cross-sectional rear view of the instrument of FIG. 49, taken along line 51-51 of FIG. 50.
Figure 52:
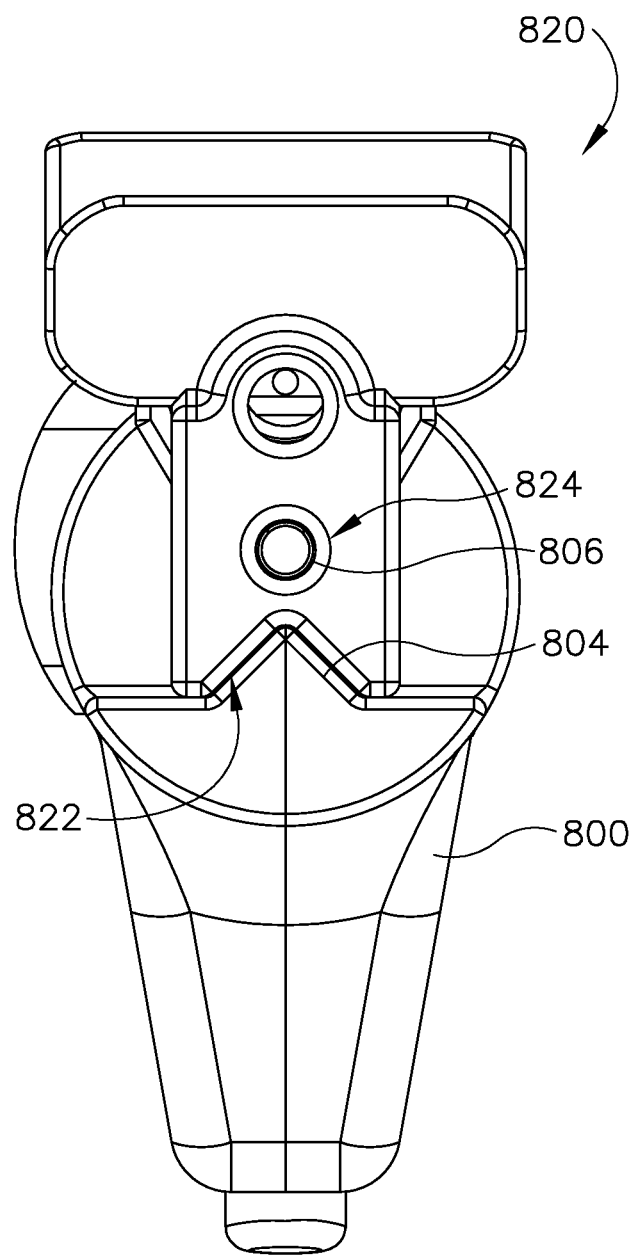
FIG. 52 depicts a rear elevational view of the instrument of FIG. 49.
Figure 53:
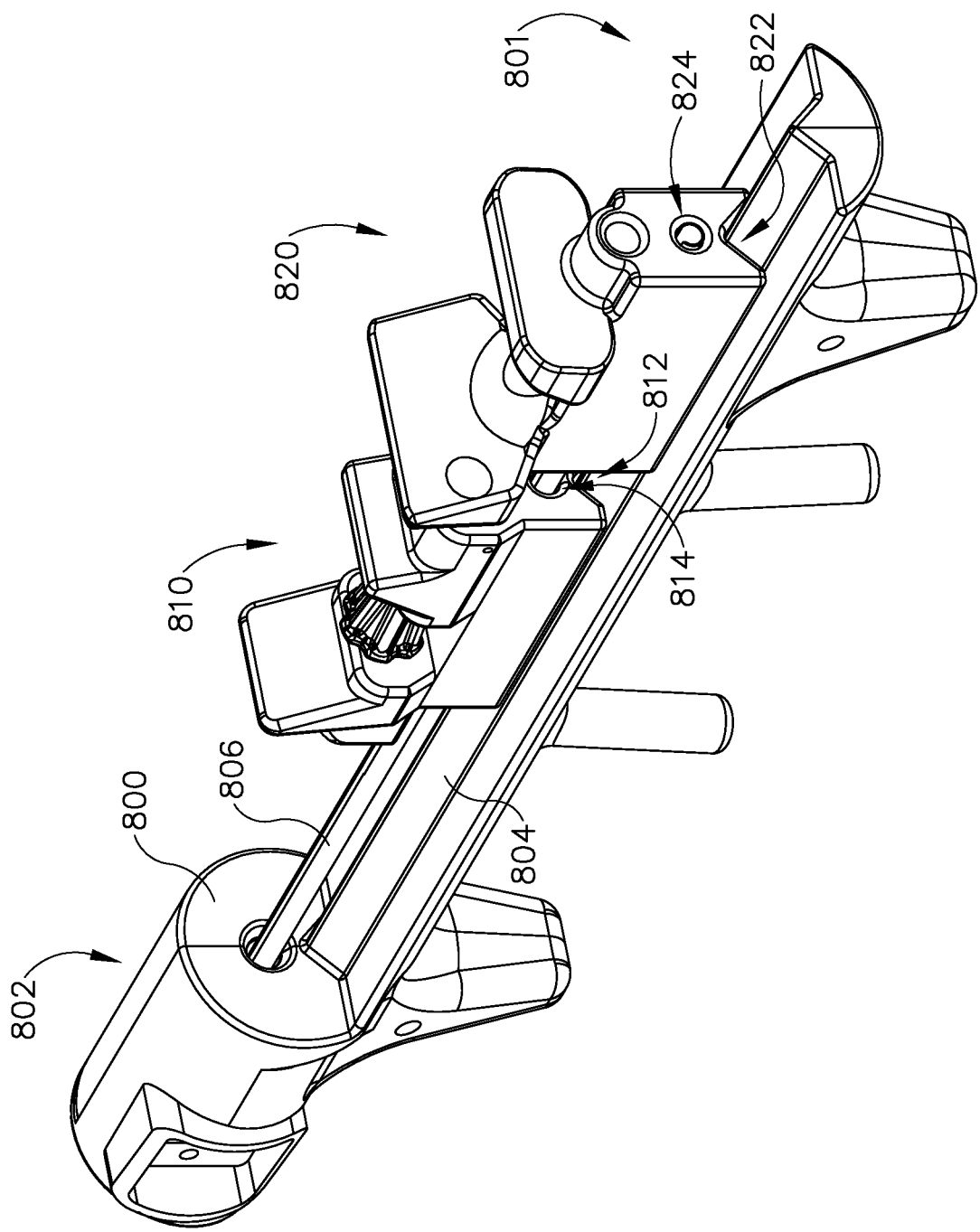
FIG. 53 depicts another perspective view of the instrument of FIG. 49.

Handle (800) includes a proximal end (801), a distal end (802), and an elongate track (804) extending from a top surface of handle (800). As best seen in FIGS. 51 and 52, track (804) has a triangular cross-sectional profile. Handle (800) further comprises a rigid shaft (806) extending proximally from a distal portion of handle (800). As will be discussed in more detail below, guidewire movement mechanism (810) and dilation catheter movement actuator (820) are configured to slidably couple with track (804) and shaft (806) such that guidewire movement mechanism (810) and dilation catheter movement actuator (820) may slide along the length of track (804) and shaft (806), with track (804) and shaft (806) providing guidance and support to guidewire movement mechanism (810) and dilation catheter movement actuator (820). Shaft (806) may be configured to slidably receive a dilation catheter (108), with dilation catheter (108) being slidably received in guide catheter (104), and with guidewire (106) being slidably received in dilation catheter (108). It should therefore be understood that guide catheter (104), dilation catheter (108), shaft (806), and at least a portion of guidewire (106) may all be coaxially aligned on the same longitudinal axis. In some versions, shaft (806) is substantially identical to guidewire support (118) described above. By way of example only, shaft (806) may comprise a hypotube with a slit formed therein to transversely receive guidewire (106).

Figure 54:
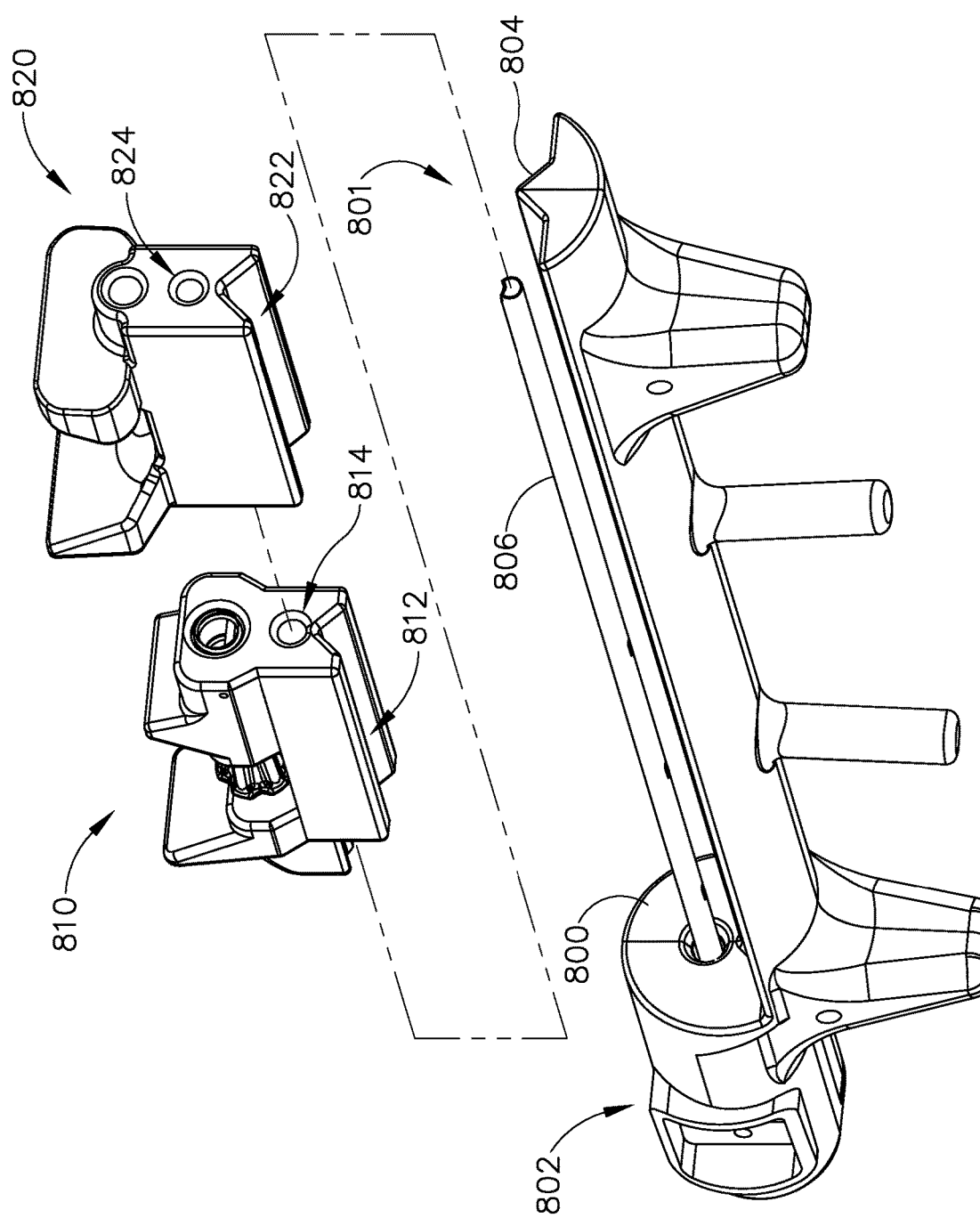
FIG. 54 depicts a partially exploded perspective view of the instrument of FIG. 49.
Figure 55:
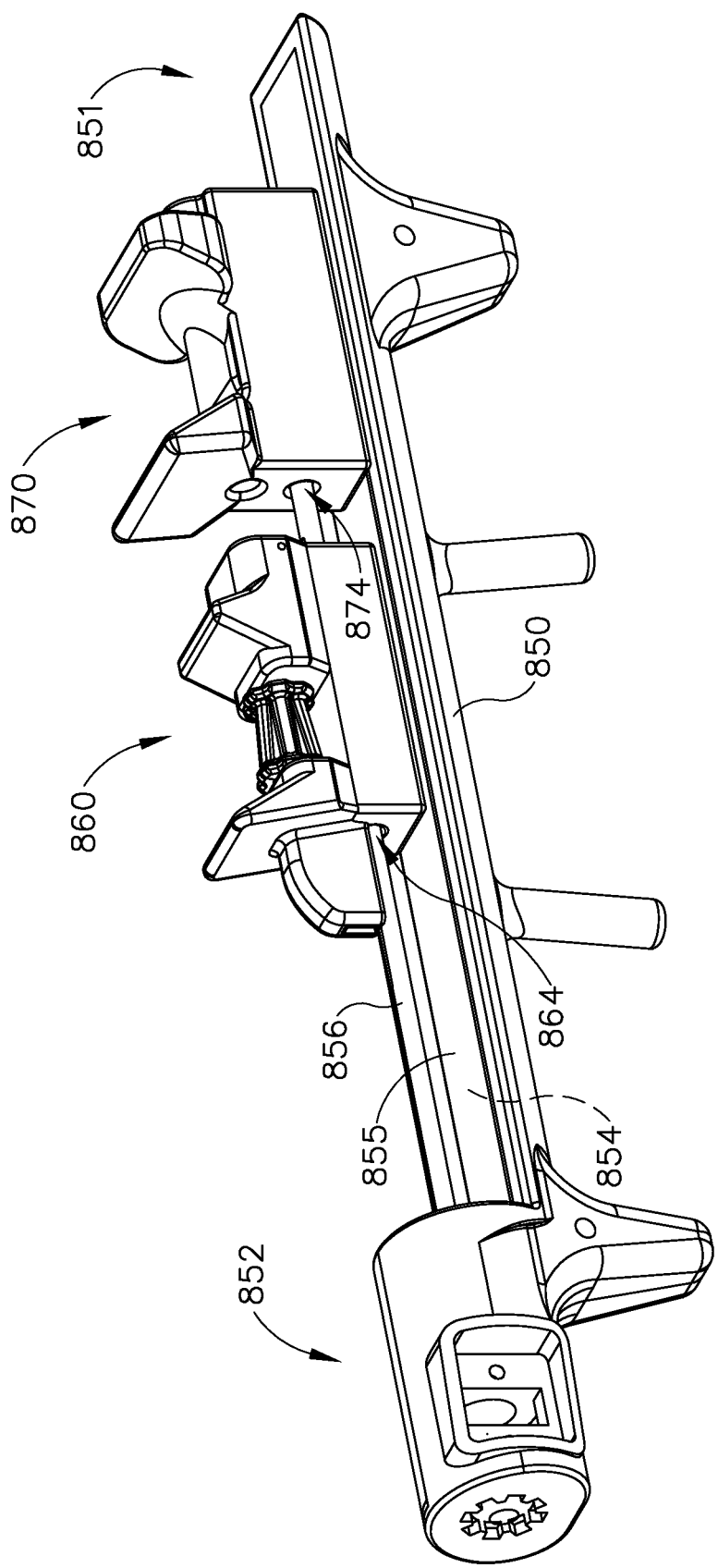
FIG. 55 depicts a perspective view of another exemplary instrument suitable for incorporation into the dilation catheter system of FIG. 1.
Figure 56:
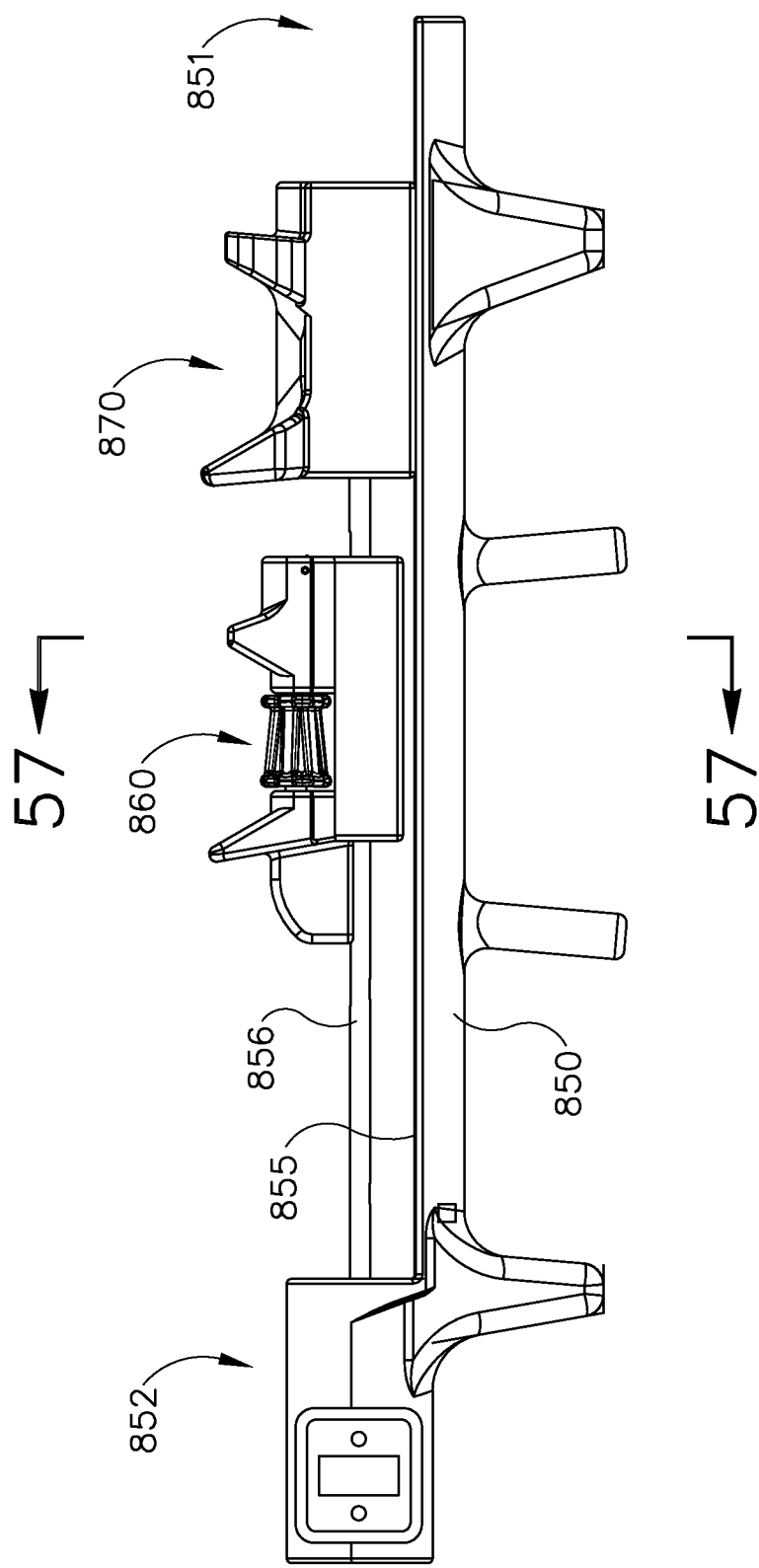
FIG. 56 depicts a side elevational view of the instrument of FIG. 55.

Guidewire movement mechanism (810) is secured to guidewire (106). As with guidewire movement mechanism (112) discussed above, guidewire movement mechanism (810) is operatively disposed on handle (800) and is operable to longitudinally advance and retract guidewire (106) by longitudinally sliding guidewire movement mechanism (810) along the length of track (804) and shaft (806). Guidewire movement mechanism (810) is also operable to rotate guidewire (106) about the longitudinal axis of guidewire (106). Guidewire movement mechanism (810) defines an elongate recess (812) formed in a bottom surface of guidewire movement mechanism (810). As best seen in FIGS. 51 and 54, recess (812) has a triangular cross-sectional profile complementing that of track (804). Recess (812) is configured to slidably receive track (804) of handle (800) such that guidewire movement mechanism (810) may be slid along the length of track (804). Furthermore, guidewire movement mechanism (810) slidably receives shaft (806) within a circular opening (814) such that guidewire movement mechanism (810) may be slid along the length of shaft (806).

Dilation catheter movement actuator (820) is secured to dilation catheter (108). As with dilation catheter movement actuator (114) discussed above, dilation catheter movement actuator (820) is operatively disposed on handle (800) and is operable to longitudinally advance and retract dilation catheter (108) by longitudinally sliding dilation catheter movement actuator (820) along the length of track (804) and shaft (806). Dilation catheter movement actuator (820) defines an elongate recess (822) formed in a bottom surface of dilation catheter movement actuator (820). As best seen in FIGS. 52 and 54, recess (822) has a triangular cross-sectional profile complementing that of track (804). Recess (822) is configured to slidably receive track (804) of handle (800) such that dilation catheter movement actuator (820) may be slid along the length of track (804). Furthermore, dilation catheter movement actuator (820) slidably receives shaft (806) within a circular opening (824) such that dilation catheter movement actuator (820) may be slid along the length of shaft (806).

FIGS. 55-60 show another exemplary handle (850), a guidewire movement mechanism (860), and a dilation catheter movement actuator (870). Guidewire movement mechanism (860) is configured to operate substantially similar to guidewire movement mechanism (112) discussed above except for the differences discussed below. In particular, guidewire movement mechanism (860) is operable to longitudinally advance and retract guidewire (106) relative to handle (850) and through the second lumen of dilation catheter (108) by longitudinally sliding guidewire movement mechanism (860) along the length of handle (850). Dilation catheter movement actuator (870) is configured to operate substantially similar to dilation catheter movement actuator (114) discussed above except for the differences discussed below. In particular, dilation catheter movement actuator (870) is operable to longitudinally advance and retract dilation catheter (108) relative to handle (850) and through the lumen of guide catheter (104) by longitudinal sliding of dilation catheter movement actuator (870) along handle (850).

Handle (850) includes a proximal end (851), a distal end (852), and an elongate magnet (854) (or series of magnets (854)) disposed within handle (850) beneath a top surface (855) of handle (850). Handle (850) further comprises a rigid shaft (856) extending proximally from a distal portion of handle (850). As will be discussed in more detail below, guidewire movement mechanism (860) and dilation catheter movement actuator (870) are configured to slidably associate with magnet (854) and shaft (856) such that guidewire movement mechanism (860) and dilation catheter movement actuator (870) may slide along the length of magnet (854) and shaft (856). Shaft (856) may be configured to slidably receive a dilation catheter (108), with dilation catheter (108) being slidably received in guide catheter (104), and with guidewire (106) being slidably received in dilation catheter (108). It should therefore be understood that guide catheter (104), dilation catheter (108), shaft (856), and at least a portion of guidewire (106) may all be coaxially aligned on the same longitudinal axis. In some versions, shaft (856) is substantially identical to guidewire support (118) described above. By way of example only, shaft (856) may comprise a hypotube with a slit formed therein to transversely receive guidewire (106).

Figure 57:
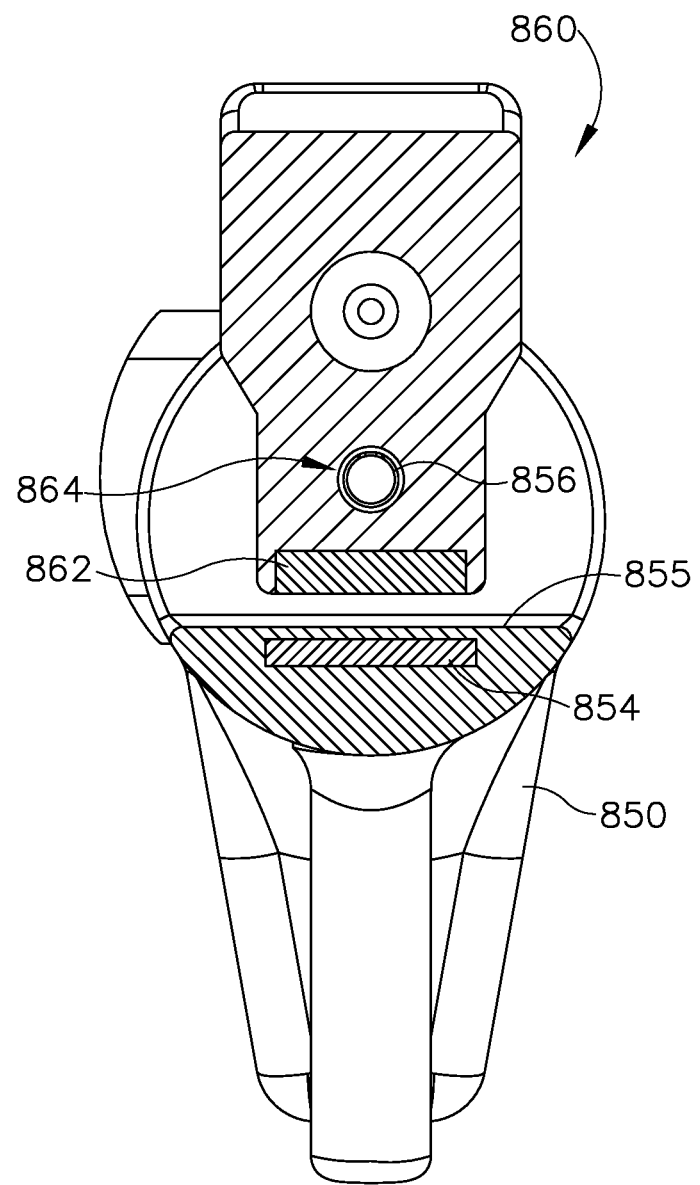
FIG. 57 depicts a cross-sectional rear view of the instrument of FIG. 55, taken along line 57-57 of FIG. 56.
Figure 58:
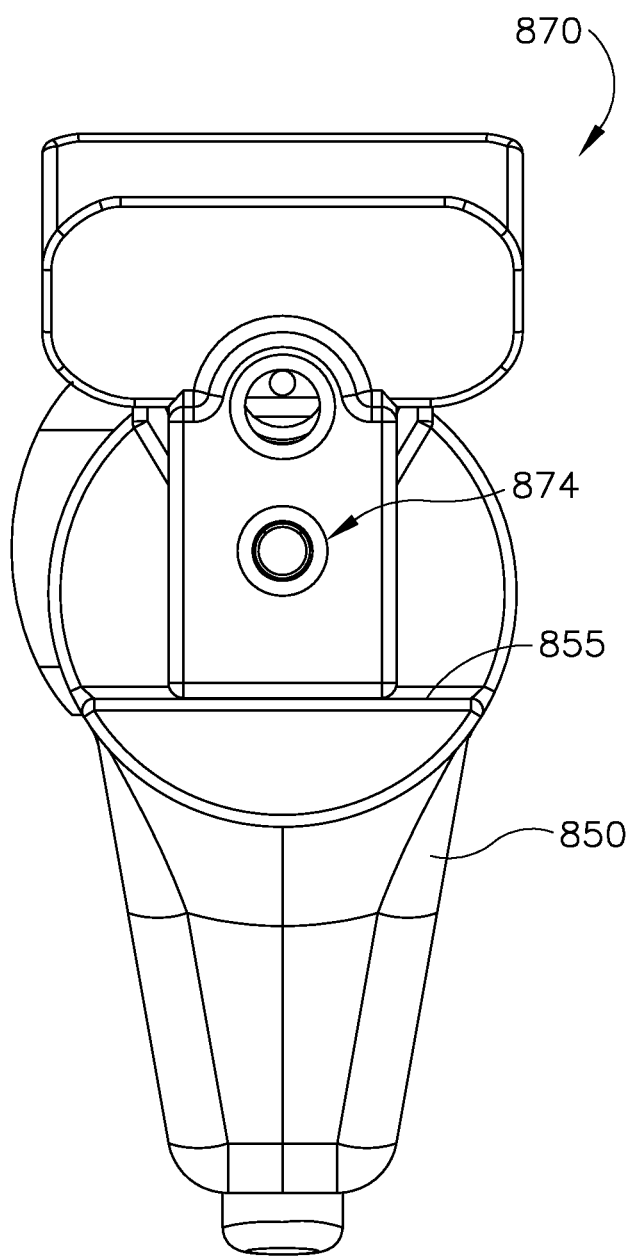
FIG. 58 depicts a rear elevational view of the instrument of FIG. 55.
Figure 59:
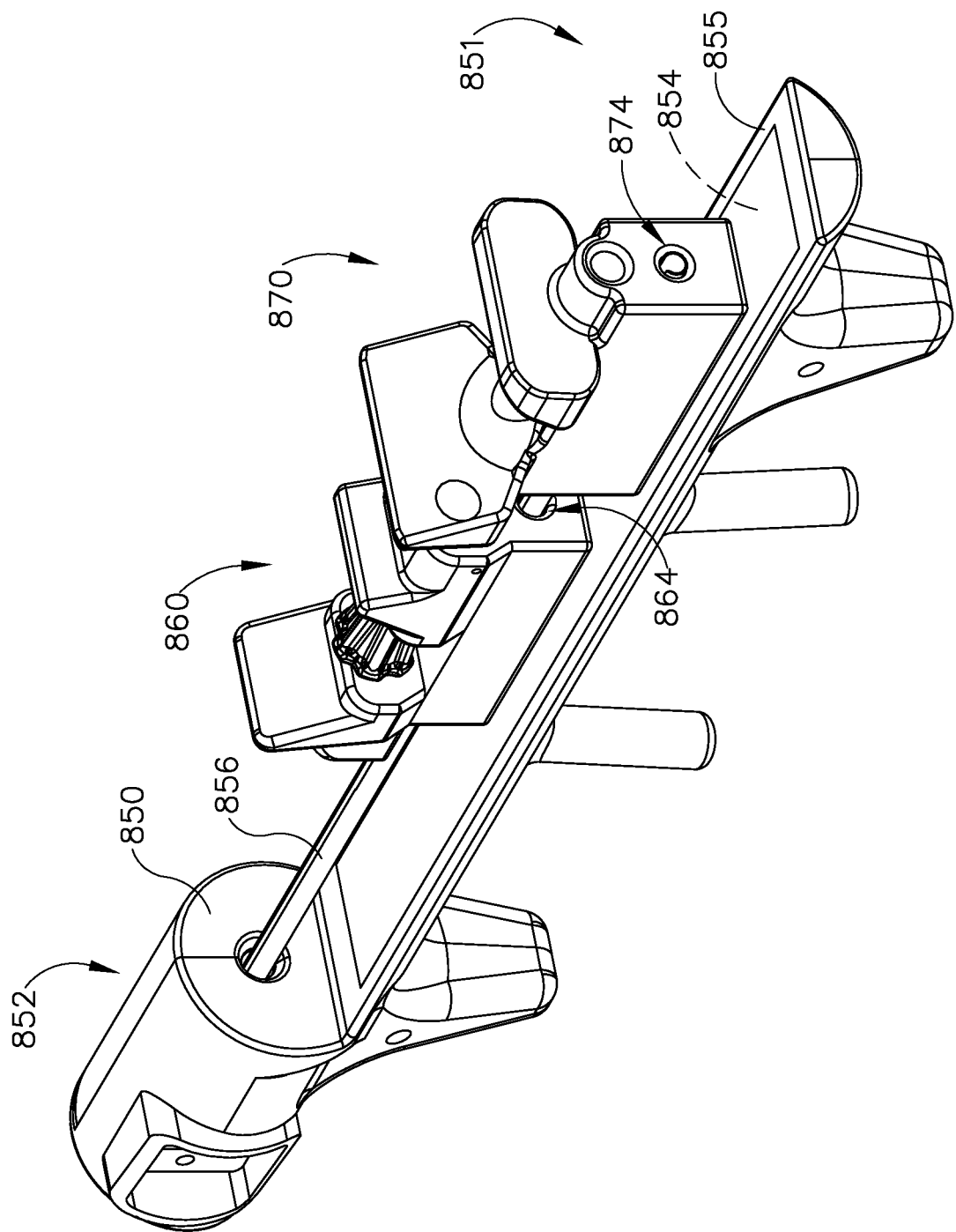
FIG. 59 depicts another perspective view of the instrument of FIG. 55.
Figure 60:
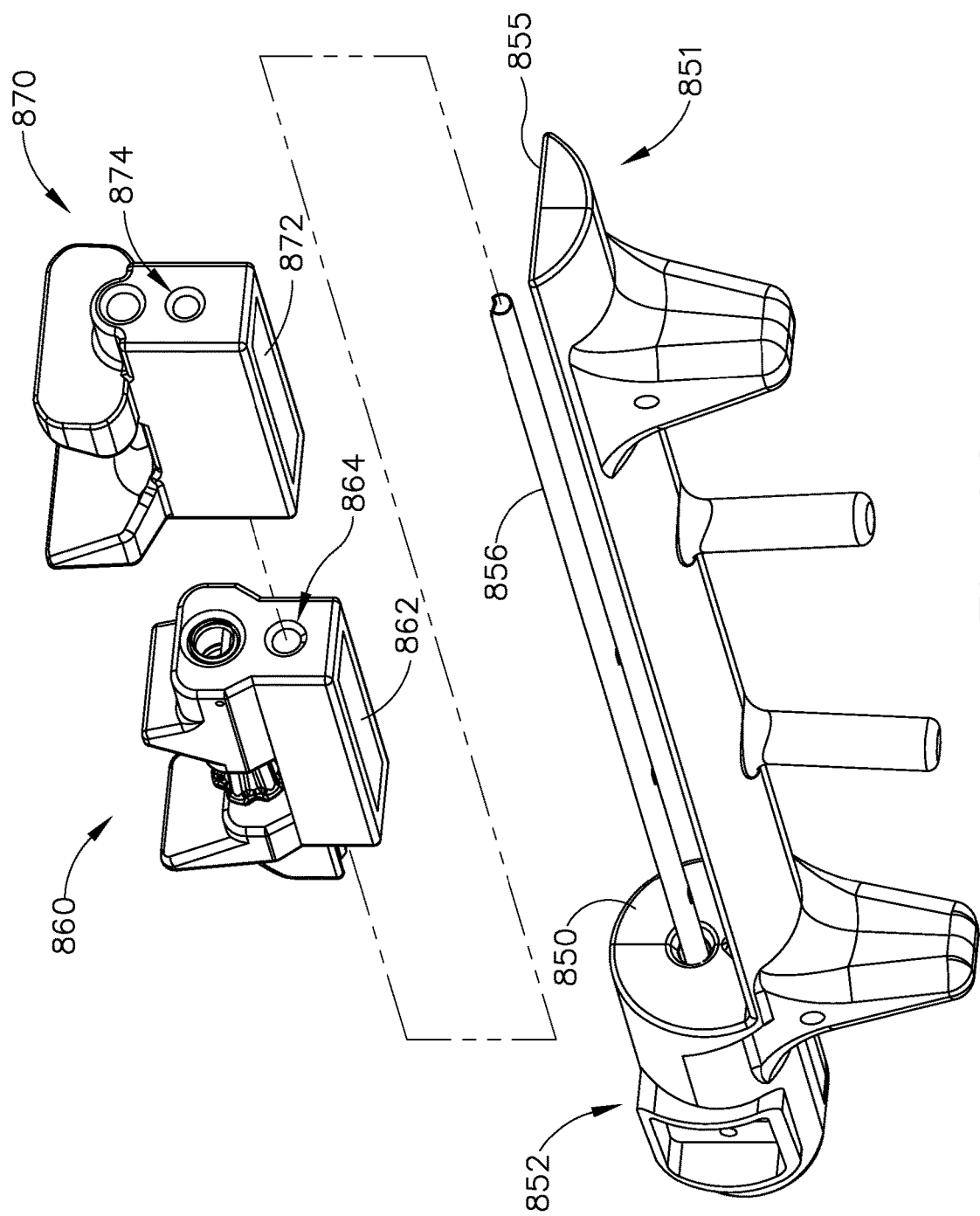
FIG. 60 depicts a partially exploded perspective view of the instrument of FIG. 55.
Figure 61:
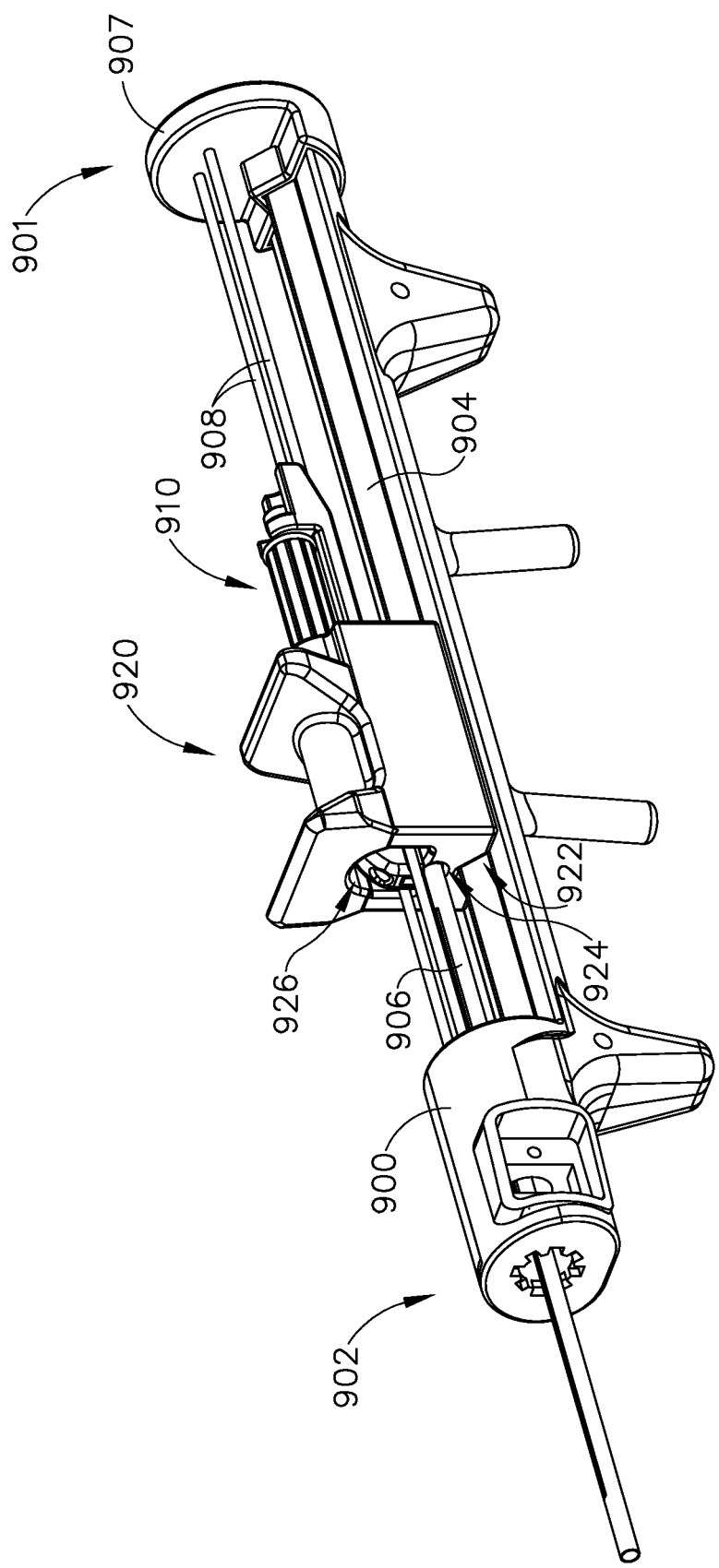
FIG. 61 depicts a perspective view of another exemplary instrument suitable for incorporation into the dilation catheter system of FIG. 1.
Figure 62:
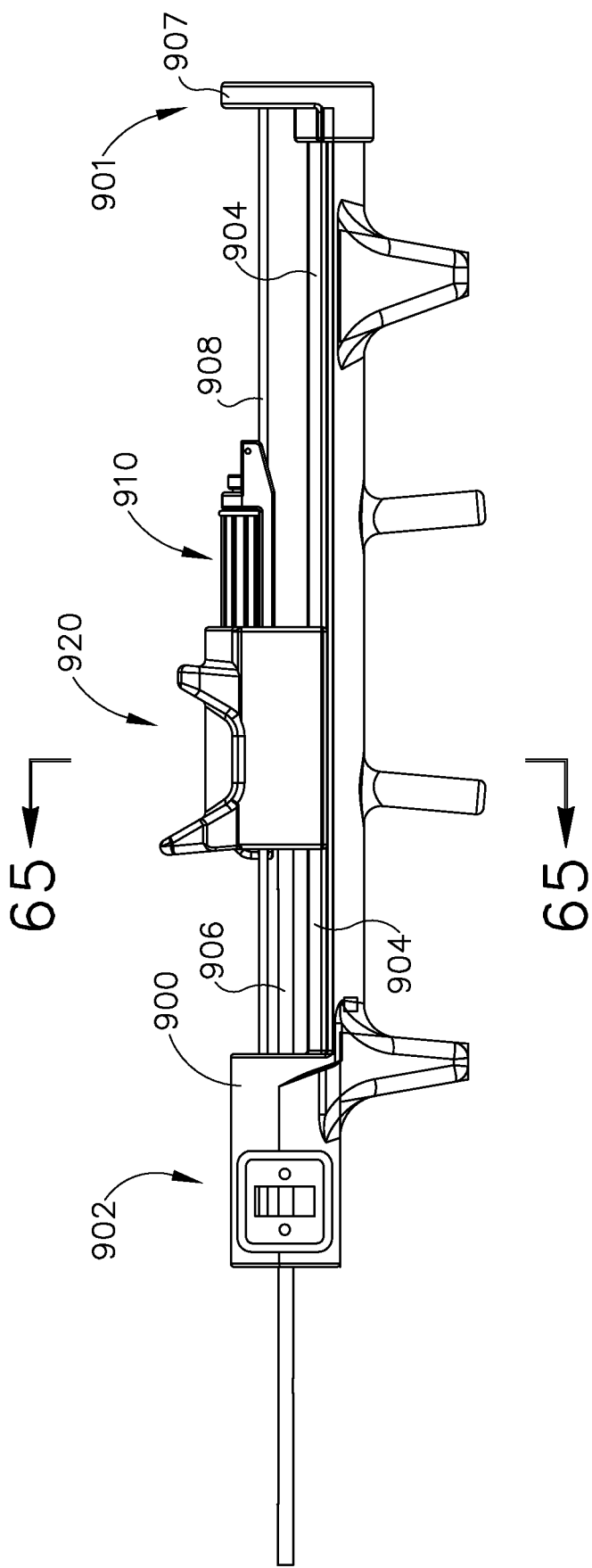
FIG. 62 depicts a side elevational view of the instrument of FIG. 61.
Figure 63:
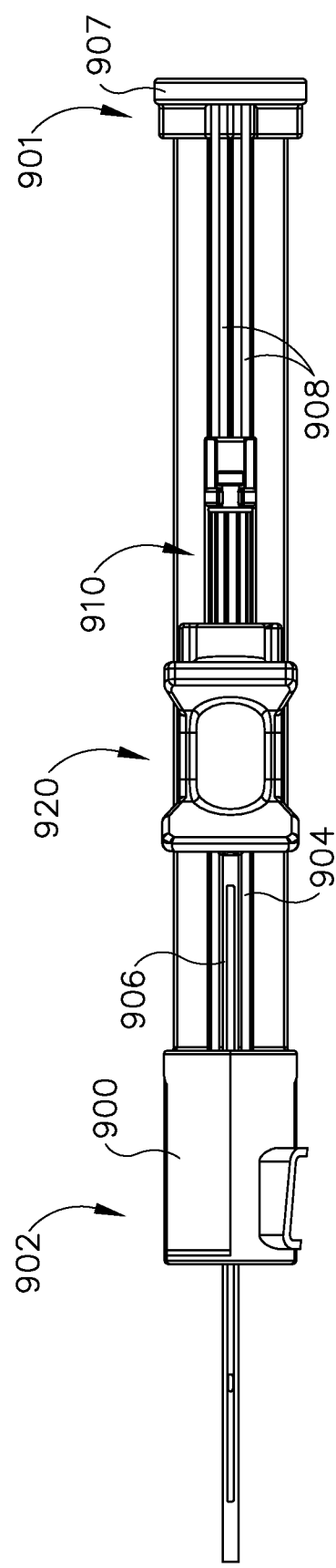
FIG. 63 depicts a top view of the instrument of FIG. 61.
Figure 64:
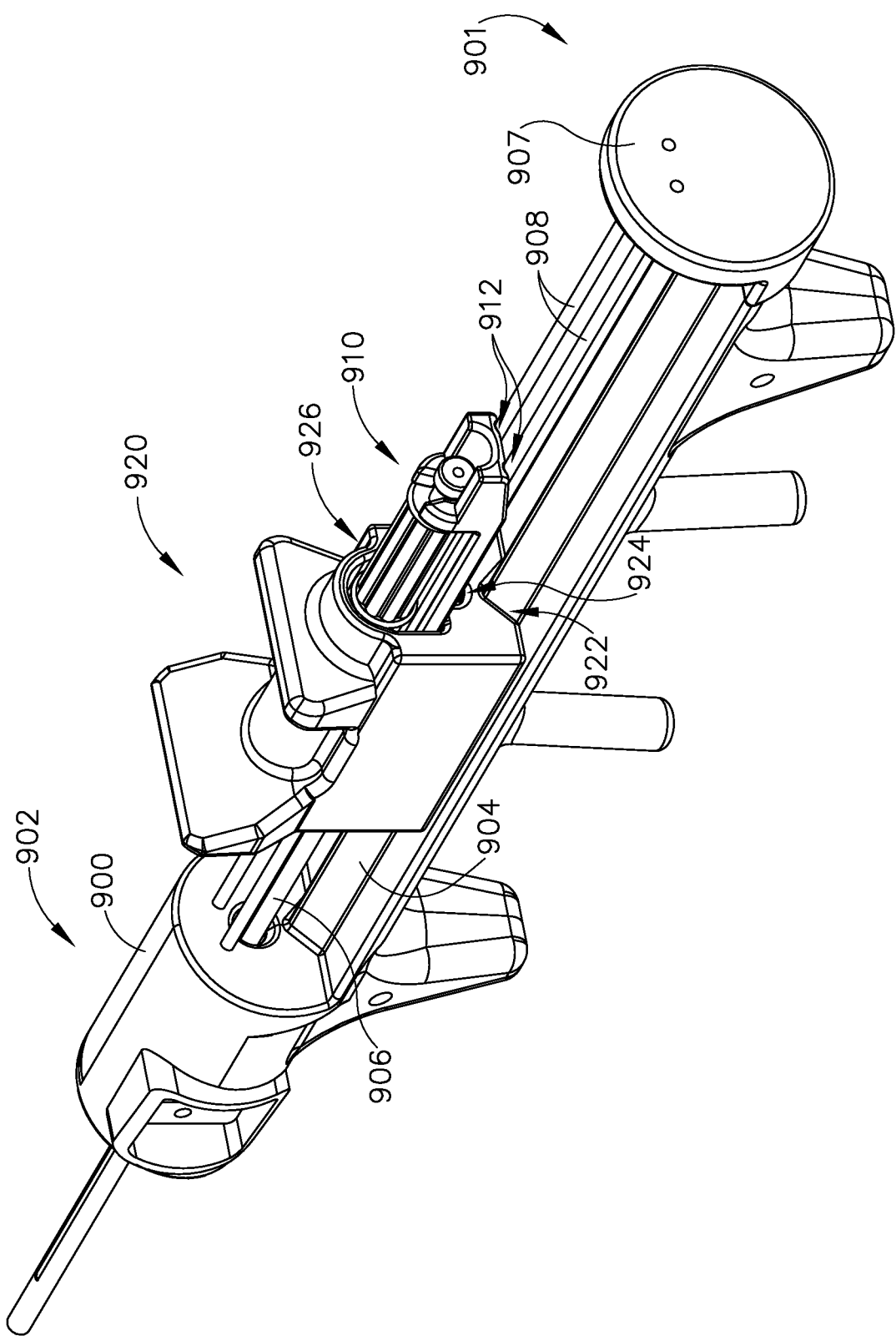
FIG. 64 depicts another perspective view of the instrument of FIG. 61.

Guidewire movement mechanism (860) is secured to guidewire (106). As with guidewire movement mechanism (112) discussed above, guidewire movement mechanism (860) is operatively disposed on handle (850) and is operable to longitudinally advance and retract guidewire (106) by longitudinally sliding guidewire movement mechanism (860) along the length of magnet (854) and shaft (856). As best seen in FIGS. 57 and 60, guidewire movement mechanism (860) comprises a rectangular ferrous element (862) disposed within guidewire movement mechanism (860). By way of example only, ferrous element (862) may comprise a piece of ferrous metal, a magnet, and/or some other kind of ferrous component. Ferrous element (862) of guidewire movement mechanism (860) is configured to associate with magnet (854) of handle (850) such that guidewire movement mechanism (860) is attracted toward a middle of top surface (855) so as to prevent transverse movement of guidewire movement mechanism (860) while at the same time permitting longitudinal movement of guidewire movement mechanism (860). Thus, it should be appreciated that ferrous element (862) of guidewire movement mechanism (860) is configured to associate with magnet (854) of handle (850) such that guidewire movement mechanism (860) may be slid along the length of magnet (854); and so as to prevent transverse movement of guidewire movement mechanism (860). Furthermore, guidewire movement mechanism (860) slidably receives shaft (856) within a circular opening (864) such that guidewire movement mechanism (860) may be slid along the length of shaft (806). Thus, magnet (854) and shaft (856) provide guidance and support for guidewire movement mechanism (860).

Dilation catheter movement actuator (870) is secured to dilation catheter (108). As with dilation catheter movement actuator (114) discussed above, dilation catheter movement actuator (870) is operatively disposed on handle (850) and is operable to longitudinally advance and retract dilation catheter (108) by longitudinally sliding dilation catheter movement actuator (820) along the length of magnet (854) and shaft (856). As best seen in FIG. 60, dilation catheter movement actuator (870) comprises a rectangular ferrous element (872) disposed within dilation catheter movement actuator (870). By way of example only, ferrous element (872) may comprise a piece of ferrous metal, a magnet, and/or some other kind of ferrous component. Ferrous element (872) of dilation catheter movement actuator (870) is configured to associate with magnet (854) of handle (850) such dilation catheter movement actuator (870) is attracted toward the middle of top surface (855) so as to prevent transverse movement of dilation catheter movement actuator (870) while at the same time permitting longitudinal movement of dilation catheter movement actuator (870). Thus, it should be appreciated that ferrous element (872) of dilation catheter movement actuator (870) is configured to associate with magnet (854) of handle (850) such that dilation catheter movement actuator (870) may be slid along the length of magnet (854); and so as to prevent transverse movement of dilation catheter movement actuator (870). Furthermore, dilation catheter movement actuator (870) slidably receives shaft (856) within a circular opening (874) such that dilation catheter movement actuator (870) may be slid along the length of shaft (856). Thus, magnet (854) and shaft (856) provide guidance and support for dilation catheter movement actuator (870).

FIGS. 61-66 show another exemplary handle (900), a guidewire movement mechanism (910), and a dilation catheter movement actuator (920). Guidewire movement mechanism (910) is configured to operate substantially similar to guidewire movement mechanism (112) discussed above except for the differences discussed below. In particular, guidewire movement mechanism (910) is operable to longitudinally advance and retract guidewire (106) relative to handle (900) and through the second lumen of dilation catheter (108) by longitudinally sliding guidewire movement mechanism (910) along the length of handle (900). Dilation catheter movement actuator (920) is configured to operate substantially similar to dilation catheter movement actuator (114) discussed above except for the differences discussed below. In particular, dilation catheter movement actuator (920) is operable to longitudinally advance and retract dilation catheter (108) relative to handle (900) through the lumen of guide catheter (104) by longitudinally sliding dilation catheter movement actuator (920) along handle (900).

Figure 65:
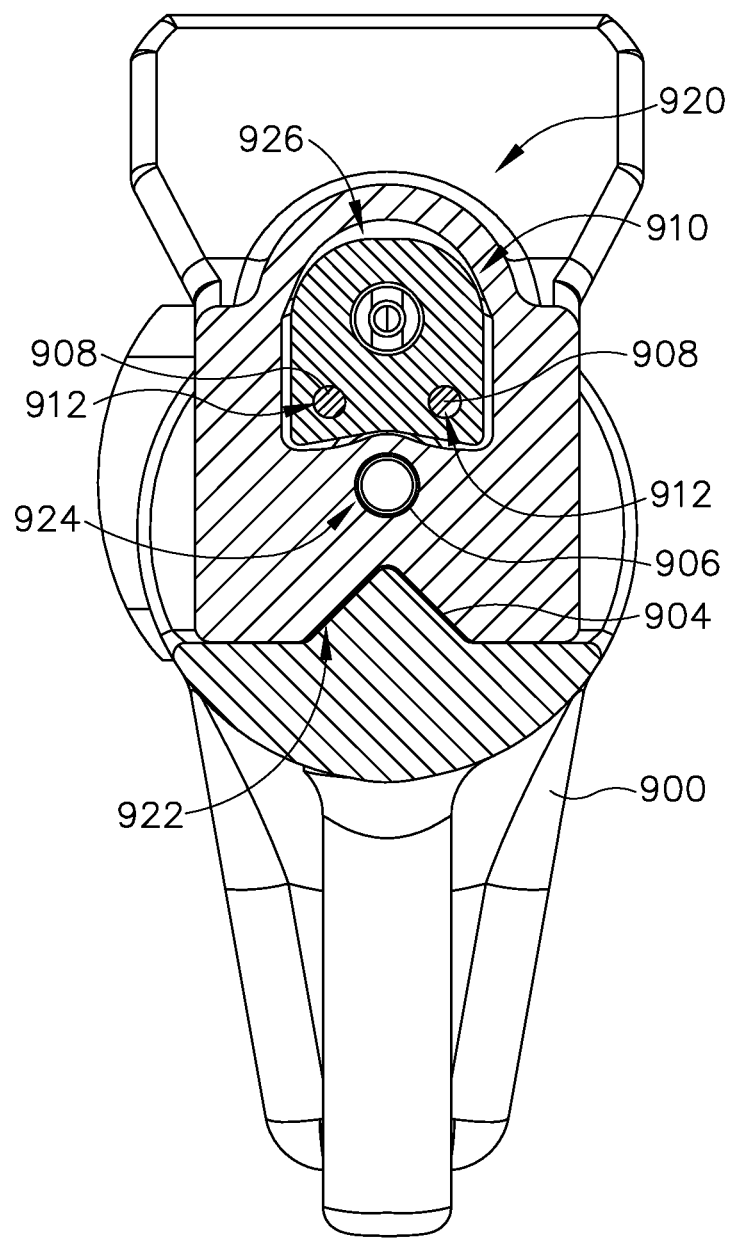
FIG. 65 depicts a cross-sectional rear view of the instrument of FIG. 61, taken along line 65-65 of FIG. 62.
Figure 66:
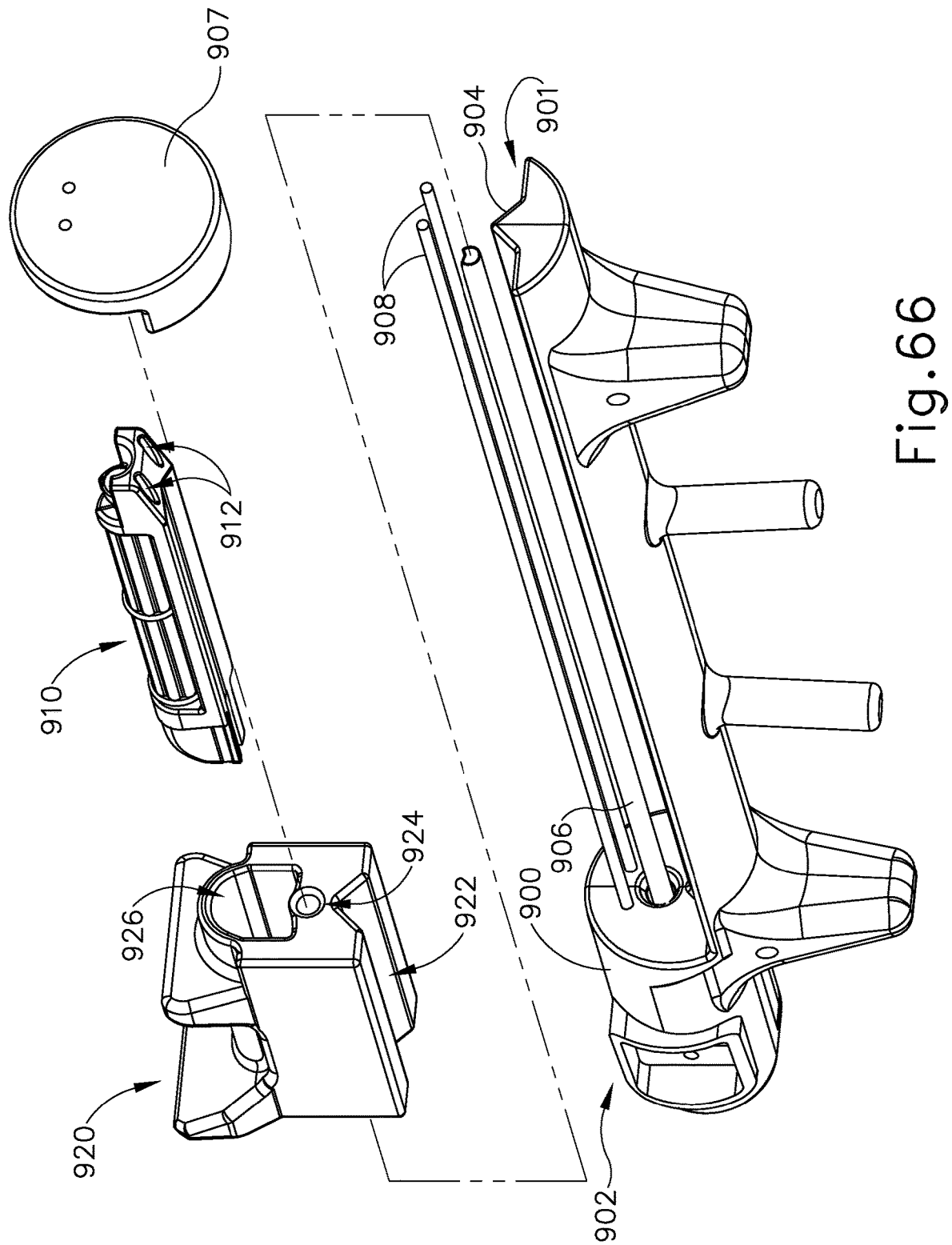
FIG. 66 depicts a partially exploded perspective view of the instrument of FIG. 61.

Handle (900) includes a proximal end (901), a distal end (902), and an elongate track (904) extending from a top surface of handle (900). As best seen in FIGS. 65 and 66, track (904) has a triangular cross-sectional profile. Handle (900) further comprises a rigid shaft (906) extending proximally from a distal portion of handle (900); and a pair of rods (908) extending between the distal portion of handle (900) and a proximal end cap (907). As will be discussed in more detail below, guidewire movement mechanism (910) and dilation catheter movement actuator (920) are configured to slidably couple with track (904), shaft (906), and rods (908) such that guidewire movement mechanism (910) and dilation catheter movement actuator (920) may slide along the length of track (904), shaft (906), and rods (908). Track (904), shaft (906), and rods (908) provide guidance and support to guidewire movement mechanism (910) and dilation catheter movement actuator (920) during such sliding. Shaft (906) may be configured to slidably receive a dilation catheter (108), with dilation catheter (108) being slidably received in guide catheter (104), and with guidewire (106) being slidably received in dilation catheter (108). It should therefore be understood that guide catheter (104), dilation catheter (108), shaft (906), and at least a portion of guidewire (106) may all be coaxially aligned on the same longitudinal axis. In some versions, shaft (906) is substantially identical to guidewire support (118) described above. By way of example only, shaft (906) may comprise a hypotube with a slit formed therein to transversely receive guidewire (106).

Guidewire movement mechanism (910) is secured to guidewire (106). As with guidewire movement mechanism (112) discussed above, guidewire movement mechanism (910) is operatively disposed on handle (900) and is operable to longitudinally advance and retract guidewire (106) by longitudinally sliding guidewire movement mechanism (900) along the length of rods (908). As best seen in FIGS. 65 and 66, guidewire movement mechanism (910) comprises a pair of circular openings (912) formed in a bottom surface of guidewire movement mechanism (910). Openings (912) are configured to slidably receive rods (908) of handle (900) such that guidewire movement mechanism (910) may be slid along the length of rods (908). Also, as will be discussed in more detail below, guidewire movement mechanism (910) is configured to be slid through dilation catheter movement actuator (920), independent of dilation catheter movement actuator (920).

Dilation catheter movement actuator (920) is secured to dilation catheter (108). As with dilation catheter movement actuator (114) discussed above, dilation catheter movement actuator (920) is operatively disposed on handle (900) and is operable to longitudinally advance and retract dilation catheter (108) by longitudinally sliding dilation catheter movement actuator (920) along the length of track (904) and shaft (906). Dilation catheter movement actuator (920) defines an elongate recess (922) formed in a bottom surface of dilation catheter movement actuator (920). As best seen in FIGS. 65 and 66, recess (922) has a triangular cross-sectional profile complementing that of track (904). Recess (922) is configured to slidably receive track (904) of handle (900) such that dilation catheter movement actuator (920) may be slid along the length of track (904). Furthermore, dilation catheter movement actuator (920) slidably receives shaft (906) within a circular opening (924) such that dilation catheter movement actuator (920) may be slid along the length of shaft (906).

Dilation catheter movement actuator (920) further defines an opening (926) that is configured to slidably receive guidewire movement mechanism (910), such that guidewire movement mechanism (910) may be slid through dilation catheter movement actuator (920) independent of dilation catheter movement actuator (920). In particular, rods (908) pass through opening (926) of dilation catheter movement actuator (920) such that guidewire movement mechanism (910) may be slid through dilation catheter movement actuator (920) along rods (908). Opening (926) is sized large enough to provide a gap between guidewire movement mechanism (910) and dilation catheter movement actuator (920) as guidewire movement mechanism (910) passes through dilation catheter movement actuator (920). Guidewire movement mechanism (910) is long enough such that a distal end of guidewire movement mechanism (910) protrudes distally of dilation catheter movement actuator (920) when a proximal end of guidewire movement mechanism (910) is positioned in dilation catheter movement actuator (920); and such that a proximal end of guidewire movement mechanism (910) protrudes proximally of dilation catheter movement actuator (920) when a distal end of guidewire movement mechanism (910) is positioned in dilation catheter movement actuator (920).

FIGS. 67-72 show another exemplary handle (950), a guidewire movement mechanism (960), and a dilation catheter movement actuator (970). Guidewire movement mechanism (960) is configured to operate substantially similar to guidewire movement mechanism (112) discussed above except for the differences discussed below. In particular, guidewire movement mechanism (960) is operable to longitudinally advance and retract guidewire (106) relative to handle (950), through guidewire support (118), and through the second lumen of dilation catheter (108) by longitudinally sliding guidewire movement mechanism (960) along the length of handle (950). Dilation catheter movement actuator (970) is configured to operate substantially similar to dilation catheter movement actuator (114) discussed above except for the differences discussed below. In particular, dilation catheter movement actuator (970) is operable to longitudinally advance and retract dilation catheter (108) relative to handle (950) through the lumen of guide catheter (104) by longitudinally sliding dilation catheter movement actuator (970) along handle (950).

Figure 71:
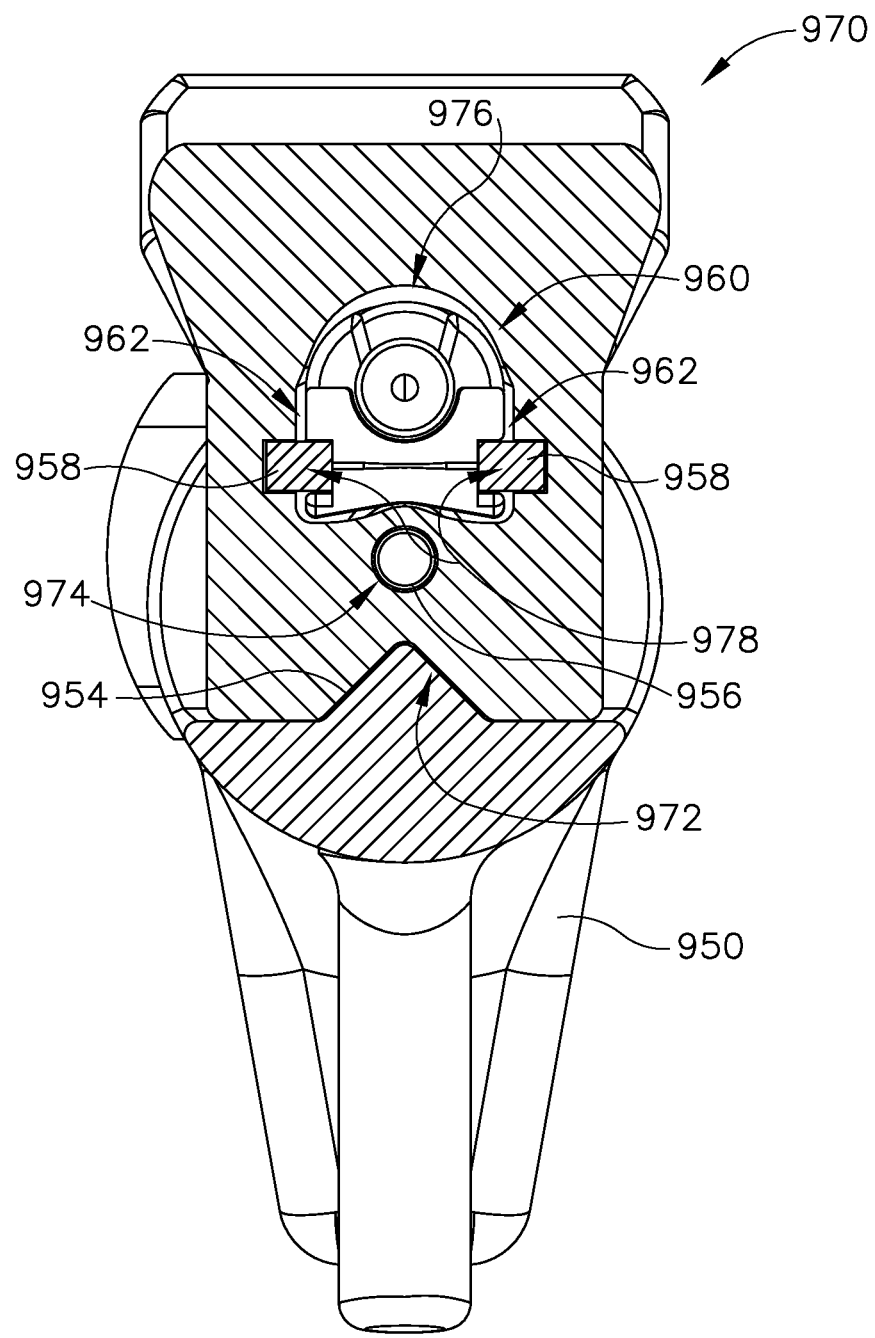
FIG. 71 depicts a cross-sectional rear view of the instrument of FIG. 67, taken along line 71-17 of FIG. 68.
Figure 72:
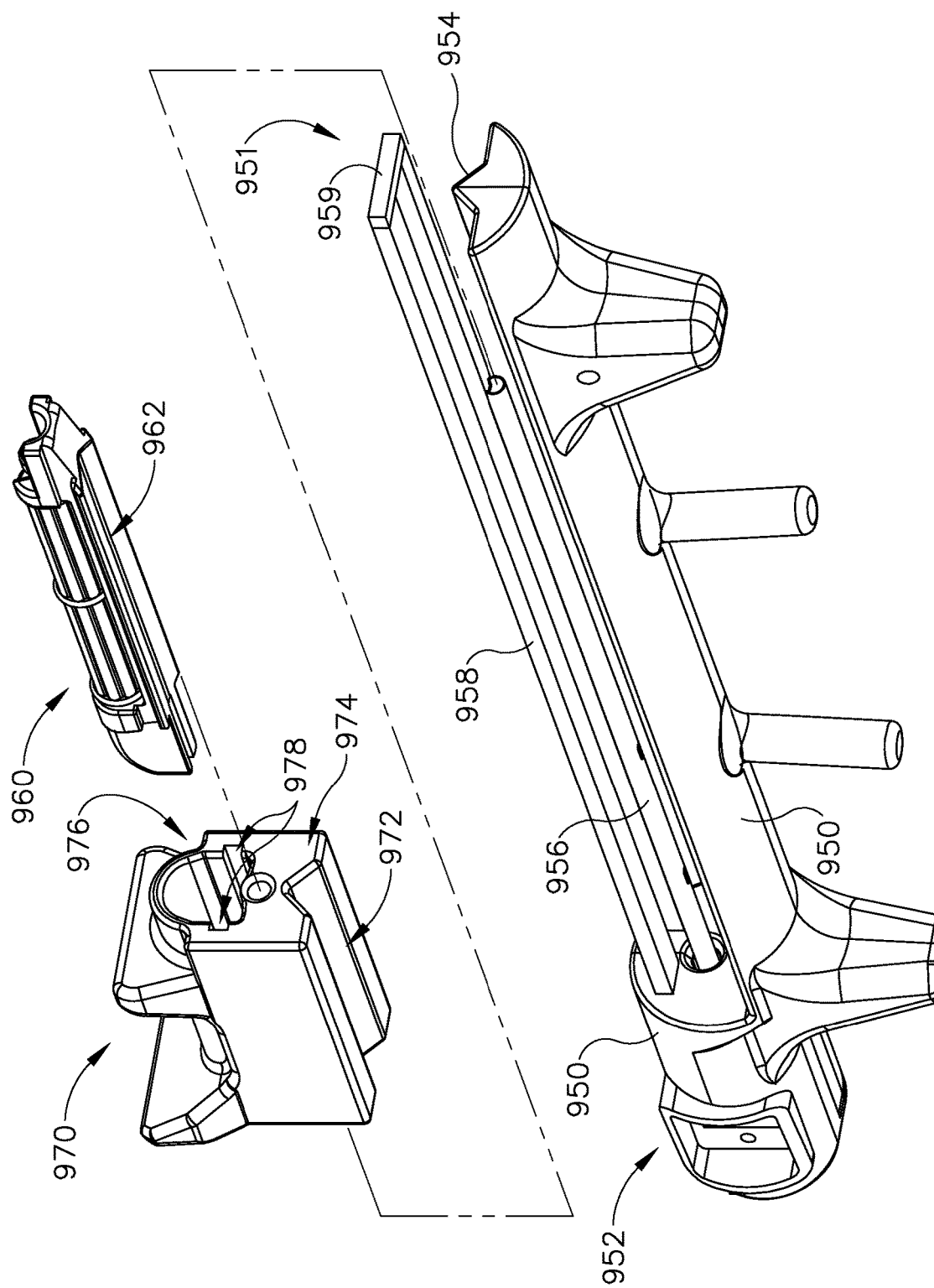
FIG. 72 depicts a partially exploded perspective view of the instrument of FIG. 67.
Figure 73:
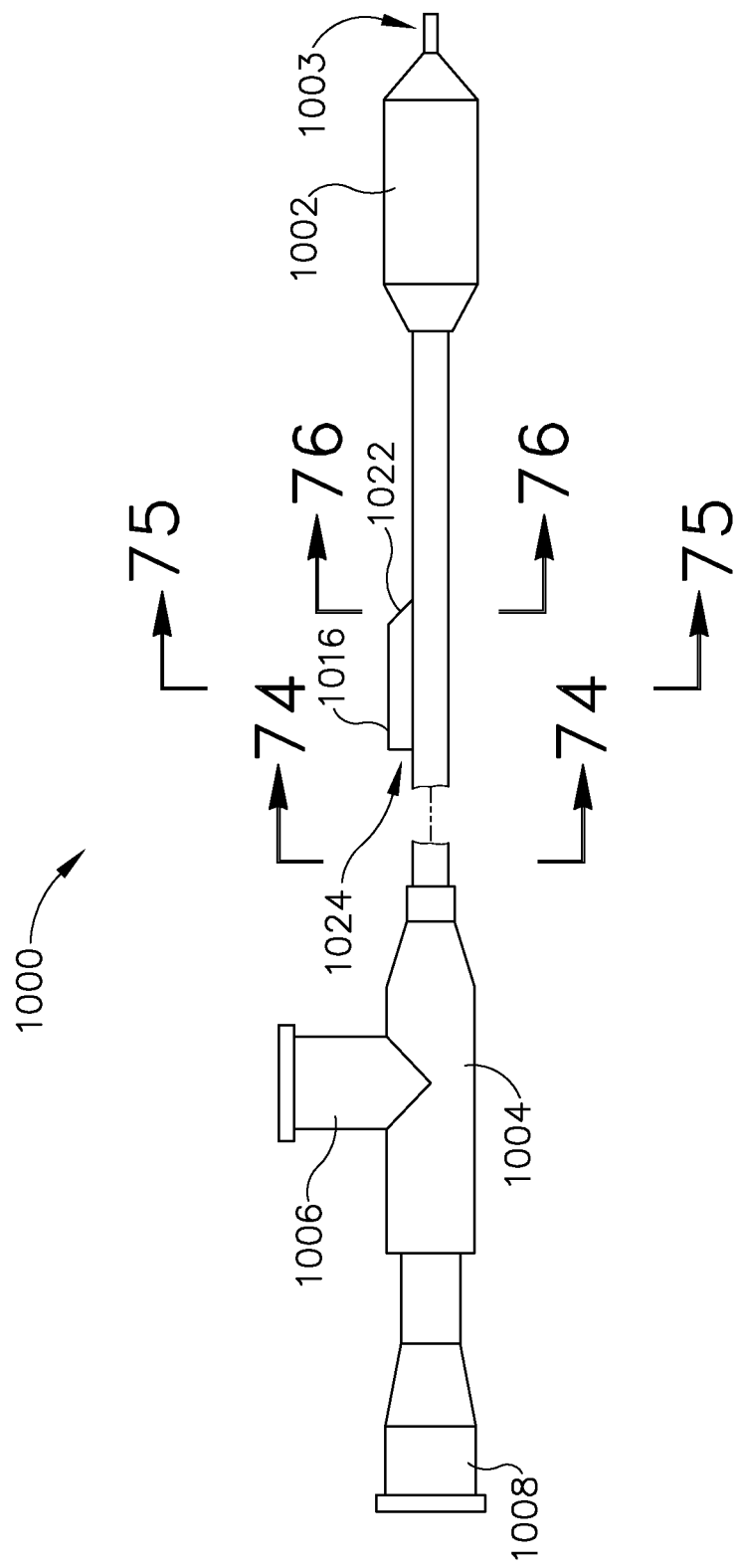
FIG. 73 depicts a side elevational view of another exemplary dilation catheter.

Handle (950) includes a proximal end (951), a distal end (952), and an elongate track (954) extending from a top surface of handle (950). As best seen in FIGS. 71 and 72, track (954) has a triangular cross-sectional profile. Handle (950) further comprises a rigid shaft (956) extending proximally from a distal portion of handle (950); and a rigid track (958) extending proximally from the distal portion of handle (950). As will be discussed in more detail below, guidewire movement mechanism (960) and dilation catheter movement actuator (970) are configured to slidably couple with track (954), shaft (956), and track (958) such that guidewire movement mechanism (960) and dilation catheter movement actuator (970) may slide along the length of track (954), shaft (956), and track (958). Track (954), shaft (956), and track (958) provide guidance and support to guidewire movement mechanism (960) and dilation catheter movement actuator (970) during such sliding. Shaft (956) may be configured to slidably receive a dilation catheter (108), with dilation catheter (108) being slidably received in guide catheter (104), and with guidewire (106) being slidably received in dilation catheter (108). It should therefore be understood that guide catheter (104), dilation catheter (108), shaft (956), and at least a portion of guidewire (106) may all be coaxially aligned on the same longitudinal axis. In some versions, shaft (956) is substantially identical to guidewire support (118) described above. By way of example only, shaft (956) may comprise a hypotube with a slit formed therein to transversely receive guidewire (106).

Figure 67:
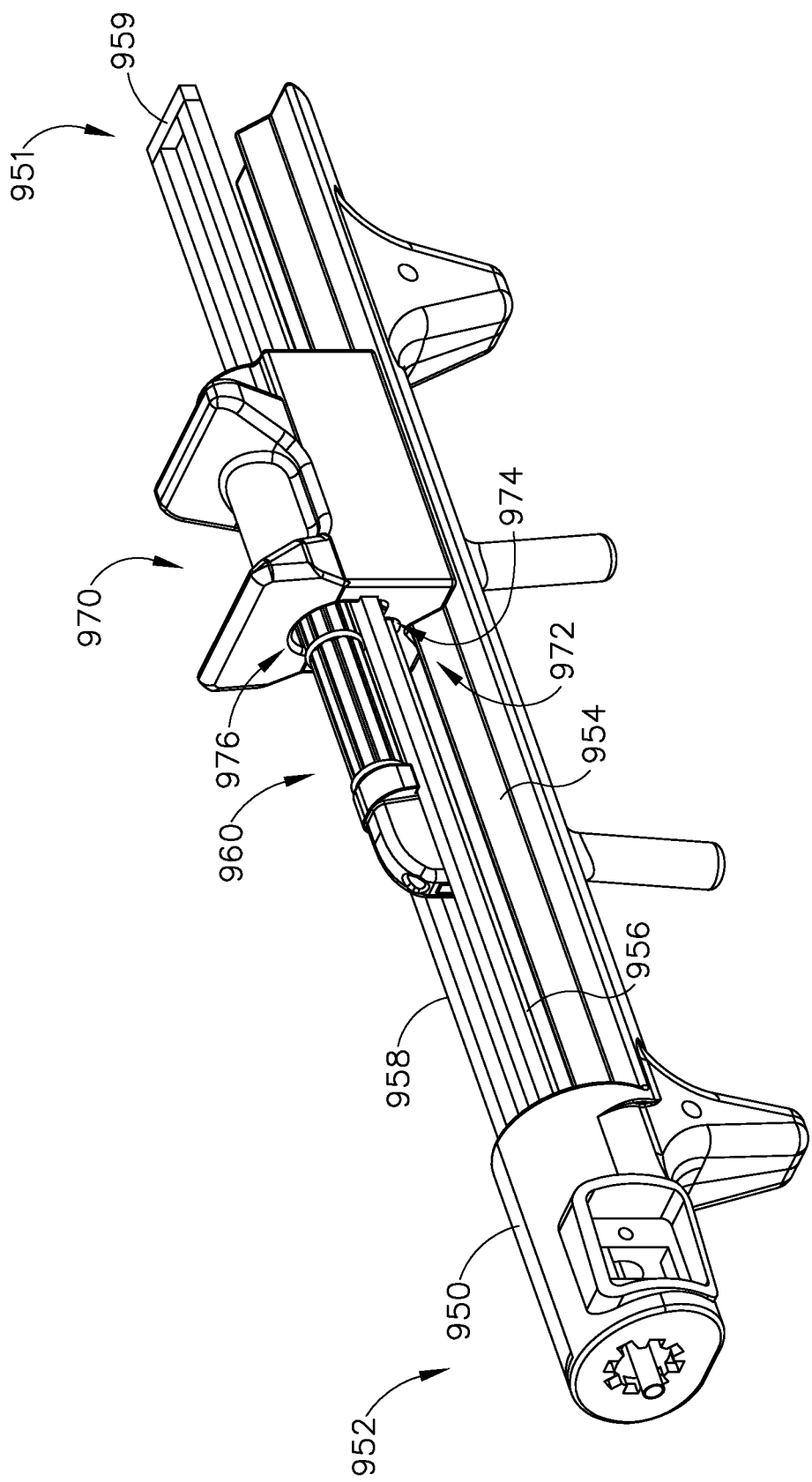
FIG. 67 depicts a perspective view of another exemplary instrument suitable for incorporation into the dilation catheter system of FIG. 1.
Figure 68:
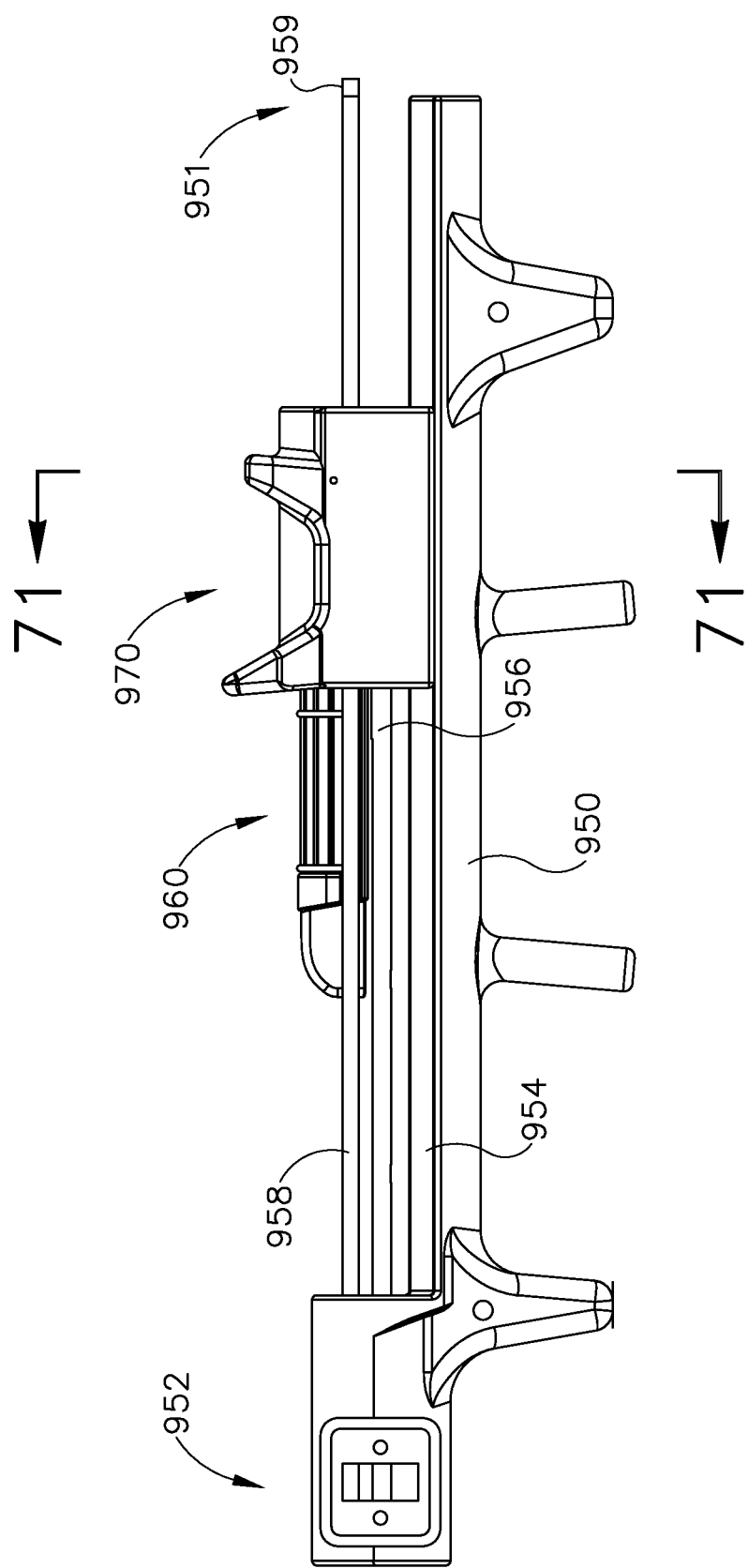
FIG. 68 depicts a side elevational view of the instrument of FIG. 67.
Figure 69:
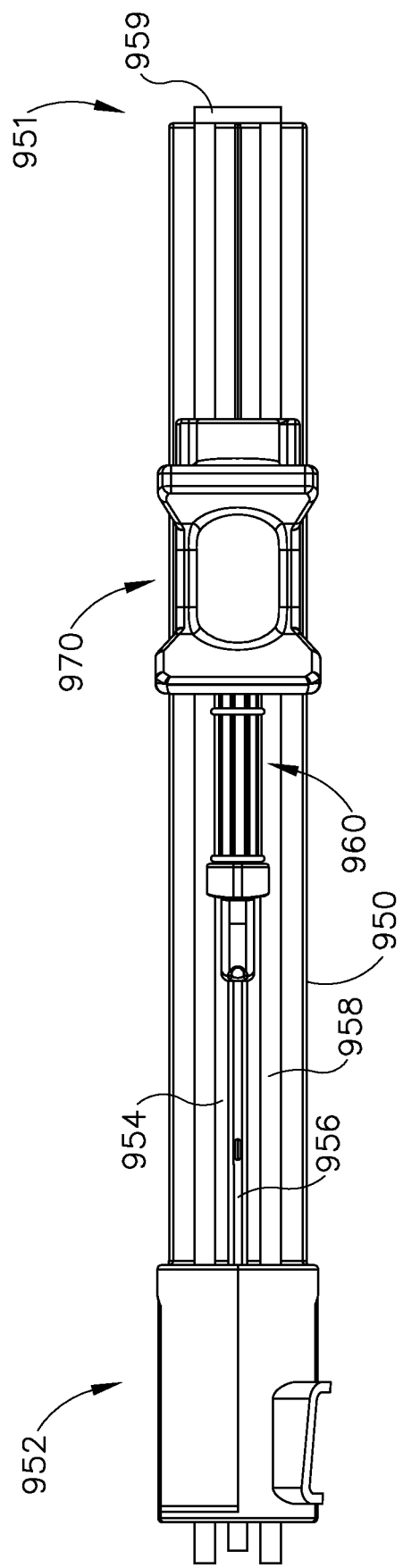
FIG. 69 depicts a top view of the instrument of FIG. 67.
Figure 70:
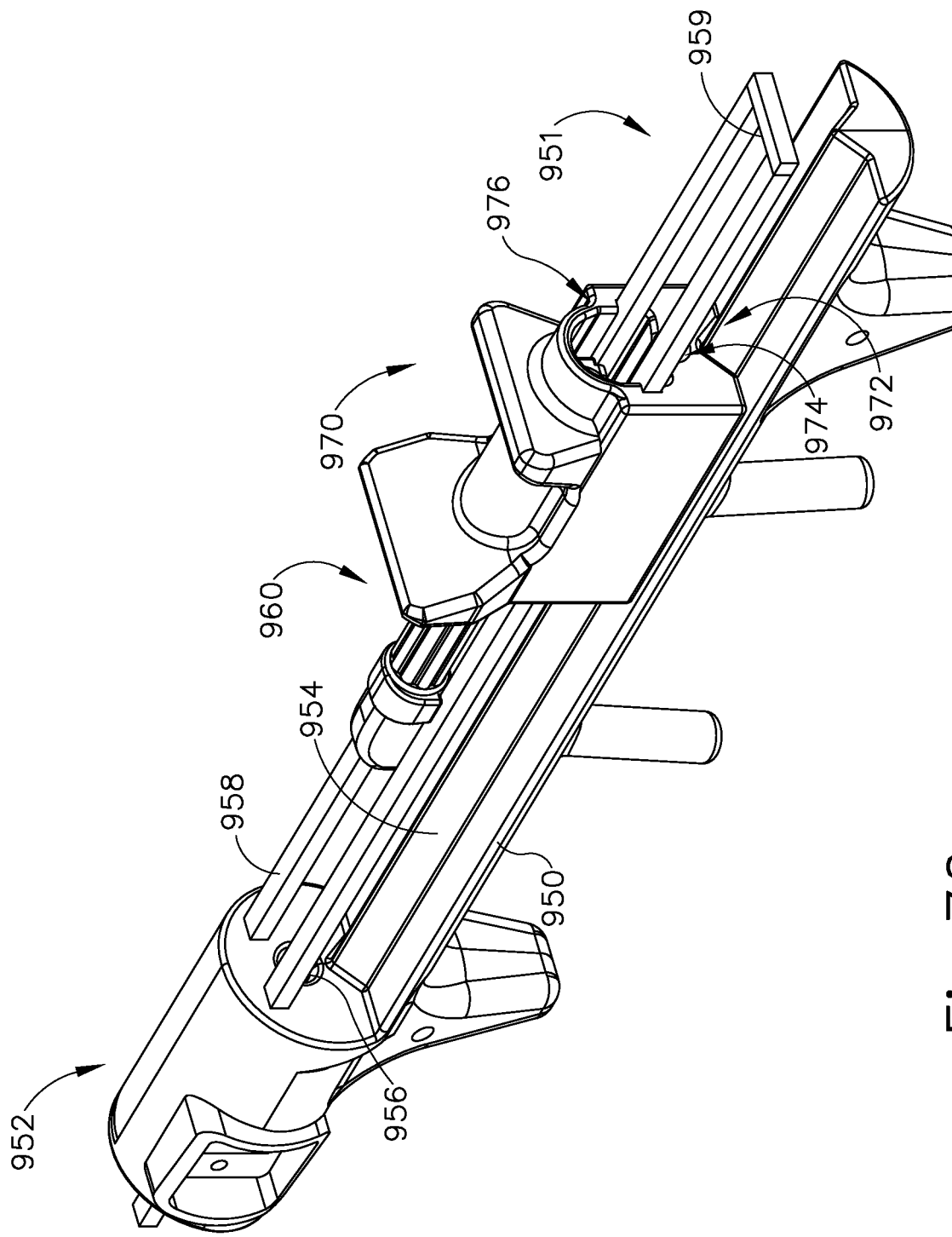
FIG. 70 depicts another perspective view of the instrument of FIG. 67.

Guidewire movement mechanism (960) is secured to guidewire (106). As with guidewire movement mechanism (112) discussed above, guidewire movement mechanism (960) is operatively disposed on handle (950) and is operable to longitudinally advance and retract guidewire (106) by longitudinally sliding guidewire movement mechanism (960) along the length of track (958). As best seen in FIGS. 71 and 72, guidewire movement mechanism (960) comprises a pair of rectangular channels (962) formed in opposing side surfaces of guidewire movement mechanism (960). Channels (962) are configured to slidably receive track (958) of handle (950) such that guidewire movement mechanism (960) may be slid along the length of track (958). As best seen in FIGS. 67, 69, and 70, track (958) includes a proximal crossbar (959) that is configured to prevent sliding of guidewire movement mechanism (960) beyond track (958). Crossbar (959) may also provide enhanced rigidity and integrity to track (958). As will be discussed in more detail below, guidewire movement mechanism (960) is configured to be slid through dilation catheter movement actuator (970) independent of dilation catheter movement actuator (970).

Dilation catheter movement actuator (970) is secured to dilation catheter (108). As with dilation catheter movement actuator (114) discussed above, dilation catheter movement actuator (970) is operatively disposed on handle (950) and is operable to longitudinally advance and retract dilation catheter (108) by longitudinally sliding dilation catheter movement actuator (970) along the length of track (954), shaft (956), and track (958). Dilation catheter movement actuator (970) defines an elongate recess (972) formed in a bottom surface of dilation catheter movement actuator (970). As best seen in FIGS. 71 and 72, recess (972) has a triangular cross-sectional profile complementing that of track (954). Recess (972) is configured to slidably receive track (954) of handle (950) such that dilation catheter movement actuator (970) may be slid along the length of track (954). Furthermore, dilation catheter movement actuator (970) slidably receives shaft (956) within a circular opening (974) such that dilation catheter movement actuator (970) may be slid along the length of shaft (956). Dilation catheter movement actuator (970) also defines a pair of rectangular channels (978) formed in opposing side surfaces of opening (976). Channels (978) are configured to slidably receive track (958) of handle (950) such that dilation catheter movement actuator (970) may be slid along the length of track (958) along handle (950).

Dilation catheter movement actuator (970) further comprises an opening (976) configured to slidably receive guidewire movement mechanism (960), such that guidewire movement mechanism (960) may be slid through dilation catheter movement actuator (970) independent of dilation catheter movement actuator (970). In particular, track (958) passes through opening (976) of dilation catheter movement actuator (970) such that guidewire movement mechanism (960) may be slid through dilation catheter movement actuator (970) along track (958). Opening (976) is sized large enough to provide a gap between guidewire movement mechanism (960) and dilation catheter movement actuator (970) as guidewire movement mechanism (960) passes through dilation catheter movement actuator (970). Guidewire movement mechanism (960) is long enough such that a distal end of guidewire movement mechanism (960) protrudes distally of dilation catheter movement actuator (970) when a proximal end of guidewire movement mechanism (960) is positioned in dilation catheter movement actuator (970); and such that a proximal end of guidewire movement mechanism (960) protrudes proximally of dilation catheter movement actuator (970) when a distal end of guidewire movement mechanism (960) is positioned in dilation catheter movement actuator (970).

VI. Exemplary Dilation Catheter with Side Port

In some versions of dilation catheter (20, 108), it may be desirable to provide a feature that provides for side entry of guidewire (50, 106) into the second lumen of dilation catheter (20, 108). FIGS. 73-83 show merely illustrative examples of dilation catheters (1000, 1050) with side entry ports. Each dilation catheter (1000, 1050) may be readily used as a substitute for dilation catheters (20, 108) as described above. Dilation catheters (1000, 1050) are configured to operate substantially similar to dilation catheters (20, 108) discussed above except for the differences discussed below.

Figure 74:
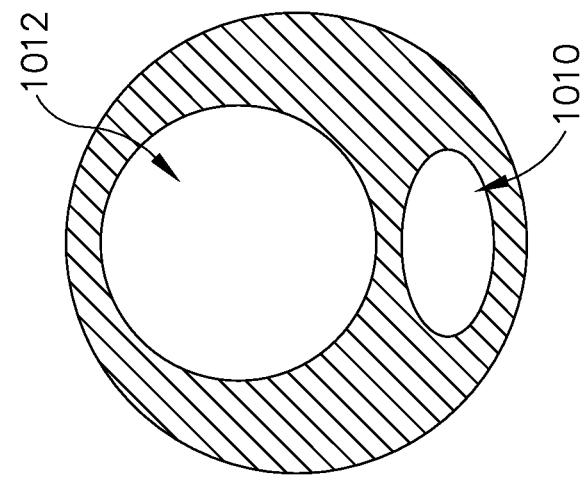
FIG. 74 depicts a cross-sectional rear view of the dilation catheter of FIG. 73, taken along line 74-74 of FIG. 73.
Figure 75:
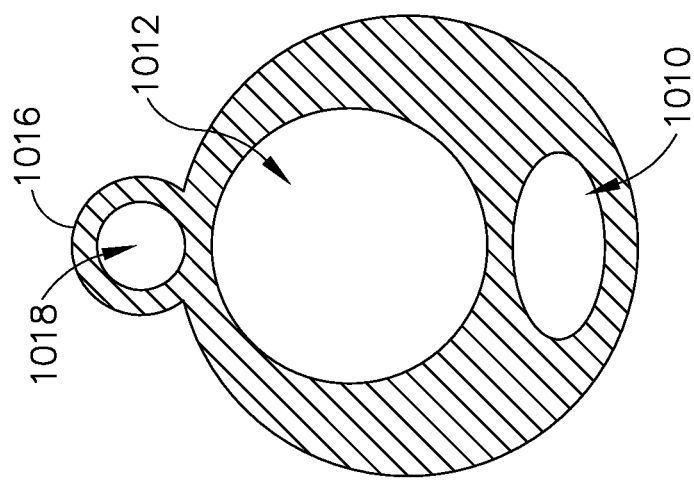
FIG. 75 depicts another cross-sectional rear view of the dilation catheter of FIG. 73, taken along line 75-75 of FIG. 73.
Figure 76:
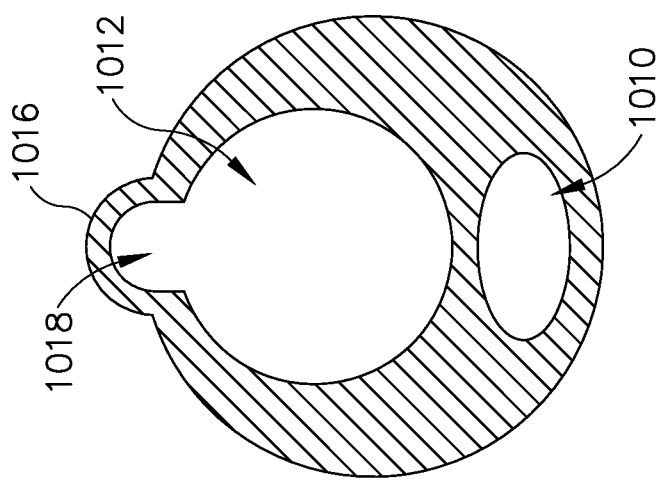
FIG. 76 depicts another cross-sectional rear view of the dilation catheter of FIG. 73, taken along line 76-76 of FIG. 73.

FIGS. 73-78 show dilation catheter (1000), which includes an inflatable balloon (1002). The proximal end of dilation catheter (1000) includes a grip (1004), which has a lateral port (1006) and an open proximal end (1008). Dilation catheter (1000) defines a first lumen (1010) that provides fluid communication between lateral port (1006) and the interior of balloon (1002). Port (1006) and lumen (1010) may thus be used to selectively inflate and deflate balloon (1002). Dilator catheter (1000) further defines a second lumen (1012) that extends from open proximal end (1028) to an open distal end (1003) that is distal to balloon (1002). This second lumen (1012) is configured to slidably receive guidewire (50, 106). In some instances, irrigation fluid may be communicated through lumen (1012). As best seen in FIGS. 74-76, first and second lumens (1010, 1012) of dilator catheter (1000) are fluidly isolated from each other. Thus, balloon (1002) may be selectively inflated and deflated by communicating fluid along first lumen (1010) via lateral port (1006) while guidewire (50, 106) is positioned within the second lumen.

Figure 77:
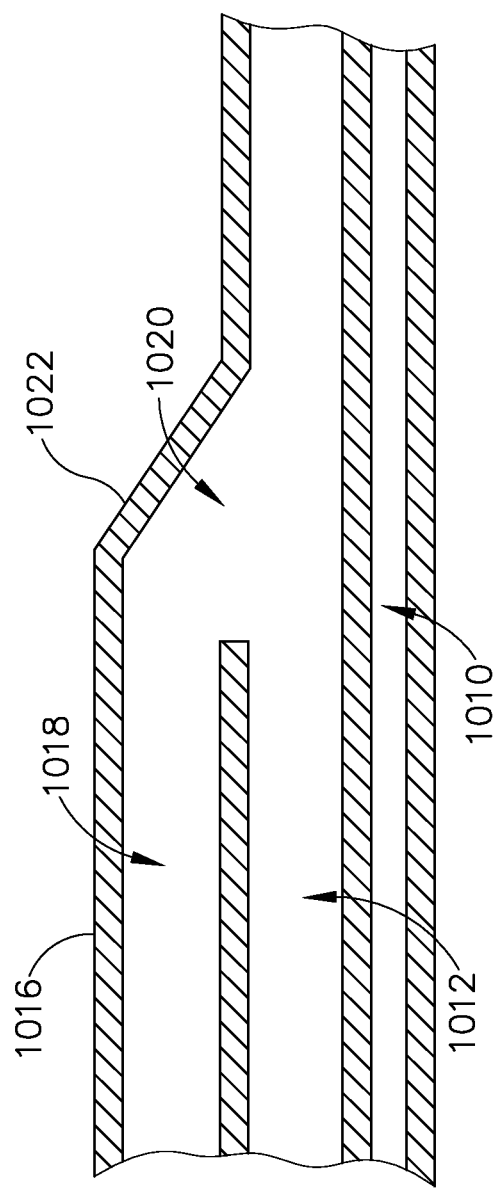
FIG. 77 depicts a cross-sectional side view of the dilation catheter of FIG. 73.

Dilation catheter (1000) further includes a side port (1016) that provides for side entry of guidewire (50) into second lumen (1012). As best seen in FIG. 77, side port (1016) defines an interior lumen (1018) that extends parallel to second lumen (1012) and then fluidly connects with second lumen (1012) along an angular path through a port (1020). Side port (1016) comprises a distal wall (1022) that is angled downwardly so as to guide guidewire (50, 106) through port (1020) into second lumen (1012) as guidewire (50, 106) is inserted distally through lumen (1018). Thus, it should be understood that guidewire (50, 106) may be fed through a proximal opening (1024) of side port (1016) and guided through port (1020) into second lumen (1012).

Figure 78:
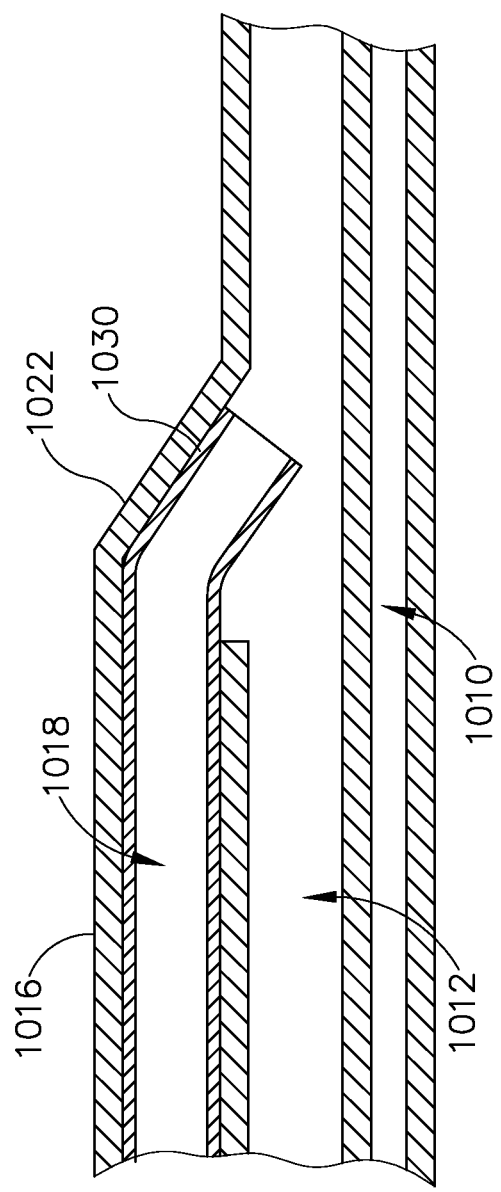
FIG. 78 depicts a cross-sectional side view of the dilation catheter of FIG. 73 having a inner liner.
Figure 79:
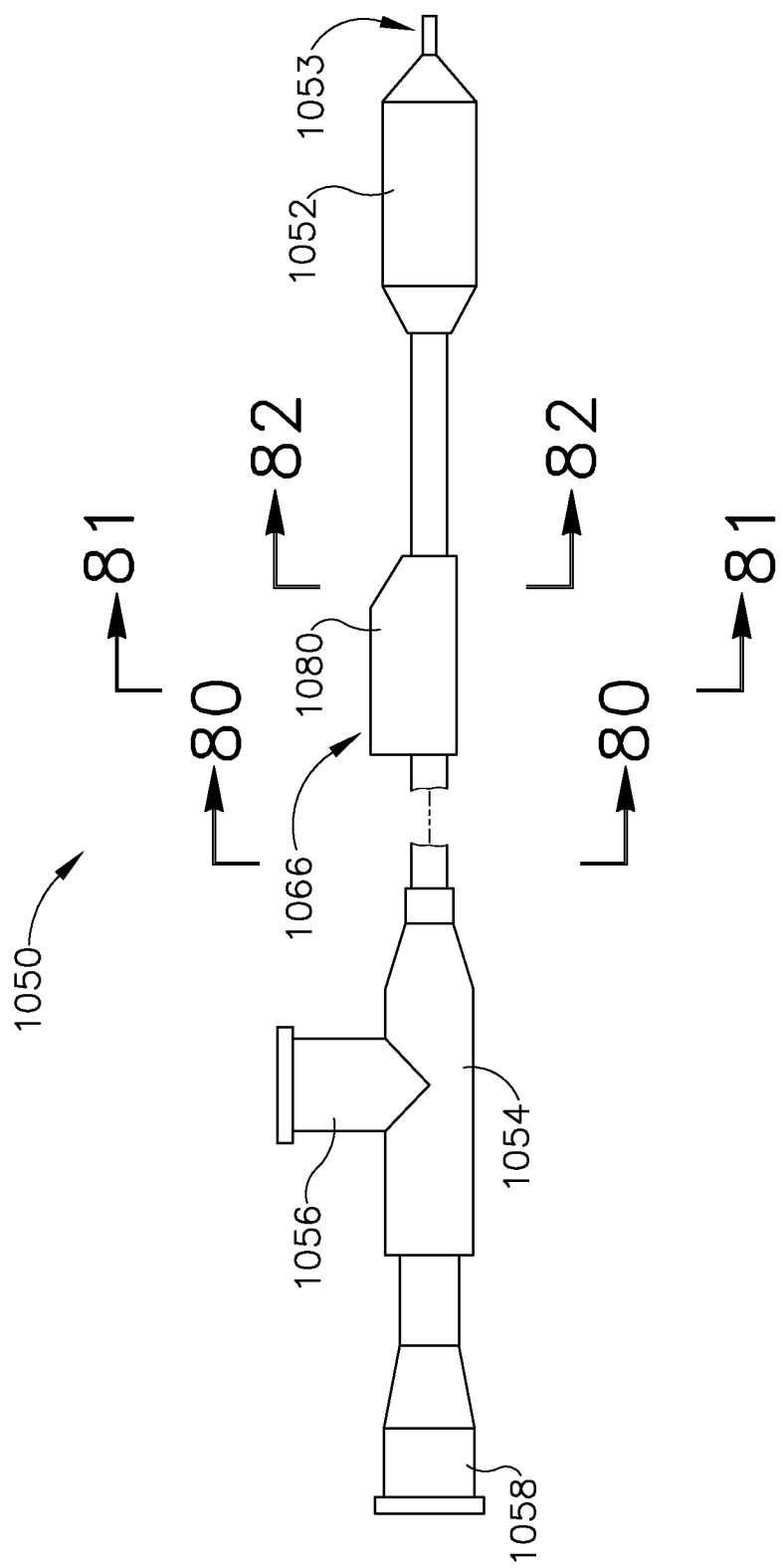
FIG. 79 depicts a side elevational view of another exemplary dilation catheter.

As shown in FIG. 78, some versions of dilation catheter (1000) may include a liner (1030) within side port (1016). Liner (1030) may comprise any appropriate material, including but not limited to PTFE. A distal portion of liner (1030) is angled downwardly so as to guide guidewire (50, 106) through port (1020) into second lumen (1012). Liner (1030) extends beyond port (1020) into second lumen (1012) to thereby reduce backflow within second lumen (1012) (e.g., when irrigation fluid is communicated through lumen (1012), etc.).

Figure 80:
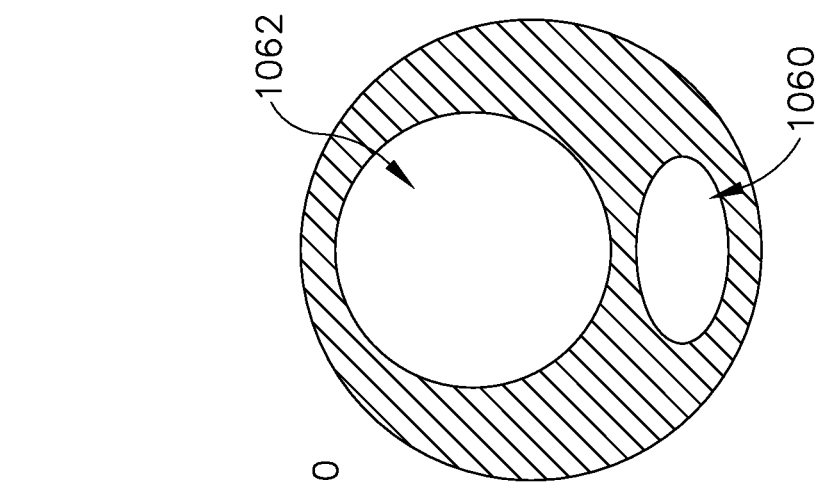
FIG. 80 depicts a cross-sectional rear view of the dilation catheter of FIG. 79, taken along line 80-80 of FIG. 79.
Figure 81:
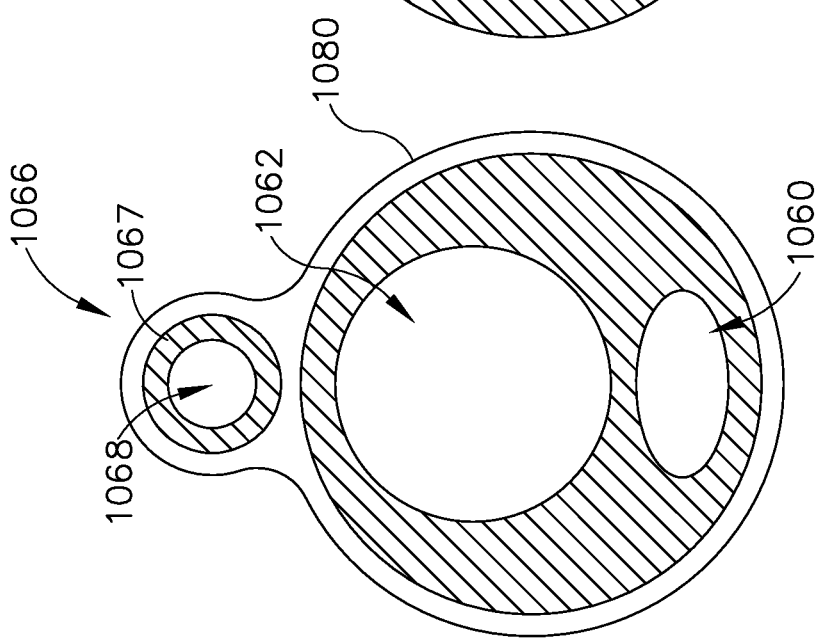
FIG. 81 depicts another cross-sectional rear view of the dilation catheter of FIG. 79, taken along line 81-81 of FIG. 79.
Figure 82:
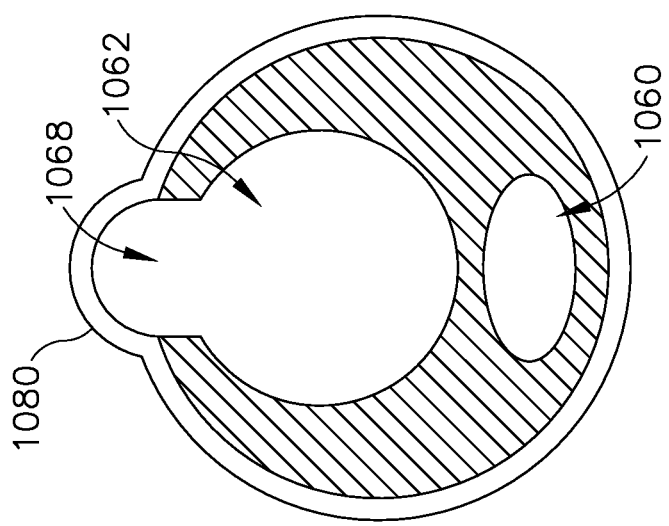
FIG. 82 depicts another cross-sectional rear view of the dilation catheter of FIG. 79, taken along line 82-82 of FIG. 79.

FIGS. 79-83 show dilation catheter (1050), which includes an inflatable balloon (1052). The proximal end of dilation catheter (1050) includes a grip (1054), which has a lateral port (1056) and an open proximal end (1058). Dilation catheter (1050) defines a first lumen (1060) that provides fluid communication between lateral port (1056) and the interior of balloon (1052). Port (1056) and lumen (1060) may thus be used to selectively inflate and deflate balloon (1052). Dilator catheter (1050) further defines a second lumen (1062) that extends from open proximal end (1078) to an open distal end (1053) that is distal to balloon (1052). This second lumen (1062) is configured to slidably receive guidewire (50, 106). In some instances, irrigation fluid may be communicated through lumen (1062). As best seen in FIGS. 80-82, first and second lumens (1060, 1062) of dilator catheter (1050) are fluidly isolated from each other. Thus, balloon (1052) may be selectively inflated and deflated by communicating fluid along first lumen (1060) via lateral port (1056) while guidewire (50, 106) is positioned within the second lumen.

Figure 83:
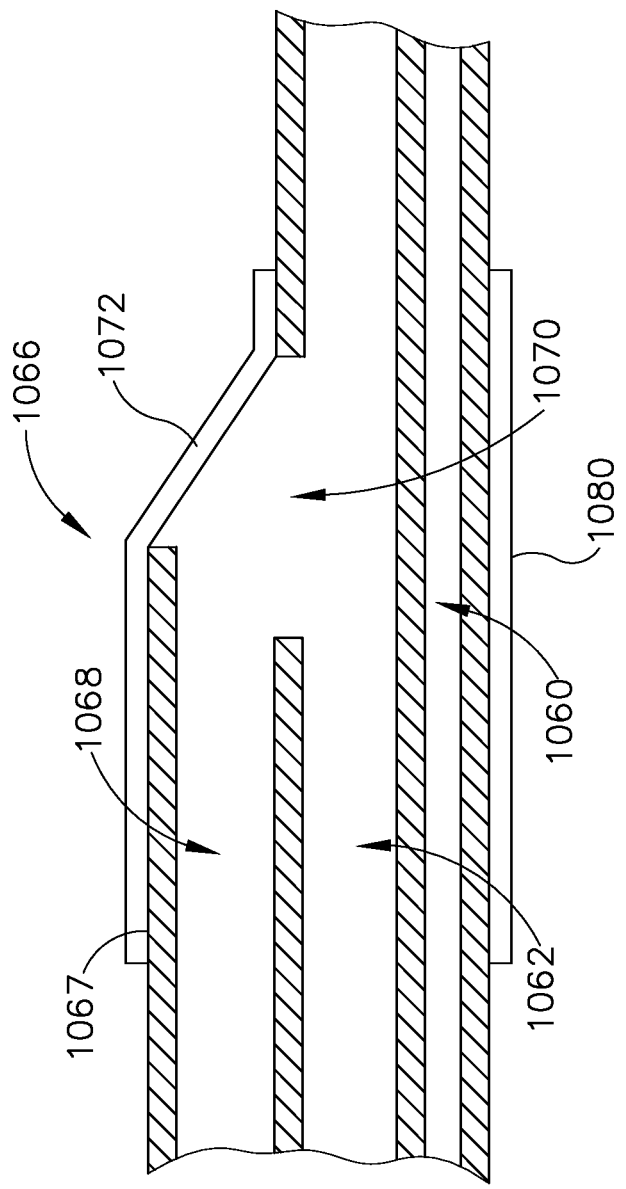
FIG. 83 depicts a cross-sectional side view of the dilation catheter of FIG. 79.

Dilation catheter (1050) further includes a side port (1066) that provides for side entry of guidewire (50) into second lumen (1062). As best seen in FIG. 83, side port (1066) comprises a tube (1067) defining an interior lumen (1068) that extends parallel to second lumen (1062). Tube (1067) and a portion of dilation catheter (1050) are encompassed by a liner (1080). Liner (1030) may comprise any appropriate material, including but not limited to PTFE and/or a conventional polyethylene terephthalate (PET) heat shrink tubing, etc. As best seen in FIG. 83, liner (1080) provides an angular path between lumen (1068) of tube (1067) and second lumen (1062) thereby fluidly connecting lumen (1068) with second lumen (1062) along an angular path through a port (1070). Liner (1080) comprises a distal wall (1072) that is angled downwardly so as to guide guidewire (50, 106) from lumen (1068) to lumen (1062) via port (1070). Thus, it should be understood that guidewire (50, 106) may be fed through a proximal opening (1074) of side port (1066) and guided from lumen (1068) to lumen (1062) via port (1070) through deflection by distal wall (1072) of liner (1080).

VII. Exemplary Dilation Catheter with Varying Diameter

Figure 84:
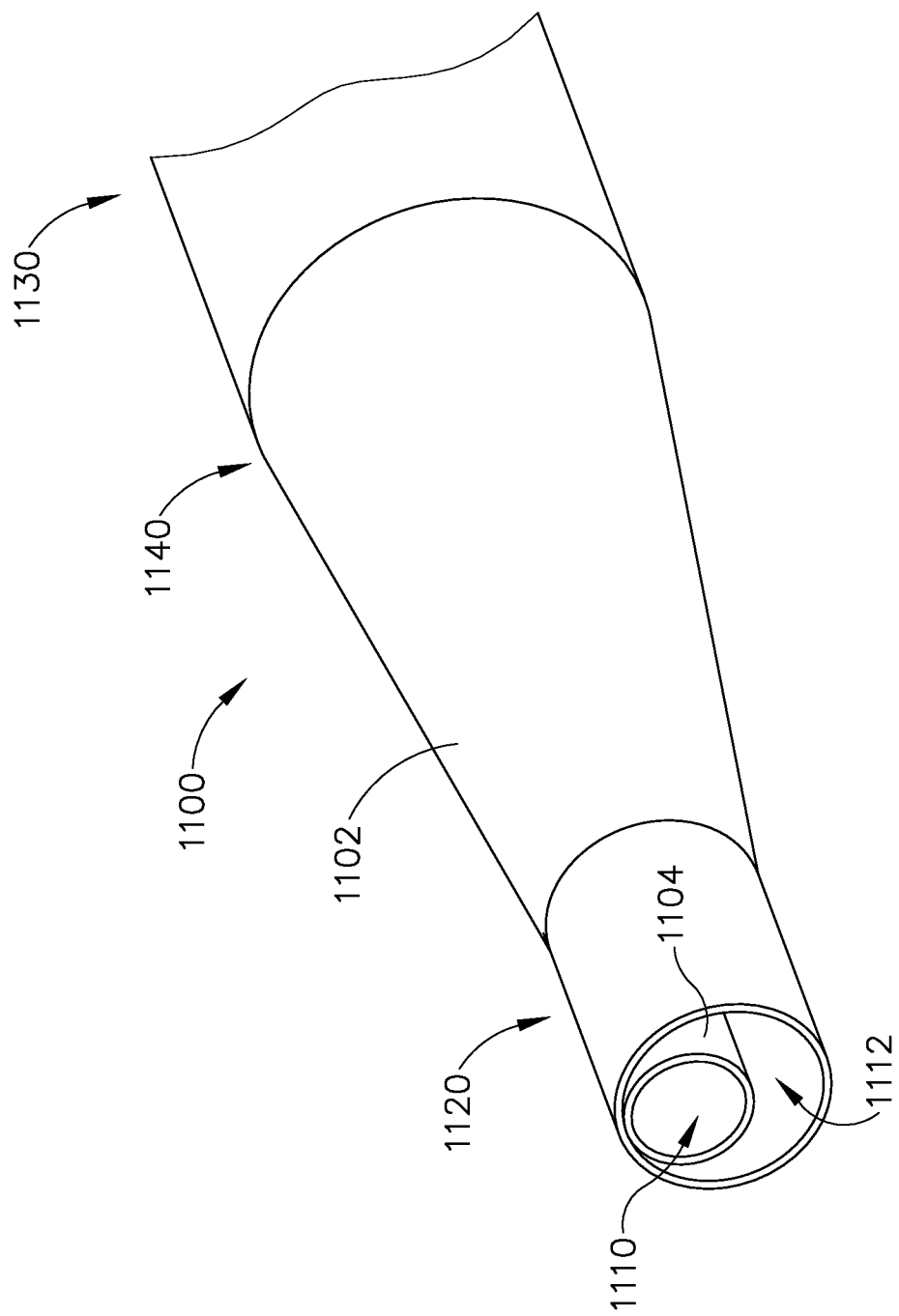
FIG. 84 depicts a perspective view of a distal end of an exemplary tube assembly that may be incorporated into the dilation catheter of the dilation catheter system of FIG. 1.
Figure 85:
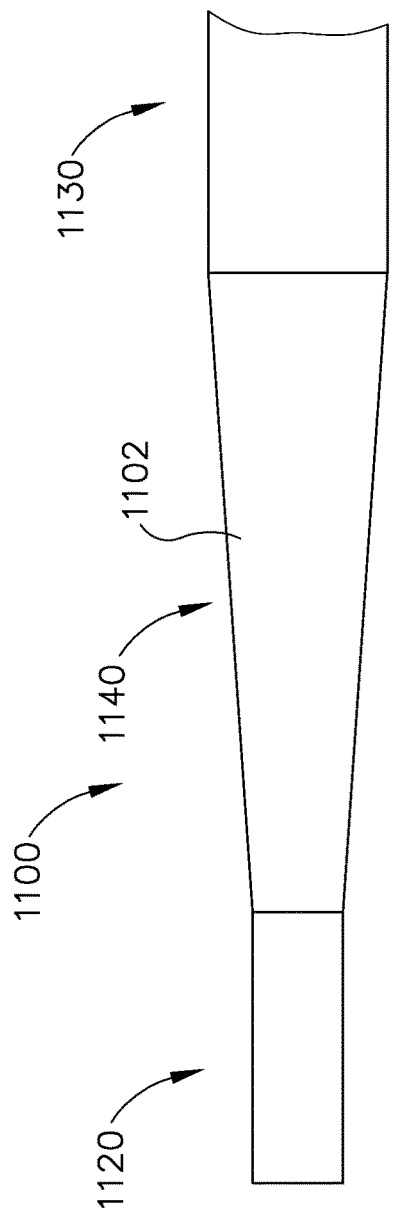
FIG. 85 depicts a side elevational view of the distal end of the tube assembly of FIG. 84.
Figure 86:
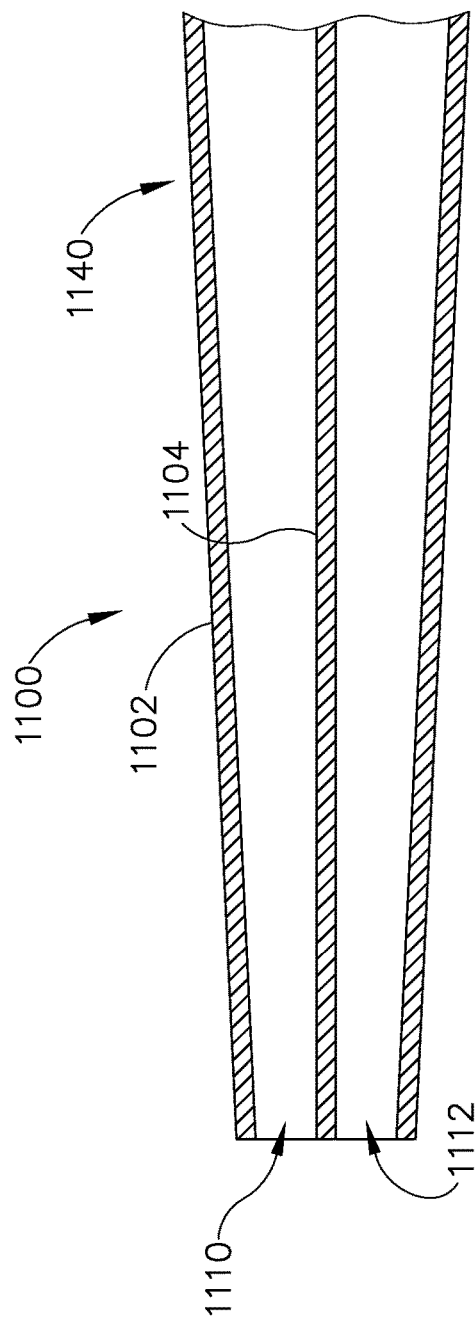
FIG. 86 depicts a cross-sectional side elevational view of the distal end of the tube assembly of FIG. 84.

FIGS. 84-86 show a distal end of an exemplary dilation catheter (1100) that may be used in place of dilation catheter (20, 108) described above. It should also be understood that the below teachings of dilation catheter (1100) may be readily combined with the above teachings of dilation catheter (1100). Dilation catheter (1100) of this example comprises an outer tubular wall (1102) and an inner wall (1104). Walls (1102, 1104) together define a first lumen (1110) and a second lumen (1112). By way of example only, first lumen (1110) may be configured to slidably receive guidewire (50, 106) and/or an irrigation catheter and/or an irrigation fluid. Second lumen (1112) may be in fluid communication with a balloon (22, 110) and an inflation fluid source, such that second lumen (1112) is used to provide selective inflation/deflation of balloon (22, 110). As best seen in FIG. 86, first and second lumens (1110, 1112) of dilator catheter (1100) are fluidly isolated from each other.

As best seen in FIG. 85, outer tubular wall (1102) transitions from a proximal portion (1130) having a larger diameter to a distal portion (1120) having a smaller diameter. A transition region (1140) provides a smoothly tapered transition between portions (1120, 1130). Dilation catheter (1100) thus has a "bump tube" type of configuration. By way of example only, outer tubular wall (1102) may transition from an outer diameter of approximately 0.085 inches (in proximal portion (1130)) to an outer diameter of approximately 0.075 inches (in distal portion (1120)). By way of further example only, first lumen (1110) may transition from an inner diameter of approximately 0.055 inches (in proximal portion (1130)) to an inner diameter of approximately 0.044 inches (in distal portion (1120)). Second lumen (1112) may transition from an inner diameter of approximately 0.032 inches (in proximal portion (1130)) to an inner diameter of approximately 0.013 inches (in distal portion (1120)). Alternatively, any other suitable dimensions may be used.

In some versions, the proximal end of a balloon (22, 110) is secured to proximal portion (1130) while a distal end of the same balloon (22, 110) is secured to distal portion (1120). Balloon (22, 110) may be bonded to these portions (1120, 1130) using any suitable techniques. Compared to conventional dilation catheters where both ends of a balloon (22, 110) are bonded to regions of a catheter having a uniform outer diameter, dilation catheter (1110) and the bonding technique described herein may reduce a risk of overheating material at the proximal bonding location and/or may reduce stiffness at the proximal bonding location. The configuration of dilation catheter (1110) may also provide better insertion/retraction forces, thereby enhancing performance of dilation catheter (1110).

VIII. Miscellaneous

It should be understood that any of the examples described herein may include various other features in addition to or in lieu of those described above. By way of example only, any of the examples described herein may also include one or more of the various features disclosed in any of the various references that are incorporated by reference herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices disclosed herein can be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, versions of the device may be disassembled, and any number of the particular pieces or parts of the device may be selectively replaced or removed in any combination. Upon cleaning and/or replacement of particular parts, versions of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a surgical facility. A device may also be sterilized using any other technique known in the art, including but not limited to beta or gamma radiation, ethylene oxide, or steam.

Having shown and described various versions of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A dilation catheter system, wherein the dilation catheter system comprises:
    (a) a handle extending along a longitudinal axis between a first proximal end and a first distal end;
    (b) a dilation assembly, wherein the dilation assembly comprises:
        (i) a dilator,
        (ii) a dilation catheter in fluid communication with the dilator, and
        (iii) a dilation catheter movement body coupled with the dilation catheter, wherein the dilation catheter movement body is slidably attached to the handle along a path such that the dilation catheter movement body is configured to translate relative to the handle to thereby actuate the dilation assembly relative to the handle; and
    (c) a guidewire assembly, wherein the guidewire assembly comprises:
        (i) a guidewire, and
        (ii) a guidewire movement body operatively coupled to the guidewire, wherein the guidewire movement body is slidably attached to the handle along the path independently of the dilation catheter movement body, wherein at least a first portion of the guidewire movement body is configured to actuate distally past the dilation catheter movement body, wherein at least a second portion of the guidewire movement body is configured to actuate proximally past the dilation catheter movement body.

2. The dilation catheter system of claim 1, wherein the dilation catheter movement body defines an opening, wherein the guidewire movement body is configured to actuate along the path through the opening.

3. The dilation catheter system of claim 2, wherein the opening and the guidewire movement body define a gap.

4. The dilation catheter system of claim 2, wherein the dilation movement body comprises a second proximal end and a second distal end, wherein the opening extends between the second proximal end and the second distal end.

5. The dilation catheter system of claim 4, wherein the first portion of the guidewire movement body comprises a third distal end, wherein the second portion of the guidewire movement body comprises a third proximal end, wherein the third distal end of the guidewire movement body extends distally past the dilation movement body when the third proximal end is housed within the opening of the dilation movement body.

6. The dilation catheter system of claim 5, wherein the third proximal end of the guidewire movement body extends proximally past the dilation movement body when the third distal end is housed within the opening of the dilation movement body.

7. The dilation catheter system of claim 1, wherein the handle further comprises a shaft housing the dilation catheter.

8. The dilation catheter system of claim 7, wherein the dilation catheter movement body is slidably coupled with the shaft via an opening.

9. The dilation catheter system of claim 8, wherein the handle further comprises an elongate track, wherein the dilation catheter movement body defines an elongate recess slidably coupled with the elongate track.

10. The dilation catheter system of claim 9, wherein the elongate track comprises a triangular cross-sectional profile.

11. The dilation catheter system of claim 7, wherein at least a portion of the guidewire is coaxial with the dilation catheter and the shaft.

12. The dilation catheter system of claim 7, wherein the shaft is rigid.

13. The dilation catheter system of claim 1, wherein the handle further comprises a pair of longitudinally extending bodies, wherein the guidewire movement body is slidably attached to the pair of longitudinally extending bodies.

14. The dilation catheter system of claim 13, wherein the pair of longitudinally extending bodies comprise a pair of rods.

15. The dilation catheter system of claim 14, wherein the handle further comprises a proximal cap attached to the pair of rods.

16. The dilation catheter system of claim 13, wherein the pair of longitudinally extending bodies comprises a rectangular track.

17. A dilation catheter system, wherein the dilation catheter system comprises:
 (a) a handle extending along a longitudinal axis between a first proximal end and a first distal end;
 (b) a dilation assembly, wherein the dilation assembly comprises:
  (i) a dilator,
  (ii) a dilation catheter in fluid communication with the dilator, and
  (iii) a dilation catheter movement body defining an opening, wherein the dilation catheter movement body is slidably attached to the handle such that the dilation catheter movement body is configured to translate relative to the handle to thereby actuate the dilation assembly relative to the handle; and
 (c) a guidewire assembly, wherein the guidewire assembly comprises:
  (i) a guidewire, and
  (ii) a guidewire movement body operatively coupled with the guidewire, wherein the guidewire movement body is slidably attached to the handle such that the guidewire movement body may translate through the opening of the dilation catheter movement body.

18. The dilation catheter system of claim 17, wherein the guidewire movement body comprises a first end and a second end, wherein the guidewire movement body comprises a length such that when the first end is housed within the opening, the second end extends out of the opening.

19. The dilation catheter system of claim 17, wherein the dilation catheter movement body and the guidewire movement body are configured to translate along the same path.

20. A dilation catheter system, wherein the dilation catheter system comprises:
 (a) a handle extending along a longitudinal axis between a first proximal end and a first distal end;
 (b) a dilation assembly, wherein the dilation assembly comprises:
  (i) a dilator,
  (ii) a dilation catheter in fluid communication with the dilator, and
  (iii) a dilation catheter movement body slidably attached to the handle such that the dilation catheter movement body may translate relative to the handle to thereby actuate the dilation assembly relative to the handle; and
 (c) a guidewire assembly, wherein the guidewire assembly comprises:
  (i) a guidewire, and
  (ii) a guidewire movement body operatively coupled with the guidewire, wherein the guidewire movement body is slidably attached to the handle independently of the dilation catheter movement body such that the guidewire movement body is configured to translate distally and proximally past the dilation catheter movement body.

* * * * *